United States Patent
Barneo Serra et al.

(10) Patent No.: US 9,702,879 B2
(45) Date of Patent: *Jul. 11, 2017

(54) METHODS AND PRODUCTS FOR IN VITRO DIAGNOSIS, IN VITRO PROGNOSIS AND THE DEVELOPMENT OF DRUGS AGAINST INVASIVE CARCINOMAS

(75) Inventors: Luis Barneo Serra, Derio-Vizcaya (ES); Carmen Garcia Pravia, Derio-Vizcaya (ES); Juan Ramon De Los Toyos Gonzalez, Derio-Vizcaya (ES); Marcos Garcia Ocana, Derio-Vizcaya (ES); Jose Fernando Vazquez Villa, Derio-Vizcaya (ES); Nelson Fuentes Martinez, Derio-Vizcaya (ES); Jokin Del Amo Iribarren, Derio-Vizcaya (ES); Laureano Simon Buela, Derio-Vizcaya (ES)

(73) Assignee: Oncomatryx Biopharma, S.L., Vizcaya (ES)

( * ) Notice: Subject to any disclaimer, the term of this patent is extended or adjusted under 35 U.S.C. 154(b) by 223 days.

This patent is subject to a terminal disclaimer.

(21) Appl. No.: 14/237,682

(22) PCT Filed: Aug. 8, 2012

(86) PCT No.: PCT/ES2012/070616
§ 371 (c)(1),
(2), (4) Date: Oct. 21, 2014

(87) PCT Pub. No.: WO2013/021088
PCT Pub. Date: Feb. 14, 2013

(65) Prior Publication Data
US 2015/0362496 A1    Dec. 17, 2015

(30) Foreign Application Priority Data

Aug. 9, 2011 (ES) .................................. 201131374

(51) Int. Cl.
G01N 33/573 (2006.01)
G01N 33/574 (2006.01)
C07K 16/18 (2006.01)
C07K 16/30 (2006.01)
G01N 33/50 (2006.01)
G01N 33/68 (2006.01)
C12Q 1/68 (2006.01)

(52) U.S. Cl.
CPC ....... *G01N 33/57484* (2013.01); *C07K 16/18* (2013.01); *C07K 16/30* (2013.01); *C12Q 1/6886* (2013.01); *G01N 33/5011* (2013.01); *G01N 33/6881* (2013.01); *G01N 33/6887* (2013.01); *C07K 2317/33* (2013.01); *C12Q 2600/118* (2013.01); *G01N 2333/78* (2013.01); *G01N 2800/56* (2013.01)

(58) Field of Classification Search
None
See application file for complete search history.

(56) References Cited

FOREIGN PATENT DOCUMENTS

| WO | WO 2005/011619 | 2/2005 |
| WO | WO 2008/051374 | 5/2008 |
| WO | WO 2008/079269 | 7/2008 |
| WO | WO 2009/047216 | 4/2009 |
| WO | WO 2009/052573 | 4/2009 |
| WO | WO 2010/061996 | 6/2010 |
| WO | WO 2011/130435 | 10/2011 |
| WO | WO 2012/142330 | 10/2012 |
| WO | WO 2013/021088 | 2/2013 |

OTHER PUBLICATIONS

Fischer et al. Colorectal carcinogenesis is associated whith stromal expression of COL11A1 and COL5A2. Carcinogenesis, vol. 22, No. 6, pp. 875-878, 2001.*
Fischer et al (Carcinogenisis 22:875-78, 2001).*
Paul, Fundamental Immunology, 3rd Edition, 1993, pp. 292-295.*
Rudikoff et al., Proc. Natl. Acad. Sci. USA 1982 vol. 79: p. 1979.*
Casset et all, BBRC 307, 198-205 2003.*
Pascalis et al, The Journal of Immunology vol. 169, 3076-3084, 2002.*
Garcia Pravia et al (British J. Surgery, 2009, 96 (S5):17, filed Feb. 7, 2014.*
Fresno et al, Virchows Arch 455 (suppl 1), OP17.10, S482, 2009, filed Feb. 7, 2014).*
Garcia Pravia et al, British J. Surgery, 2009, 96 (S5):11.*
Fuentes et al (Virchows Arch 457 (suppl 1) S457, 2010, filed Feb. 7, 2014.*
Ahlgren, "Epidemiology and Risk Factors in Pancreatic Cancer", 1996, Semin. Oncol, 23:241-250.
Badea et al., "Combined Gene Expression Analysis of Whole-Tissue and Microdissected Pancreatic Ductal Adenocarcinoma identifies Genes Specifically Overexpressed in Tumor Epithelia", 2008, Hepato-Gastroenterol. 55(88): 2015-2026.
Barbareschi, et al., "p63, a p53 Homologue, is a Selective Nuclear Marker of Myoepithelial Cells of Human Breast", 2001, Am J Surg Path, 25:1054-1060.

(Continued)

Primary Examiner — Lei Yao
(74) Attorney, Agent, or Firm — Greer, Burns & Crain, Ltd.

(57) ABSTRACT

The present invention relates to in vitro methods and products for detecting the presence of an invasive carcinoma in an individual, for determining and/or predicting the stage and/or invasiveness of said carcinoma in an individual, or for monitoring the effect of the therapy administered to an individual who has said carcinoma based on col11a1 gene and proCOL11A1 protein expression. The invention also relates to the search for, identification, development and evaluation of the efficacy of compounds for therapy for said carcinoma, for the purpose of developing new medicinal products. The invention also relates to agents inhibiting proCOL11A1 protein expression and/or activity, and/or the effects of this expression.

9 Claims, 10 Drawing Sheets

(56) References Cited

OTHER PUBLICATIONS

Boudreau, and Bissell, "Extracellular matrix signaling: integration of form and function in normal and malignant cells", 1998, Curr. Opin. Cell Biol . . . 10:640-646.
Bowen et al., Immunohistochemical Localization of Collagen Type XI α1 and α2 Chains in Human Colon Tissue2008 J. Hist. Cyt.,, 56(3):275-283.
Buckanovich et al., "Tumor Vascular Proteins as Biomarkers in Ovarian Cancer", 2007, J. Clin. Oncol., 25(7): 852-861.
Byungwoo , et al., "Relationships and Differently Expressed Genes among Pancreatic Cancers Examined by Large-scale Serial Analysis of Gene Expression", 2002, Cancer Res., 62:819-826.
Chong et al., "Great potential of a panel of multiple hMtH1, SPD, ITGA11 and COL11A1 markers for diagnosis of patients with non-small cell lung cancer", 2006, Oncol Rep, 16(5):981-988.
Cortese et al., "Correltaive gene expression and DNA methylation profiling in lung development nominate new biomarkers in lung cancer", 2008, Int. J. Biochem. And Cell Biol., 40(8): 1494-15.
Doherty et al., "Gene Expression in Normal Urotheliun Depends on Location within the Bladder: a Possible Link to Bladdder Carcinogenesis", 2006, Europ. Urol., 50(2): 290-301.
Ellsworth et al., 2009, Clin. Exp. Metastasis, 26: 205-13.
Erkan, et al., "Organ-, inflammation- and cancer specific transcriptional fingerprints of pancreatic and hepatic stellate cells", 2010, Mol. Cancer, 9:88-103.
Feng, Y., et al., 2007, Breast Cancer Res. Treat.,I03(3):319-329.
Fernandes et al., "Collagen XI chain misassembly in cartilage of the chondrodysplasia (cho) mouse", 2007, Matrix Biol., 26(8): 597-603.
Fischer et al., "Colorectal carcinogenesis is associated with stromal expression of COL11A1 and COL5A2", 2001, Carcinogenesis, 22(6): 875-878.
Fischer et al., "COLIIAI in FAP polyps and in sporadic colorectal tumors", 2001, BMC Cancer, 1(1): 17.
Fresno et al., "Anti COL11 is a useful marker of infiltrating pancreatic cancer" Virchow Archiv., 2009,455 (Supp. 1): 1: 62.
Fuentes et al., "Anticol11a1 a marker of infiltration in bronchioloalveolar lung carcinoma", 2010, Virchows Archiv., 457(2): 230.
Garcia Pravia et al., "ESSR Abstracts 2009", 2009, Virchows Archiv., 455 (Supp. 1): 32-33.
Iacobuzio-Donahue, "Discovery of Novel Tumor Markers of Pancreatic Cancer Using Global Gene Expression Technology", 2002, Am. J. Pathology, 160(4):1239-1249.
Jan Akervall, "Genomic screening of head and neck cancer and its implications for therapy planning", 2006, Europ. Arch. Oto-Rhyno-Lar . and Head and Neck , 263(4): 297-304.
Ken-Ichi Iyama et al., "Differential expression of two exons of the α1 (X1) collagen gene (Col11a1) in the mouse embryo", 2001, Matrix Biol., 20(1): 53-61.
Kim Hoon et al., "Multi-cancer computational analysis reveals invasion-associated variant of desmoplastic reaction involving INHBA, THBS2 and COL11A1", 2010, BMC Med. Gen., 3(1) :51.
Koker, et al., "p63 Expression in Breast Cancer A highly Sensitive and Specific Marker of Metaplastic Carcinoma", 2004, Am J Surg Path, 28:1506-151 2.
Kovacs etal. ,"The Heidelberg Classification of Renal Cell Tumors", 1997 J. Pathol., 183:131-133.
Lerwill M.F., "Current Practical Applications of Diagnostic Immunohistochemistry in Breast Pathology", 2004, Am J Surg Path, 28:1076-1091.
Li, Y., et al. , "A Fibrillar Collagen Gene, Col11a1, is Essential for Skeletal Morphogenesis", 1995, Cell, , 80:423-430.
Lopez-Iago et al., "Deconstructing tumor-stroma interactions during renal cell carcinoma metastasis", 2010, Am. Association for Can. Res., Abstract 2247.

Mart et al., "Organ-, inflammation- and cancer specific transcriptional fingerprints of pancreatic and hepatic stellate cells", 2010, Mol. Cancer, 9(1): 88.
Mizutani et al., "Significance of Serum Soluble Fas Ligand in Patients with Bladder Carcinoma", 2001, Cancer, 92(2): 287-293.
Moradi-Ameli et al., "Different Splice Variants of Cartilage α1(XI) Collagen Chain Undergo Uniform Amino-Terminal Processing", 1998, Matrix Biol., 17(5): 393-396.
Morris et al., "Developmentally Regulated Alternative Splicing of the α1(XI) Collagen Chain: Spatial and Temporal Segregation of Isoforms in the Cartilage of Fetal Rat Long Bones", 2000, J. Histochem and Cytochem , 48(6): 725-741.
Nielsen et al., "Immunohistochemical and Clinical Characterization of the Basal-Like Subtype of Invasive Breast Carcinoma", 2004 Clin. Cancer Res, 10:5367-5374.
Perou et al., "Molecular portraits of human breast tumours", 2000 Nature, 406:747-752.
Pilarsky et al., "Activation of Wnt signalling in stroma from pancreatic cancer identified by gene expression profiling", 2008, J. Cel. Mol. Med., 12(6B):2823-35.
Rabinovitch , et al. "Patterns of Failure Following Surgical Resection of Renal Cell Carcinoma: Implications for Adjuvant Local and Systemic Therapy", 1994, J. Clin. Oncol., 12:206-212.
Sandberg et al., "Co-expression of collagens II and XI and alternative splicing of exon 2 of collagen II in several developing human tissues", 1993. Biochem . J., 294:595-602.
Sandock, et al., "A New Protocol for the Followup of Renal Cell Carcinoma Based on Pathological Stage", 1995,1. Urol, 154:28-31.
Schmalbach et al., "Molecular Profiling and the Identification of Genes Associated with Metastatic Oral Cavity/Pharynx Squamous Cell Carcinoma", 2004, Arch. Oto-Rhyno-Lar. Head and Neck Surg, 130(3): 295-302.
Sok et al., "Tissue-Specific Gene Expression of Head and Neck Squamous Cell Carcinoma in Vivo by Complementary DNA Microarray Analysis", 2003, Arch. Oto-Rhyno-Lar. Head and Neck Surg., 129(7) 760-770.
Stracke, et al., "The Role of the Extracellular Matrix in Tumor Cell Metastasis", 1994, In vivo, 8:49-58.
Suceveanu, et al., "Introduction of Cytogenetic Tests in Colorectal Cancer Screening", 2009, J. Gastrointestin. Liver Dis, 18(1):33-38.
Takao et al., "Comparison of Relapse and Long-term Survival between Pylorus-preserving and Whipple Pancreaticoduodenectomy in Periampullary Cancer", 1998, Am. J. Surg., 176:467-470.
Wang et al., "Novel candidate tumor marker genes for lung adenocarcinoma", 2002, Oncogene, 21: 7598-7604.
Warshaw and Fernandez del Castillo, "Pancreatic Carcinoma", 1992, N. Eng. J. Med., 326:455-465.
Werling et al., "Immunohistochemical Distinction of Invasive From Noninvasive Breast Lesions", 2003, Am J Surg Path, 27:82-90.
Ying Sun et al., "Secreted Phosphoprotein 1 Upstream Invasive Network Construction and Analysis of Lung Adencarcinoma" 2010, Cell Biochem and Biophys ., 56(2-3): 59-71.
Yoshioka et al., "Developmental Pattern of Expression of the Mouse 1(XI) Collagen Gene (Col11a1 )", 1995. Dev. Dyn., 204: 41-47.
Zhao et al., 2009, "A Potential Role of Collagens Expression in Distinguishing Between Premalignant and Malignant Lesions in Stomach", The Anatomical Record, 292: 692-700.
De Vere White et al., "Predicting Prognosis in Patients with Superficial Bladder Cancer", 1998, Oncology, 12:1717-1723.
Kjaer et al., "Postoperative Radiotherapy in Stage II and III Renal Adenocarinoma. A Randomized Trial by the Copenhagen Renal Cancer Study Group", 1987, Intl. J. Radiat. Oncol. Bioi. Phys., 13:665-672.
Gautier, Robin et al. "Restricted Diversity of Antigen Binding Residues of Antibodies Revealed by Computational Alanine Scanning of 227 Antibody-Antigen Complexes", J. Mol. Biol. (2014) 426, pp. 3729-3743.

* cited by examiner

SEQUENCE LISTING

```
<160> NUMBER OF SEQ ID NOS: 43

<210> SEQ ID NO 1
<211> LENGTH: 23
<212> TYPE: DNA
<213> ORGANISM: Artificial Sequence
<220> FEATURE:
<223> OTHER INFORMATION: Sense primer specific for the col11a1 gene

<400> SEQUENCE: 1
tggtgatcag aatcagaagt tcg                                          23

<210> SEQ ID NO 2
<211> LENGTH: 23
<212> TYPE: DNA
<213> ORGANISM: Artificial Sequence
<220> FEATURE:
<223> OTHER INFORMATION: Antisense primer specific for the col11a1 gene

<400> SEQUENCE: 2
aggagagttg agaattggga atc                                          23

<210> SEQ ID NO 3
<211> LENGTH: 8
<212> TYPE: PRT
<213> ORGANISM: Artificial Sequence
<220> FEATURE:
<223> OTHER INFORMATION: CDR-H1

<400> SEQUENCE: 3

Gly Tyr Ser Phe Thr Gly Tyr Tyr
1               5

<210> SEQ ID NO 4
<211> LENGTH: 8
<212> TYPE: PRT
<213> ORGANISM: Artificial Sequence
<220> FEATURE:
<223> OTHER INFORMATION: CDR-H2

<400> SEQUENCE: 4

Ile Asn Cys Tyr Asn Gly Ala Thr
1               5

<210> SEQ ID NO 5
<211> LENGTH: 12
<212> TYPE: PRT
<213> ORGANISM: Artificial Sequence
<220> FEATURE:
<223> OTHER INFORMATION: CDR-H3

<400> SEQUENCE: 5

Ala Ile Trp Asp Tyr Glu Phe His Val Met Asp Tyr
1               5                   10
```

```
<210> SEQ ID NO 6
<211> LENGTH: 5
<212> TYPE: PRT
<213> ORGANISM: Artificial Sequence
<220> FEATURE:
<223> OTHER INFORMATION: CDR-L1

<400> SEQUENCE: 6

Ser Ser Val Asn Tyr
1               5

<210> SEQ ID NO 7
<211> LENGTH: 9
<212> TYPE: PRT
<213> ORGANISM: Artificial Sequence
<220> FEATURE:
<223> OTHER INFORMATION: CDR-L3

<400> SEQUENCE: 7

Gln Gln Phe Thr Ser Ser Pro Trp Thr
1               5

<210> SEQ ID NO 8
<211> LENGTH: 119
<212> TYPE: PRT
<213> ORGANISM: Artificial Sequence
<220> FEATURE:
<223> OTHER INFORMATION: VH_1E8.33

<400> SEQUENCE: 8

Glu Val Gln Leu Gln Glu Ser Gly Pro Glu Leu Val Lys Thr Gly Ser
1               5                   10                  15

Ser Val Lys Ile Ser Cys Lys Ala Ser Gly Tyr Ser Phe Thr Gly Tyr
                20                  25                  30

Tyr Met His Trp Val Lys Gln Ser Gln Gly Lys Ser Leu Glu Trp Ile
            35                  40                  45

Gly Tyr Ile Asn Cys Tyr Asn Gly Ala Thr Ser Tyr Asn Arg Asn Phe
        50                  55                  60

Lys Gly Lys Ala Thr Phe Thr Val Asp Thr Ser Ser Thr Ala Tyr
65                  70                  75                  80

Met Gln Phe Asn Ser Leu Thr Ser Gly Asp Ser Ala Val Tyr Tyr Cys
                85                  90                  95

Ala Ile Trp Asp Tyr Glu Phe His Val Met Asp Tyr Trp Gly Gln Arg
            100                 105                 110

Thr Ser Leu Thr Val Ser Ser
        115

<210> SEQ ID NO 9
<211> LENGTH: 106
<212> TYPE: PRT
<213> ORGANISM: Artificial Sequence
<220> FEATURE:
<223> OTHER INFORMATION: Vkappa_1E8.33

<400> SEQUENCE: 9

Glu Asn Val Leu Thr Gln Ser Pro Ala Ile Met Ser Ala Ser Leu Gly
1               5                   10                  15

Glu Lys Val Thr Met Ser Cys Arg Ala Ser Ser Ser Val Asn Tyr Met
                20                  25                  30

Tyr Trp Tyr Gln Gln Lys Ser Asp Ala Ser Pro Lys Leu Trp Ile Tyr
            35                  40                  45

Tyr Thr Ser Asn Leu Ala Pro Gly Val Pro Ala Arg Phe Ser Gly Ser
```

-continued

```
            50                  55                  60
Gly Ser Gly Asn Ser Tyr Ser Leu Thr Ile Ser Ser Met Glu Gly Glu
 65                  70                  75                  80

Asp Ala Asp Thr Tyr Tyr Cys Gln Gln Phe Thr Ser Ser Pro Trp Thr
                 85                  90                  95

Phe Gly Gly Gly Thr Lys Leu Glu Ile Lys
            100                 105

<210> SEQ ID NO 10
<211> LENGTH: 17
<212> TYPE: DNA
<213> ORGANISM: Artificial Sequence
<220> FEATURE:
<223> OTHER INFORMATION: Sense primer specific for the human ribosomal
      protein L10 gene

<400> SEQUENCE: 10
tgcgatggct gcacaca                                                  17

<210> SEQ ID NO 11
<211> LENGTH: 23
<212> TYPE: DNA
<213> ORGANISM: Artificial Sequence
<220> FEATURE:
<223> OTHER INFORMATION: Antisense primer specific for the human
      ribosomal protein L10 gene

<400> SEQUENCE: 11
tcccttagag caacccatac aac                                           23

<210> SEQ ID NO 12
<211> LENGTH: 14
<212> TYPE: DNA
<213> ORGANISM: Artificial Sequence
<220> FEATURE:
<223> OTHER INFORMATION: Oligonucleotide R0

<400> SEQUENCE: 12
ttgggtgctg aaga                                                     14

<210> SEQ ID NO 13
<211> LENGTH: 26
<212> TYPE: DNA
<213> ORGANISM: Artificial Sequence
<220> FEATURE:
<223> OTHER INFORMATION: Oligonucleotide F0

<400> SEQUENCE: 13
tcttcagcac ccaaggctgc tcaagc                                        26

<210> SEQ ID NO 14
<211> LENGTH: 26
<212> TYPE: DNA
<213> ORGANISM: Artificial Sequence
<220> FEATURE:
<223> OTHER INFORMATION: Oligonucleotide R14

<400> SEQUENCE: 14
tctgaggttc ctgagcttga gcagcc                                        26

<210> SEQ ID NO 15
<211> LENGTH: 29
<212> TYPE: DNA
<213> ORGANISM: Artificial Sequence
<220> FEATURE:
```

<223> OTHER INFORMATION: Oligonucleotide F26

<400> SEQUENCE: 15
tcaggaacct cagatagatg aggcaaaca                                    29

<210> SEQ ID NO 16
<211> LENGTH: 30
<212> TYPE: DNA
<213> ORGANISM: Artificial Sequence
<220> FEATURE:
<223> OTHER INFORMATION: Oligonucleotide R40

<400> SEQUENCE: 16
gaaaatcatc aacgatgttt gcctcatcta                                   30

<210> SEQ ID NO 17
<211> LENGTH: 32
<212> TYPE: DNA
<213> ORGANISM: Artificial Sequence
<220> FEATURE:
<223> OTHER INFORMATION: Oligonucleotide F55

<400> SEQUENCE: 17
tcgttgatga ttttcaagaa tacaactatg ga                                32

<210> SEQ ID NO 18
<211> LENGTH: 33
<212> TYPE: DNA
<213> ORGANISM: Artificial Sequence
<220> FEATURE:
<223> OTHER INFORMATION: Oligonucleotide R70

<400> SEQUENCE: 18
ggtaactttc cattgttcca tagttgtatt ctt                               33

<210> SEQ ID NO 19
<211> LENGTH: 29
<212> TYPE: DNA
<213> ORGANISM: Artificial Sequence
<220> FEATURE:
<223> OTHER INFORMATION: Oligonucleotide F87

<400> SEQUENCE: 19
acaatggaaa gttaccagac agaagctcc                                    29

<210> SEQ ID NO 20
<211> LENGTH: 27
<212> TYPE: DNA
<213> ORGANISM: Artificial Sequence
<220> FEATURE:
<223> OTHER INFORMATION: Oligonucleotide R103

<400> SEQUENCE: 20
cagaaacatg cctaggagct tctgtct                                      27

<210> SEQ ID NO 21
<211> LENGTH: 27
<212> TYPE: DNA
<213> ORGANISM: Artificial Sequence
<220> FEATURE:
<223> OTHER INFORMATION: Oligonucleotide F116

<400> SEQUENCE: 21
taggcatgtt tctgggacaa atgagcc                                      27

```
<210> SEQ ID NO 22
<211> LENGTH: 28
<212> TYPE: DNA
<213> ORGANISM: Artificial Sequence
<220> FEATURE:
<223> OTHER INFORMATION: Oligonucleotide R130

<400> SEQUENCE: 22
tcttcaactg gatttggctc atttgtcc                                     28

<210> SEQ ID NO 23
<211> LENGTH: 34
<212> TYPE: DNA
<213> ORGANISM: Artificial Sequence
<220> FEATURE:
<223> OTHER INFORMATION: Oligonucleotide F143

<400> SEQUENCE: 23
aaatccagtt gaagaaatat ttactgaaga atat                              34

<210> SEQ ID NO 24
<211> LENGTH: 32
<212> TYPE: DNA
<213> ORGANISM: Artificial Sequence
<220> FEATURE:
<223> OTHER INFORMATION: Oligonucleotide R158

<400> SEQUENCE: 24
cctctcccgt tagatattct tcagtaaata tt                                32

<210> SEQ ID NO 25
<211> LENGTH: 29
<212> TYPE: DNA
<213> ORGANISM: Artificial Sequence
<220> FEATURE:
<223> OTHER INFORMATION: Oligonucleotide F177

<400> SEQUENCE: 25
ctaacgggag aggattatga ttcccagag                                    29

<210> SEQ ID NO 26
<211> LENGTH: 32
<212> TYPE: DNA
<213> ORGANISM: Artificial Sequence
<220> FEATURE:
<223> OTHER INFORMATION: Oligonucleotide R190

<400> SEQUENCE: 26
atcctcagaa tttttcctct gggaatcata at                                32

<210> SEQ ID NO 27
<211> LENGTH: 33
<212> TYPE: DNA
<213> ORGANISM: Artificial Sequence
<220> FEATURE:
<223> OTHER INFORMATION: Oligonucleotide F206

<400> SEQUENCE: 27
gaaaaattct gaggatacac tatatgaaaa caa                               33

<210> SEQ ID NO 28
<211> LENGTH: 31
<212> TYPE: DNA
<213> ORGANISM: Artificial Sequence
<220> FEATURE:
<223> OTHER INFORMATION: Oligonucleotide R222
```

<400> SEQUENCE: 28
tgccgtctat ttctttgttt tcatatagtg t    31

<210> SEQ ID NO 29
<211> LENGTH: 29
<212> TYPE: DNA
<213> ORGANISM: Artificial Sequence
<220> FEATURE:
<223> OTHER INFORMATION: Oligonucleotide F239

<400> SEQUENCE: 29
agaaatagac ggcagggatt ctgatcttc    29

<210> SEQ ID NO 30
<211> LENGTH: 30
<212> TYPE: DNA
<213> ORGANISM: Artificial Sequence
<220> FEATURE:
<223> OTHER INFORMATION: Oligonucleotide R253

<400> SEQUENCE: 30
aatctccatc taccagaaga tcagaatccc    30

<210> SEQ ID NO 31
<211> LENGTH: 31
<212> TYPE: DNA
<213> ORGANISM: Artificial Sequence
<220> FEATURE:
<223> OTHER INFORMATION: Oligonucleotide F268

<400> SEQUENCE: 31
tggtagatgg agatttaggc gaatatgatt t    31

<210> SEQ ID NO 32
<211> LENGTH: 36
<212> TYPE: DNA
<213> ORGANISM: Artificial Sequence
<220> FEATURE:
<223> OTHER INFORMATION: Oligonucleotide R283

<400> SEQUENCE: 32
catattcttt atattcataa aaatcatatt cgccta    36

<210> SEQ ID NO 33
<211> LENGTH: 36
<212> TYPE: DNA
<213> ORGANISM: Artificial Sequence
<220> FEATURE:
<223> OTHER INFORMATION: Oligonucleotide F299

<400> SEQUENCE: 33
ttatgaatat aaagaatatg aagataaacc aacaag    36

<210> SEQ ID NO 34
<211> LENGTH: 30
<212> TYPE: DNA
<213> ORGANISM: Artificial Sequence
<220> FEATURE:
<223> OTHER INFORMATION: Oligonucleotide R319

<400> SEQUENCE: 34
cttcattagg ggggcttgtt ggtttatctt    30

<210> SEQ ID NO 35
<211> LENGTH: 28

<212> TYPE: DNA
<213> ORGANISM: Artificial Sequence
<220> FEATURE:
<223> OTHER INFORMATION: Oligonucleotide F335

<400> SEQUENCE: 35
cccccctaat gaagaatttg gtccaggt                                          28

<210> SEQ ID NO 36
<211> LENGTH: 28
<212> TYPE: DNA
<213> ORGANISM: Artificial Sequence
<220> FEATURE:
<223> OTHER INFORMATION: Oligonucleotide R349

<400> SEQUENCE: 36
gtttctgctg gtacacctgg accaaatt                                          28

<210> SEQ ID NO 37
<211> LENGTH: 31
<212> TYPE: DNA
<213> ORGANISM: Artificial Sequence
<220> FEATURE:
<223> OTHER INFORMATION: Oligonucleotide F363

<400> SEQUENCE: 37
gtaccagcag aaactgatat tacagaaaca a                                      31

<210> SEQ ID NO 38
<211> LENGTH: 31
<212> TYPE: DNA
<213> ORGANISM: Artificial Sequence
<220> FEATURE:
<223> OTHER INFORMATION: Oligonucleotide R377

<400> SEQUENCE: 38
atggccattt atgcttgttt ctgtaatatc a                                      31

<210> SEQ ID NO 39
<211> LENGTH: 26
<212> TYPE: DNA
<213> ORGANISM: Artificial Sequence
<220> FEATURE:
<223> OTHER INFORMATION: Oligonucleotide F394

<400> SEQUENCE: 39
gcataaatgg ccatggtgca tatgcg                                            26

<210> SEQ ID NO 40
<211> LENGTH: 25
<212> TYPE: DNA
<213> ORGANISM: Artificial Sequence
<220> FEATURE:
<223> OTHER INFORMATION: Oligonucleotide R408

<400> SEQUENCE: 40
gtcaagcctc catcgcatat gcacc                                             25

<210> SEQ ID NO 41
<211> LENGTH: 13
<212> TYPE: DNA
<213> ORGANISM: Artificial Sequence
<220> FEATURE:
<223> OTHER INFORMATION: Oligonucleotide R420

<400> SEQUENCE: 41

```
atggaggctt gac                                                    13

<210> SEQ ID NO 42
<211> LENGTH: 30
<212> TYPE: DNA
<213> ORGANISM: Artificial Sequence
<220> FEATURE:
<223> OTHER INFORMATION: Forward oligonucleotide for PCR 2 and cloning

<400> SEQUENCE: 42
atcggagaat tctcttcagc acccaaggct                                  30

<210> SEQ ID NO 43
<211> LENGTH: 34
<212> TYPE: DNA
<213> ORGANISM: Artificial Sequence
<220> FEATURE:
<223> OTHER INFORMATION: Reverse oligonucleotide for PCR 2 and cloning

<400> SEQUENCE: 43
gcttcggacg tcaattatac gtggtaccgg taaa                             34
```

METHODS AND PRODUCTS FOR IN VITRO DIAGNOSIS, IN VITRO PROGNOSIS AND THE DEVELOPMENT OF DRUGS AGAINST INVASIVE CARCINOMAS

CROSS-REFERENCES TO RELATED APPLICATIONS

This patent application is a national stage of PCT/ES2012/070616 which claims its priority to Spanish Patent Application P201131374, the entire disclosures of which are incorporated herein by reference.

FIELD OF THE INVENTION

The present invention relates to in vitro methods and products for detecting the presence of an invasive carcinoma in an individual, for determining and/or predicting the stage and/or invasiveness of said carcinoma in an individual, or for monitoring the effect of the therapy administered to an individual who has said carcinoma. The invention also relates to the search for, identification, development and evaluation of the efficacy of compounds for therapy for said carcinoma, for the purpose of developing new medicinal products. The invention also relates to agents inhibiting proCOL11A1 protein expression and/or activity, and/or the effects of this expression.

BACKGROUND OF THE INVENTION

Cancer is one of the main public health problems worldwide. According to the GLOBOCAN database of the International Agency for Research on Cancer, which belongs to the World Health Organization, over 10 million cases of cancer were diagnosed worldwide in the year 2000, and the number of deaths due to cancer in the year 2000 was greater than 6 million people.

Despite all the advances that have been made in the past 20 years, cancer is still one of the main causes of death around the world. During these years successful advances have been made in the prevention and treatment of early stages of many of the different diseases that are comprised within this term. However, there have been very few advances in the development of new methods for the diagnosis or treatment of advanced and invasive stages of the disease.

During the process of becoming malignant, tumor cells change their gene expression pattern, which alters cell processes, such as cell architecture maintenance, cell adhesion, cell death and cell proliferation. These modifications generate not only changes in the cells themselves, but they also make some stromal cells receive altered molecular signals and change their behavioral pattern and gene expression pattern, acquiring a typical morphology of myofibroblasts. The molecules secreted by these myofibroblasts in response to the adjacent tumor can in turn contribute in a different manner to promoting response to the adjacent tumor can in turn contribute in a different manner to promoting tumor growth and invasion, such that a paracrine loop between the tumor and stroma is established. Scientific evidence has been generated in recent years which points with increasingly greater precision to the peritumoral stroma as one of the main promoters of tumor invasiveness as well as of therapy resistance phenomena.

The methods and products for diagnosis and therapy claimed by the authors of the present invention are within this novel research framework because they are based on the exploitation of the col11a1 gene and the proCOL11A1 protein present in stromal cells of invasive carcinomas as a potential therapeutic marker and/or target for the diagnosis, prognosis and treatment of these carcinomas.

An invasive carcinoma is a malignant neoplasm made up of epithelial cells which infiltrate and destroy the surrounding tissues; they are generally malignant tumors which, during growth, infiltrate and break the basal lamina leading to metastasis. Illustrative examples of invasive carcinomas include pancreatic cancer, renal carcinoma, transitional bladder carcinoma, bronchoalveolar carcinoma, and breast cancer, among others.

Unlike other tumors, what is surprising about pancreatic cancer is its phenotypic clinical homogeneity. The clinical behavior of pancreatic cancer is homogenous and always unfavorable, without significant differences in survival according to the stage. The number of patients with pancreatic cancer with a good prognosis is insignificant. A possible explanation is that the disease spreads even in patients with small stage I tumors. With the exception of fortuitous cases, diagnosis in an initial phase is difficult; 75% of the patients diagnosed have an advanced disease (Stages III and IV). It is a very aggressive neoplasm resistant to cytostatic treatments and only between 1 and 4% of cases are still alive five years after the diagnosis, provided that the tumor is localized and could be removed in its entirety (Warshaw A. L., and Femandes del Castillo C., N. Eng. J. Med., 1992, 326:455-465; Ahigren J. D., Semin. Oncol. 1996, 23:241-250). Pancreatic ductal adenocarcinoma was the cause of over 138,000 deaths worldwide and over 2,600 in Spain in the year 2008 (GLOBOCAN). Therefore, in the case of pancreatic cancer, both the development of early diagnosis systems and effective therapies are crucial for controlling the disease (Byungwoo R., et al., Cancer Res., 2002, 62:819-826).

In the case of renal carcinoma, 50-80% of the patients diagnosed develop metastasis, and 90-95% of these patients who have developed metastasis die during the 5 years after diagnosis (Rabinovitch R. A., et al., J. Clin. Oncol., 1994, 12:206-212; Sandock, D. S., et al., J. Urol, 1995, 154:28-31). Renal carcinoma was the cause of over 72,000 deaths worldwide and over 1,200 in Spain in the year 2008 (GLOBOCAN). Advances in the knowledge of kidney cancer genetics have allowed the classification of different types of renal tumors. The most common conventional subtype is renal cell carcinoma, which is different from the papillary, chromophobe or collecting duct subtypes. Renal oncocytoma is a benign neoplasm occasionally indistinguishable from renal carcinoma, which is a malignant neoplasm. Prior studies have demonstrated that all these histological subtypes are different both genetically and biologically, and both their morphology and behavior are determined by distinctive molecular factors (Kovacs G., et al., J. Pathol., 1997, 183:131-133), but there is still no marker that has proven to be useful in clinical trials. Treatment of renal carcinoma is extremely difficult due to its capacity to spread without producing symptoms, due to its inherent resistance to conventional systemic chemotherapy and due to the inability of radiotherapy to reduce relapse levels after nephrectomy, even in patients with node involvement or tumors not completely resected (Kjaer M., et al., Int. J. Radiat. Oncol. Biol. Phys., 1987, 13:665-672). This makes it necessary to develop alternative therapeutic approaches to treat renal carcinomas with greater efficacy.

Transitional bladder carcinoma was the cause of over 1,120,000 deaths worldwide and over 3,400 in Spain in the year 2008 (GLOBOCAN). Bladder carcinomas are scaled up from G1 to G3 according to the WHO (World Health Organization) due to the decreasing state of cell differentiation and the increasing state of aggressiveness of the disease. With respect to the stage or invasiveness, transitional cell carcinomas (TCCs) of the bladder are classified as superficial with and without involvement of the lamina propria (Ta and T1), Infiltrating carcinoma of deep layers (T2 to T4) and the rather uncommon carcinoma in situ or tumor in situ (TIS). Low grade tumors (G1) are usually confined to the mucosa or Infiltrate surface layers (stage Ta and T1). New early diagnosis systems are necessary given that 80-90% of patients in stage T2 or higher are diagnosed de novo in that highly aggressive stage and not in earlier stages (de Vere White, R. W. and Stapp, E., Oncology, 1998, 12:1717-1723). The prognosis of patients with invasive transitional cell bladder carcinoma is poor; 50% of these patients in stage T2 or higher develops distant metastases during the 2 years after diagnosis, and 69% die during the 5 years after diagnosis, even when treatment is received. Alternative therapeutic approaches are necessary for treating muscle-invasive transitional cell bladder carcinoma with greater efficiency; alternative therapeutic approaches are also necessary for treating surface tumors more efficiently than surgery, or for complementing surgery, for the purpose of preventing relapse and the tumor progression to invasiveness.

Bronchioloalveolar carcinoma (BAC), also referred to as acinar cell carcinoma, is a lung adenocarcinoma subtype with characteristics that are well enough defined to be separated from the remaining subtypes. According to the World Health Organization (WHO) classification, BAC is an adenocarcinoma in which the cylindrical tumor cells grow on the walls of a pre-existing alveolus. A key characteristic of this neoplasm is the preservation of the underlying lung parenchyma. Despite the fact that many lung adenocarcinomas have areas with a bronchioloalveolar growth pattern, the diagnosis of BAC must be restricted to those neoplasms having only this pattern. BAC are fundamentally made up of two cell types, mucinous or non-mucinous cells, the latter being the most common; many non-mucinous BAC have a central fibrous region or focal point of distortion which can simulate invasion. In most studies, BAC comprise from 1% to 5% of lung adenocarcinomas, even though some recent studies increase the incidence to 15%. 50% usually present without prior symptomatology, such as peripheral solitary nodules, which are often an Incidental finding in a chest x-ray taken for other reasons. Some BAC grow slowly for several years without spreading, however others that Initially start as solitary nodules quickly develop metastasis and bilateral spread of the disease. Adenocarcinomas having a bronchioloalveolar pattern but showing a focal point stromal invasion must be called adenocarcinomas with a bronchioloalveolar pattern; they normally show a higher degree of atypia, mainly in the focal point of invasion. Bronchioloalveolar adenocarcinomas raise different differential diagnoses with both malignant and benign processes. They can be complicated; however, one of the most relevant is ordinary lung adenocarcinoma because the survival of BAC at 5 years is greater than the former. BAC can present vascular, lymphatic and pleural invasion, however, surgery can be curative between the half and two-thirds of the cases.

Breast cancer is the neoplasm with highest rate of incidence and mortality among women, hence early diagnosis and treatment are of vital importance. In recent years, with the introduction of genetics in medicine (especially in medical oncology), various discoveries have been made that affect the prognosis and treatment of breast cancer, which have led to re-classifying this pathology in terms of its genetic profile; the most significant discoveries are related to the epithelial component of these tumors, essentially epidermal growth factors (EGFr and Her-2), which have become therapeutic targets, just like estrogen and progesterone receptors (Perou C., Sorlie T., Eisen M., 2000, Nature, 406:747-752; Nielsen T., Hsu F., Jensen K., 2004, Clin. Cancer Res, 10:5367-5374). A series of immunohistochemical markers which are very useful for differentiating between benign and malignant lesions in cases in which conventional histochemical techniques are insufficient have further been developed. In the breast, there are benign sclerosing lesions, primarily sclerosing adenosis, and the radial scar which occasionally (due to their morphological pattern) raise difficulty in differential diagnosis with malignant infiltrating lesions (such as tubular carcinoma and infiltrating ductal carcinoma); this situation is even more complex in a large-gauge needle biopsy, because since there is no complete representation of the lesion, its contours cannot be seen, which is one of the keys for the differential diagnosis, especially when myoepithelial basal cells present in benign lesions and absent in malignant infiltrating lesions cannot be recognized with standard stains.

There are immunohistochemical markers (such as p63, $\alpha$-actin, smooth-muscle myosin heavy chain, calponin, s100 or CD10 protein) which stain myoepithelial cells of the breast ducts, aiding in differentiating between lesions of this type. Within these markers, $\alpha$-actin, smooth-muscle myosin heavy chain and calponin are very sensitive (89%) for myoepithelial basal cells; however, they are not specific for them, also staining vascular smooth-muscle cells and stromal myofibroblasts; similar problems are raised with s100 and CD10 (Lerwill, M. F., 2004, Am J Surg Path, 28:1076-1091). Werling et al. (Werling, R. W., Hwang, H., Yaziji, H., 2003, Am J Surg Path, 27:82-90) studied a series of cases corresponding to sclerosing adenosis, infiltrating ductal carcinoma, lobular carcinoma and ductal carcinoma in situ, analyzing the reactivity pattern of the p63, smooth-muscle myosin and calponin antibodies, demonstrating that they all stained myoepithelial cells of the benign and malignant non-infiltrating cases, in turn corroborating the positively of myosin and calponin in myofibroblasts and vascular smooth-muscle cells. In that work, p63 was the marker which presented the lowest cross-reactivity with stromal fibroblasts, without staining one of them, which showed its high sensitivity and specificity for staining myoepithelial cells in comparison with the remaining antibodies studied; nevertheless, it presented some drawbacks such as the occasionally discontinuous staining of myoepithelial cells (particularly in carcinomas in situ) and, also, focal positivity in up to 11% of cases of tumor cells. Meryem et. al. in turn described positivity with p63 in 13 cases of metaplastic breast carcinoma in a total of 14 cases (Meryem, Koker, M., Kleer, C. G., 2004, Am J Surg Path, 28:1506-1512). Currently p63 is one of the most widely used markers for the differential diagnosis between benign sclerosing and malignant Infiltrating lesions of the breast; however, to date there is no stromal marker which aids in differentiating between these lesions (Mattia Barbareschi, M., Pecciarini L., Cangi G., 2001, Am J Surg Path, 25:1054-1060). There is a need for specific markers in cases in which the conventional histochemical techniques are insufficient for differentiating between benign sclerosing and malignant infiltrating lesions of the breast.

Collagen is the main component of the extracellular matrix (ECM). The correct expression of the genes encoding the different types of collagen is necessary for the correct assembly of the ECM during embryonic development and for maintenance thereof in the adult organism. Collagen XI (COL11) is a type of collagen that has been studied very little but plays a fundamental role in regulating fibril networks in cartilaginous and non-cartilaginous matrices (Li, Y., et al., Cell, 1995, 80:423-430); these fiber networks are involved in different morphogenesis processes during embryonic development in vertebrates. Transcripts of collagen XI alpha 1 chain (COL11A1) have been found during fetal development fetal in cartilaginous tissues and also in other tissues such as bone, kidney, skin, muscle, tongue, intestine, liver, ear, brain and lung (Sandberg, J. M., et al., Biochem. J., 1993, 294:595-602; Yoshioka, H., et al., Dev. Dyn., 1995, 204: 41-47). The extracellular matrix also plays an important role in certain biological processes, such as cell differentiation, proliferation and migration; therefore, the dysregulation of the expression of genes encoding the proteins making them up is associated with carcinogenic and metastatic processes (Boudreau, N., and Bissell, M. J., Curr. Opin. Cell Biol., 1998, 10:640-646; Stracke, M. L., et al., In vivo, 1994, 8:49-58). In the particular case of COL11A1, stroma fibroblasts have been proven to have high col11a1 gene expression levels in sporadic colorectal carcinomas, whereas this gene is not expressed in healthy colon (Fischer, H., et al., Carcinogenesis, 2001, 22:875-878). Col11a1 gene expression has also been associated with pancreatic, breast, colon, lung, head and neck cancer (Kim, H. et al., BMC Medical Genomics, 2010, 3:51; Iacobuzio-Donahue, C., Am. J. Pathology, 2002, 160(4):1239-1249; Ellsworth, R. E., et al., Clin. Exp. Metastasis, 2009, 26: 205-13; Feng, Y., et al., Breast Cancer Res. Treat., 2007, 103(3):319-329; J. Gast. Liv. dis., 2008; Fischer, H., et al., BMC Cancer, 2001, 1:17-18; Fischer, H., et al., Carcinogenesis, 2001, 22:875-878; Suceveanu, A. I., et al., J. Gastrointestin. Liver Dis, 2009, 18(1):33-38; Chong, I W, et al., Oncol Rep, 2006, 16(5):981-988; Whan, K., Oncogene, 2002, 21:7598-7604; Oncol Rep, 2007; Schmalbach., C. E., et al., Arch. Otolaryngol. Head Neck Surg., 2004, 130(3):295-302) and bladder cancer (WO 2005/011619), and COL11A1 protein expression has been associated with pancreatic and colon cancer (Pilarsky, C., et al., J. Cel. Mol. Med., 2008, 12(6B):2823-35; Erkan, M., et al., Mol. Cancer, 2010, 9:88-103; Bowen, K. B., et al., J. Hist. Cyt., 2008, 56(3):275-283); but COL11A1 gene or protein expression has not been associated with other types of cancer (for example, kidney cancer), nor has COL11A1 protein expression been associated with breast, lung or head and neck cancer (differential gene expression does not necessarily interfere with the differential expression of the encoding protein).

Even though there are some markers for diagnosing different types of cancer and carcinomas, there is still a need to identify new markers which allow differentiating between different types of cancers and carcinomas the prognosis of which is very different, for example, between renal carcinomas and renal benign oncocytomas, between invasive transitional bladder carcinoma and superficial transitional bladder carcinomas, between infiltrating breast adenocarcinomas and sclerosing adenosis of the breast, and between pancreatic ductal adenocarcinomas, pancreatitis and carcinomas of the ampulla of Vater (ampullary tumors), which have a much better prognosis (21-61% of patients survive 5 years after diagnosis, versus 1-5% of ductal adenocarcinomas) (Takao S., et al., 1998, Am. J. Surg., 176:467-470; Warshaw A. L. and Fernández del Castillo, 1992, N. Eng. J. Med., 326:455-465).

In turn, collagens are components of the extracellular matrix that are synthesized as procollagens. These procollagens have a central triple-helical domain with a rod-shaped structure. This domain is flanked by N- and C-terminal non-collagenous propeptides; these propeptides are removed by specific peptidases as they are secreted out of the cell, where collagen trimers are assembled to form fibers. Procollagens V and XI α1 (proCOL5A1 and proCOL11A1, respectively) are encoded by the col5a1 and col11a1 genes, respectively. They have an approximately 75% amino acid sequence homology. The VAR sub-domain in the N-terminal propeptide has the greatest sequence variation between collagens. Nevertheless, the antibodies, some of which are commercially available, which have been used until now to study the COL11A1 protein expression, are polyclonal antibodies that have been developed against the central triple-helical domain, which is highly conserved between different collagens, so they do not specifically discriminate the COL11A1 expression of other collagens with a similar amino acid sequence, the expression of which does not necessarily vary during the tumor process, so it can lead to serious errors if they are used for the development of methods and products of diagnosis and prognosis of carcinomas. This is the case for example of the anti-Col11A1 antibody marketed by Calbiochem which has a cross-reactivity with COL9 (Collagen IX) protein, which is not differentially expressed in invasive carcinomas.

Using proCOL11A1 protein as a differential marker between infiltrating squamous cell head and neck carcinoma and benign head and neck pathologies (García-Ocaña et al., Poster "Immunohistochemical validation of procollagen COL11A1 as a desmoplastic tumor stroma marker", 18 Nov. 2010, III International Symposium of the IUOPA, Oviedo); as a differential marker between infiltrating ductal breast adenocarcinoma and sclerosing adenosis (Garcia Pravia et al., Abstract ESSR2009/218, "Anti-proCOL11A1, a new marker of infiltrating breast cancer", British J. Surgery, 2009, 96 (S5):11; García-Ocaña et al., Poster "Immunohistochemical validation of procollagen COL11A1 as a desmoplastic tumor stroma marker", 18 Nov. 2010, cited above); and as a differential marker between pancreatic ductal adenocarcinoma and chronic pancreatitis [García Pravia et al., Abstract ESSR2009/272, "ProCOL11A1 is an efficient marker of pancreatic cancer" British J. Surgery, 2009, 96 (S5):17; Garcia-Ocaña et al., Poster "Immunohistochemical validation of procollagen COL11A1 as a desmoplastic tumor stroma marker", 18 Nov. 2010, cited above)], has recently been described.

Nevertheless, the antibodies available until now do not allow specifically detecting proCOL11A1 protein, so the potential use of said protein as a differential marker between different pathologies, for example, between malignant and benign pathologies, cannot be reliably put into practice to their fullest extent Therefore, there is a need to develop antibodies which allow specifically detecting proCOL11A1. Said antibodies could be used to differentiate between different pathologies.

SUMMARY OF THE INVENTION

After thorough research investigation and using different techniques (DNA-chips and quantitative PCR to measure gene expression levels), the authors of the present invention have discovered that col11a1 gene expression:
  very high in renal carcinomas, but not in renal benign oncocytomas,
  very high in invasive transitional bladder carcinoma, but not in superficial transitional bladder carcinomas,
  very high in infiltrating breast adenocarcinomas, but not in sclerosing adenosis of the breast, and very high in pancreatic ductal adenocarcinomas, but not in pancreatitis, nor in carcinomas of the ampulla of Vater (ampullary tumors).

In turn, the authors of the present invention have developed polyclonal and monoclonal antibodies specifically against the VAR sub-domain in the proCOL11A1 N-terminal propeptide, which has the greatest sequence variation between collagens, thus generating antibodies specifically detecting proCOL11A1, discriminating it specifically from other collagens the expression of which does not vary during the tumor process. By using these proCOL11A1-specific antibodies in techniques of Western blot and/or immunohistochemical, the authors have discovered that the concentration of the proCOL11A1 protein:

- is increased in renal carcinomas, but not in renal benign oncocytomas;
- is increased in invasive transitional bladder carcinoma, but not in superficial transitional bladder carcinomas;
- is increased in infiltrating breast adenocarcinomas, but not in sclerosing adenosis of the breast;
- is increased in lung adenocarcinomas with a bronchoalveolar pattern, but not in bronchoalveolar adenocarcinomas;
- is increased in infiltrating squamous head and neck carcinomas, but not in other benign head and neck pathologies; is increased in colon adenocarcinomas, but not in other benign colon pathologies;
- is increased in pancreatic ductal adenocarcinomas, but not in pancreatitis nor in ampullary tumors; and
- is increased in peritoneal carcinomatosis.

This evidence makes said proCOL11A1-specific antibodies the ideal antibodies for the development of new in vitro methods and products for diagnosis and prognosis of said invasive carcinomas, and for the development of compounds specific for therapy of carcinomas, particularly renal carcinoma, invasive transitional bladder carcinoma, pancreatic ductal adenocarcinoma, infiltrating breast adenocarcinoma, colon adenocarcinoma, lung adenocarcinoma with a bronchoalveolar pattern, infiltrating squamous head and neck carcinomas and/or peritoneal carcinomatosis.

The present invention therefore provides methods and products for detecting in vitro the presence of an invasive carcinoma in an individual with high sensitivity and specificity, for determining or predicting the stage or the severity of said carcinoma in an individual, or for monitoring the effect of the therapy administered to an Individual who has said carcinoma, based on the detection and/or quantification of the proCol11A1 protein, col11a1 gene mRNA or the corresponding cDNA in a sample from said individual. The present invention likewise provides targets or tools for the search for, identification, development and evaluation of the efficacy of compounds for the therapy of an invasive carcinoma. The invention also provides proCOL11A1 protein expression and/or activity inhibitory agents for treatment of an invasive carcinoma. In a particular embodiment, said invasive carcinoma is selected from renal carcinoma, invasive transitional bladder carcinoma, colon adenocarcinoma, lung adenocarcinoma with a bronchoalveolar pattern, infiltrating squamous head and neck carcinomas, and peritoneal carcinomatosis.

Therefore, in one aspect the present invention relates to methods and products for detecting in vitro the presence of invasive carcinomas with high sensitivity and specificity, for determining or predicting the stage or the severity of said carcinomas in the individual, or for monitoring the effect of the therapy administered to an individual who has said carcinomas, based on col11a1 gene and/or proCOL11A1 protein expression. In one embodiment said invasive carcinomas are selected from renal carcinoma, invasive transitional bladder carcinoma, colon adenocarcinoma, lung adenocarcinoma with a bronchoalveolar pattern, Infiltrating squamous head and neck carcinomas, and peritoneal carcinomatosis.

In another aspect, the invention relates to methods and products f or searching for, identifying, developing and evaluating the efficacy of compounds for the therapy of invasive carcinomas based on the col11a1 gene and/or proCOL11A1 protein expression. In one embodiment said invasive carcinomas are selected from renal carcinoma, invasive transitional bladder carcinoma, pancreatic ductal adenocarcinoma, infiltrating breast adenocarcinoma, colon adenocarcinoma, lung adenocarcinoma with a bronchoalveolar pattern, infiltrating squamous head and neck carcinomas, and peritoneal carcinomatosis.

In another aspect, the invention relates to proCOL11A1 protein expression and/or activity inhibitors, or to proCOL11A1 protein expression induction inhibitors, or carcinogenic effect inhibitors, for use in the treatment of Invasive carcinomas. In a particular embodiment, said invasive carcinomas are selected from renal carcinoma, invasive transitional bladder carcinoma, pancreatic ductal adenocarcinoma, infiltrating breast adenocarcinoma, colon adenocarcinoma, lung adenocarcinoma with a bronchoalveolar pattern, infiltrating squamous head and neck carcinomas, and peritoneal carcinomatosis. In another particular embodiment, said inhibitor is the monoclonal antibody identified as 1E8.33 or a functional variant thereof.

In another aspect, the invention relates to a pharmaceutical composition comprising at least one proCOL11A1 protein expression and/or activity inhibitory agent, or a proCOL11A1 protein expression induction inhibitory agent, together with a pharmaceutically acceptable excipient.

These and other inventive aspects and particular embodiments will be described in further detail in the following description and in the attached claims.

BRIEF DESCRIPTION OF THE DRAWINGS

FIG. 1: Multalin v5.4.1 program output. Multiple alignment of the amino acid sequences of collagens type I-XXVII. The region of maximum homology is shown (around 2,400-2,500).

FIG. 2: Lalin v2.0 program output. Comparison of the amino acid sequences of collagens type XI alpha 1 (COL11A1) and V alpha 1 (COL5A1). The most divergent region, selected as a candidate for synthesizing the immunogen, is shaded

DETAILED DESCRIPTION OF THE INVENTION

Definitions

Figure 3:
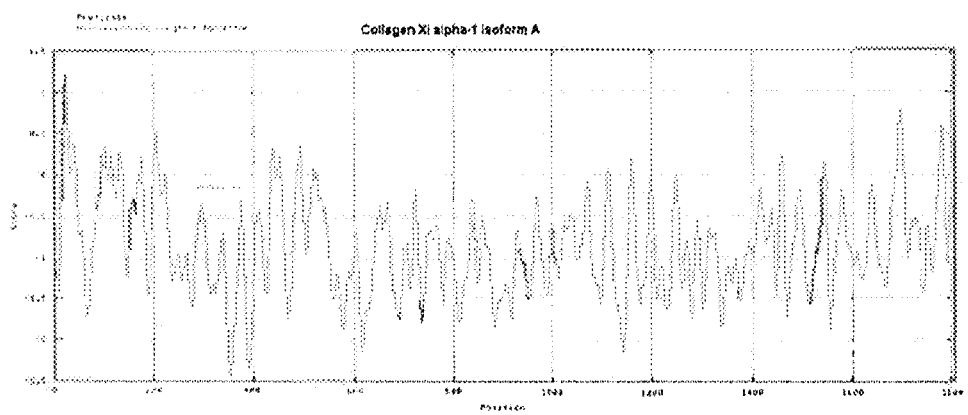
FIG. 3: COL11A1 protein hydrophobicity plot. The region used for designing the immunogen is shown in black (darker color).

The meaning of various terms and expressions as they are used within the context of the present invention is provided below to aid in understanding the present patent application.

The term "antagonist" refers to any molecule that inhibits the biological activity of the molecule being agonized. Examples of antagonist molecules include, among others, proteins, peptides, natural peptide sequence variations and small organic molecules (having a molecular weight less than 500 daltons).

The term "antibody" refers to a glycoprotein that exhibits specific binding activity for a particular protein, which is referred to as "antigen". The term "antibody" comprises whole monoclonal antibodies or polyclonal antibodies, or fragments thereof, and includes human antibodies, humanized antibodies and antibodies of a non-human origin. "Monoclonal antibodies" are homogenous, highly specific antibody populations directed against a single site or antigenic "determinant". "Polyclonal antibodies" include heterogeneous antibody populations directed against different antigenic determinants.

The term "cancer" or "carcinoma" refers to the disease that is characterized by the uncontrolled proliferation of abnormal cells capable of invading tissues adjacent and spreading to distant organs.

The term "head and neck cancer" or "head and neck carcinoma" refers to any malignant proliferative disorder of head or neck cells.

The term "colon cancer" or "colon adenocarcinoma" refers to any malignant proliferative disorder of colon cells.

The term "breast cancer" or "breast adenocarcinoma" refers to any malignant proliferative disorder of breast cells.

The term "pancreatic cancer" or "pancreatic adenocarcinoma" refers to any malignant proliferative disorder of pancreatic ductal cells.

The term "kidney cancer" or "renal carcinoma" refers to any malignant proliferative disorder of kidney cells.

The term "transitional bladder carcinoma" refers to any malignant proliferative disorder of bladder transitional epithelium cells.

The term "cDNA" refers to a complementary nucleotide sequence of a mRNA sequence.

The term "therapeutic target" refers to nucleotide or peptide sequences against which a drug or therapeutic compound can be designed and applied clinically.

The term "DNA" refers to deoxyribonucleic acid. A DNA sequence is a deoxyribonucleotide sequence.

As it is used herein, the term "epitope" refers to an antigenic determinant of a protein, which is the amino acid sequence of the protein which a specific antibody recognizes.

The term "specificity" refers to the detection of false positives (positive carcinoma diagnosis when the patient does not have carcinoma); 100% specificity means that there are no false positives.

As it is used herein, the term "solid phase" refers to a non-aqueous matrix to which the antibody can be bound. Examples of materials for solid phase include glass, polysaccharides, for example agarose, polyacrylamide, polystyrene, polyvinyl alcohol and silicones. Examples of solid phase forms are an assay plate well or a purification column.

The term "gene" refers to a molecular chain of deoxyribonucleotides that encodes a protein.

The term "col11a1" gene refers to the gene encoding a component of collagen XI referred to as "pro-α1(XI) chain" which combines with two other collagen chains (pro-α2(XI) and pro-α1(II)) to form a procollagen molecule (proCOL11A1) which is enzymatically processed in cells to form collagen XI fibers. Human col11a1 gene (also known as COLL6 or STL2), the reference gene sequence of which is NG_008033.1, occupies about 150 kilobases (kb), contains 68 exons, is located in chromosome 1 (1p21) between the base pairs 103342023 and 103574052, and encodes a protein with 1806 amino acids (according to the isoform) and 181 KDa containing a signal peptide (1-38 amino acids). This gene is conserved in humans, chimpanzees, cows, chickens, mice, rats and zebra fish. Mutations in this gene have been associated with Stickler II and Marshall syndromes. Polymorphisms of a nucleotide in this gene have been associated with a susceptibility to suffering lumber disc herniation. Several transcripts differing mainly in the transcription of exon 6 variants, for example, one of 7.2 kb encoding isoform A (NM_001854.3 (GI:98985806), NCBI database as of 21 Jul. 2011) with 1806 amino acids, another of 7.3 kb encoding isoform B (NM_080629.2 NCBI database as of 21 Jul. 2011) with 1806 amino acids (GI:98985810), another of 6.9 kb encoding isoform C (NM 080630.3 (GI:299523252), NCBI database as of 21 Jul. 2011) with 1690 amino acids (GI:299523253), another of 7.2 kb encoding isoform E (NM_001190709.1, NCBI database as of 1 Aug. 2011) with 1767 amino acids (GI: 299523257), etc., have been described. As it is used herein, the term "col11a1" does not refer only to the human gene but also to the orthologs of other species. Low and homogenous col11a1 gene expression is observed in all the analyzed tissues except in adipocytes, where it is considerably higher (BioGPS: Gene Atlas U133A). In cell lines, high expression is detected in UASMC cells (umbilical artery smooth muscle cells), HN_NP cells (neural precursors), HN_Os cells (osteoblasts), Panc-1 cells (pancreatic cancer cells), H522 cells (lung cancer cells) and U251 cells (glioma cells) (RefExA), A-204 cells (heart rhabdomyosarcoma cells), SAOS-2 cells (bone marrow osteosarcoma cells) and SK-MEL28 cells (skin cancer cells) (GeneCards).

The terms "individual" or "subject" refer to members of mammal species, and includes but is not limited to domestic animals, primates and humans; the subject is preferably a male or female human being of any age or race.

The term "mRNA" refers to messenger ribonucleic acid which is the fraction of the total RNA translated into proteins.

The expression "mRNA transcribed from" refers to the transcription of the gene (DNA) into mRNA as the first phase for the gene to be expressed and translated into a protein.

The expression "high levels" means that the levels measured in patients who have an invasive carcinoma, for example, renal carcinoma, invasive transitional bladder carcinoma or pancreatic ductal adenocarcinoma, etc., are greater than the levels measured in a control population of subjects who do not have a history of said invasive carcinoma.

The term "oligonucleotide primer" or "prime" refers to a nucleotide sequence which is complementary to a nucleotide sequence of the col11a1 gene. Each primer hybridizes with its target nucleotide sequence and acts like a DNA polymerization initiation site.

The terms "peptide" and "polypeptide" refer to a fragment protein. The terms "protein", "peptide" and "polypeptide" are used indistinctly in this description.

The term "proCOL11A1" refers to the collagen XI α1 chain, the processing of which leads to collagen XI α1 (COL11A1). proCOL11A1 has a central triple-helical domain with a rod-shaped structure, which is flanked by N- and C-terminal non-collagenous propeptides; these propeptides can be removed by specific peptidases as they are secreted out of the cell generating mature COL11A1, where collagen XI α1 chains are assembled with one another and with a2 and/or a3 chains to form collagen XI fibers. proCOL11A1 is encoded by the col11a1 gene. Several isoforms of human proCOL11A1 have been described, for example, isoform A [NM_001854.3 (GI:98985806), NCBI database as of 21 Jul. 2011] with 1806 amino acids, isoform B [NP_542196.2 (GI:98985810), NCBI database as of 21 Jul. 2011], isoform C [NM_080630.3 (GI:299523252), NCBI database as of 21 Jul. 2011], etc. As it is used herein, the term "proCOL11A1" does not refer only to human proCOL11A1 protein but also to the orthologs of other species.

The COL11A1 gene encodes a protein with 1806 amino acids, whose triple-helical region is between amino acids 529 and 1542. It has two domains that are not always present in the mature protein, the C-terminal domain (amino acids 1564-1806) and the N-terminal domain (amino acids 37-511). It forms part of collagen type XI, which is formed in cartilage by three chains forming a triple helix, α1(XI), α2(XI) (encoded by the COL11A2 gene) and α3(XI) (generated by excessive glycosylation of α1(II)) which can be substituted with α1(V). It is a component of the hyaline cartilage extracellular matrix, although it is also expressed in non-cartilaginous tissues and in tumor or virus-transformed cell lines, but in this case the three chains of collagen type XI are not always co-expressed, which could mean that the fibers have a chain composition different from that of cartilage, being homotrimeric or heterotypic in these locations (Yoshioka, H., J Biol Chem, 1990; 265(11):6423-6426; Lui, L C H, Biochem J, 1995; 311:511-516). It is thought to participate in the fibrillogenesis, regulating lateral growth of collagen II fibers, serving as a support for said fibers and being located within the formed fiber (Weis, M A., J Biol Chem 2010; 285(4):2580-2590). It is synthesized like procollagen, which is proteolytically processed after secretion, terminal N peptide (37-511) and terminal C peptide (1564-1806) being removed (Halsted, K C., Mod Pathol 2008; 21(10):1246-1254). A TSP (38-229) or Npp (amino propeptide) region, which is also found in 7 other types of collagens, in laminin and in thrombospondin, is contained in the peptide amino terminal (NTD), and t contains a BMP-1 processing site (Warner, L., J Biol Chem 2006; 281(51): 39507-39515, Gregory, K E., J Biol Chem 2000; 275(15): 11498-11506). In the case of α1(XI), this region is not always removed, sometimes being exposed on the surface of the collagen fibers for a long time (Fallahi, A., Prot Sci 2005; 14:1526-1537). This region is very similar to the LNS domains, having potential binding sites for heparin and calcium, which could mean cell-EM communication activity by binding to heparan sulfate proteoglycans (Warner, L., J Biol Chem 2006; 281(51):39507-39515, Fallahi, A., Prot Sci 2005; 14:1526-1537), even after being proteolyzed from the helical domain. Furthermore, the NTD covers a variable region which has different sequences and characteristics according to alternative splicing, combining exons 6-7-8 of the gene. These variants present tissue and temporal specificity (Warner, L., J Biol Chem 2006; 281(51):39507-39515) and at the same time affect Npp processing time.

The term "protein" refers to a molecular chain of amino acids with biological activity. The term Includes all forms of post-translation modifications, for example glycolysation, phosphorylation or acetylation.

The term "RNA" refers to ribonucleic acid. A RNA sequence is a sequence of ribonucleotides.

The term "nucleotide sequence" refers to a sequence of ribonucleotides (RNA) or deoxyribonucleotides (DNA).

The term "sensitivity" refers to the detection of false negatives (negative carcinoma diagnosis when the patient has carcinoma); 100% sensitivity means that there are no false negatives.

The term "probe" refers to a complementary nucleotide sequence of a nucleotide sequence derived from the col11a1 gene which can be used for detecting that nucleotide sequence derived from the col11a1 gene.

The term "tumor" refers to any abnormal tissue mass resulting from a benign (non-cancerous) or malignant (cancerous) neoplastic process.

Methods of Diagnosis/Prognosis

The present invention is based, among others, on the finding that both the gene expression of the col11a1 gene and the concentration of proCOL11A1 protein are increased in invasive carcinomas, particularly in renal carcinoma, Invasive transitional bladder carcinoma, pancreatic ductal adenocarcinoma, Infiltrating breast adenocarcinoma, colon adenocarcinoma, lung adenocarcinoma with a bronchoalveolar pattern, Infiltrating squamous head and neck carcinomas, and peritoneal carcinomatosis.

In one aspect, the invention relates to an in vitro method for detecting the presence of an invasive carcinoma in an individual, for determining or predicting the malignancy, the invasiveness, the stage and/or the severity of said carcinoma in an Individual, or for monitoring the effect of the therapy administered to an Individual who has said carcinoma, hereinafter "first method of the invention", comprising:
  a) the detection and/or quantification of proCOL11A1 protein in a sample from said individual; and
  b) the comparison of the presence and/or amount of said proCOL11A1 protein detected in said sample from said individual with the amount of proCOL11A1 protein detected in a control sample; and
  c) correlating the result obtained with the presence of an invasive carcinoma in an individual, the determination or prognosis of the malignancy, invasiveness, stage and/or severity of said invasive carcinoma in said individual, or the monitoring of the effect of the therapy administered to said individual who has said invasive carcinoma;
    on the condition that said invasive carcinoma is not infiltrating ductal breast adenocarcinoma or pancreatic ductal adenocarcinoma;
or alternatively
  a) the detection and/or quantification of col11a1 gene mRNA or of the corresponding cDNA in a sample from said individual; and
  b) the comparison of the amount of col11a1 gene mRNA or of the amount of the corresponding cDNA detected in said sample from said individual, with the amount of col11a1 gene mRNA or with the amount of the corresponding cDNA detected in a control sample; and
  c) correlating the result obtained with the presence of an invasive carcinoma in an individual, the determination or prognosis of the malignancy, invasiveness, stage and/or severity of said invasive carcinoma in said individual, or the monitoring of the effect of the therapy administered to said individual who has said invasive carcinoma;
    on the condition that said invasive carcinoma is not bladder carcinoma and that said carcinoma the invasiveness of which is to be known is not breast, colon, lung or ovarian cancer.

In a particular embodiment, said invasive carcinoma is selected from the group consisting of renal carcinoma, invasive transitional bladder carcinoma, colon adenocarcinoma, lung adenocarcinoma with a bronchoalveolar pattern, infiltrating squamous cell head and neck carcinoma and peritoneal carcinomatosis.

The first method of the present invention is a highly sensitive and specific method, and it is based on the fact that subjects or individuals diagnosed with invasive carcinoma have high levels of mRNA transcribed from col11a1 gene ("high col11a1 gene expression levels"), or high concentrations of the protein encoded by the col11a1 gene ("proCOL11A1 protein"), in absolute terms or in comparison with the corresponding levels in control samples, from subjects who do not have a clinical history of these carcinomas or from cultures of cells that do not express the col11a1 gene and/or do not express proCOL11A1 protein (negative controls).

To put the first method of the invention into practice, a sample, such as a biological sample, is obtained from the individual to be studied. Illustrative, non-limiting examples of said samples include different types of biological fluids, such as bile, gastric flow exudate, feces, urine, plasma, ascitic fluid, cerebrospinal fluid (CSF), peritoneal fluid, pleural fluid, synovial fluid, urine, saliva, blood, semen, serum, etc. These biological fluid samples can be obtained by any conventional method known by persons having ordinary skill in the art. Alternatively, said sample can also be an affected organ tissue sample, for example from the pancreas, bladder, kidney, etc., which can be obtained by any conventional method, for example by means of biopsy, cystoscopy, surgical resection, etc.

The samples to be analyzed can be obtained from subjects who have been previously diagnosed, or not diagnosed, with a specific type of invasive carcinoma, or also from a subject undergoing treatment, or who has been previously treated, for an invasive carcinoma, particularly for that specific type of carcinoma.

In a particular embodiment, the first method of the Invention comprises detecting and/or quantifying proCOL11A1 protein in a sample from said individual and comparing it with that of a control sample, wherein the detection or an increase in the amount (concentration or level) of said protein with respect to the amount of said proCOL11A1 protein in the control sample is indicative of invasive carcinoma.

The amount of proCOL11A1 protein present in said samples can be quantified by means of any conventional method which allows detecting and quantifying said protein in the samples to be analyzed. In this case, the first method of the invention includes performing an extraction step for the purpose of obtaining a protein extract containing said protein, which can be performed by means of conventional techniques (Chomczynski et al., Anal. Biochem., 1987, 162:156; Chomczynski P., Biotechniques, 1993, 15:532).

Virtually any conventional method can be used within the framework of the invention for detecting and quantifying the amount of proCOL11A1. By way of non-limiting illustration, the amount of said protein can be quantified by means of conventional methods, for example by means of using antibodies with the capacity to bind to proCOL11A1, and the complexes formed can subsequently be quantified. In a particular embodiment, the first method of the invention comprises contacting the protein extract from the sample with a composition comprising one or more specific antibodies against one or more epitopes of the proCOL11A1 protein, and subsequently detecting and/or quantifying the complexes formed by said antibodies and the COL11A1 protein.

There is a wide range of immunological assays available for detecting and/or quantifying the formation of specific antigen-antibody complexes; a number of competitive and non-competitive protein binding assays have previously been described, and a large number of these assays are commercially available. Therefore, proCOL11A1 protein can be quantified with antibodies such as, for example, whole monoclonal antibodies or polyclonal antibodies or recombinant fragments thereof, combibodies and Fab or scFv antibody fragments, specific against proCOL11A1 protein; these antibodies being human antibodies, humanized antibodies or antibodies of a non-human origin. There are antibodies binding to proCOL11A1 protein that are commercially available or have been described in the scientific literature; however, these antibodies are developed against the central triple-helical domain of COL11A1, which is highly conserved between different collagens, so they do not specifically discriminate the COL11A1 expression from other collagens having a similar amino acid sequence, the expression of which does not necessarily vary during the tumor process, so they can lead to serious errors if they are used for developing methods and products of diagnosis and prognosis of carcinomas. The authors of the present invention have developed polyclonal and monoclonal antibodies specifically against the VAR sub-domain in the proCOL11A1 N-terminal propeptide, which has the greatest sequence variation among collagens, thus generating antibodies specifically detecting proCOL11A1, discriminating it specifically from other collagens the expression of which does not vary during the tumor process. In a particular embodiment, said antibody is the monoclonal antibody identified as 1E8.33, the characteristics of which are described below.

The antibodies which are used in these assays can be labeled or not labeled; the antibodies that are not labeled can be used in agglutination assays; the antibodies that are labeled can be used in a wide range of assays. Marker molecules that can be used for labeling the antibodies include radionucleotides, enzymes, fluorophores, chemiluminescent reagents, enzyme substrates or cofactors, enzyme inhibitors, particles, dyes and derivatives.

There is a wide range of well-known assays that can be used in the present invention which use antibodies that are not labeled (primary antibody) and antibodies that are labeled (secondary antibody); these techniques include Western blot or immunoblot, ELISA (Enzyme-Linked Immunosorbent Assay), RIA (Radioimmunoassay), competitive EIA (Competitive Enzyme Immunoassay), DAS-ELISA (Double Antibody Sandwich-ELISA or), immunocytochemical and immunohistochemical techniques, multiplex detection techniques based on using protein microspheres, biochips or microarrays which include specific antibodies, or colloidal precipitation-based assays in formats such as dipsticks. Other ways of detecting and quantifying proCOL11A1 protein include affinity chromatography techniques, ligand binding assays or lectin binding assays.

The first method of the invention also comprises the step of comparing the presence and/or amount of said proCOL11A1 protein determined in the sample from the Individual object of study, with the amount of proCOL11 protein in the control sample (reference value). In a particular embodiment, the control sample is a sample from individuals who do not have a clinical history of invasive carcinoma, in which case the results obtained could have a diagnostic or predictive value of the malignancy, invasiveness, stage and/or severity of said carcinoma in the individual. In another particular embodiment, said control sample is a sample from the same individual but who is subjected to treatment, in which case the results obtained could have a value for monitoring the effect of the therapy administered to said individual who has said carcinoma. A positive control, for example a cell line that expresses proCOL11A1 protein, and/or a negative control, for example a cell line that does not express proCOL11A1 protein, can additionally be used if desired.

The first method of the invention additionally comprises the step of correlating the result obtained by comparing the presence and/or amount of proCOL11A1 protein determined in the sample from the Individual object of study, with the amount of proCOL11 protein in the control sample, with the presence of an invasive carcinoma in an individual, the determination or prognosis of the malignancy, invasiveness, stage and/or severity of said invasive carcinoma in said individual, or the monitoring of the effect of the therapy administered to said individual who has said invasive carcinoma.

According to the first method of the invention, the detection or an increase in the amount of said proCOL11A1 protein in the sample from said individual with respect to the level of said proCOL11A1 protein in said control sample is indicative of invasive carcinoma. Said information can also be used for determining or evaluating or predicting the malignancy, invasiveness, stage and/or severity of said invasive carcinoma in said individual; in this sense, the person skilled in the art, in view of the experience that he/she has acquired, will be able to correlate the amount of proCOL11A1 protein determined in the sample from the individual under study with the malignancy, Invasiveness, stage and/or severity of said invasive carcinoma in said individual. Likewise, when the control sample is a sample from the individual himself/herself diagnosed with invasive carcinoma, analyzed before or during the administration of a therapy for treating said invasive carcinoma, the Information relating to the detection or to the variation in the amount of said proCOL11A1 protein in the sample from said individual at a given time after the administration of said therapy, can serve for monitoring or evaluating the effect or efficacy of the therapy administered to said individual who has said invasive carcinoma and, if said therapy is not effective, evaluating the possibility of changing it.

This particular embodiment of the first method of the invention is useful for the detection of invasive carcinomas on the condition that said carcinoma is not infiltrating ductal breast adenocarcinoma or pancreatic ductal adenocarcinoma.

In another particular embodiment, the first method of the invention comprises quantifying the col11a1 gene expression level in a sample from said individual and comparing it with that of a control sample, wherein an increase in the expression level of said gene with respect to the level of said col11a1 gene in the control sample is indicative of an invasive carcinoma.

The expression level of a gene can be quantified by means of the quantification of the level of coding mRNA of said gene (col11a1), or alternatively of the level of the complementary DNA (cDNA) of said mRNA. In this case, the method of the invention includes performing an extraction step for the purpose of obtaining the total RNA, which can be performed by means of conventional techniques (Chomczynski et al., Anal. Biochem., 1987, 162:156; Chomczynski P., Biotechniques, 1993, 15:532; Molina, M. A., et al., Cancer Res., 1999, 59: 4356-4362).

Virtually any conventional method can be used within the framework of the invention for detecting and/or quantifying the levels of col11a1 gene mRNA or of the corresponding cDNA. By way of non-limiting illustration, the level of col11a1 gene mRNA can be quantified by means of using conventional methods, for example, methods comprising mRNA amplification and the quantification of the product of said mRNA amplification, such as electrophoresis and staining, or alternatively by means of Southern blot and using suitable probes, Northern blot and using probes specific for col11a1 gene mRNA or the corresponding cDNA, mapping with the S1 nuclease, RT-LCR, hybridization, microarrays, etc. In a particular embodiment, the amplification and quantification of the mRNA corresponding to the col11a1 gene is in turn performed by means of quantitative real time RT-PCR (Q-PCR). Similarly, the level of cDNA corresponding to said col11a1 gene mRNA can also be quantified by means of using conventional techniques; in this case, the method of the invention includes a step of synthesizing the corresponding cDNA by means of reverse transcription (RT) of the corresponding mRNA followed by amplification and quantification of the product of said cDNA amplification. In a particular embodiment, the amplification is carried out qualitatively or quantitatively by means of a polymerase chain reaction, for example, PCR or RT-PCR, using oligonucleotide primers that specifically amplify a region of the col11a1 gene; in a particular embodiment, said RT-PCR is carried out in the presence of the oligonucleotide primer pair the nucleotide sequences of which are shown in SEQ ID NO: 1 (5'-TGGTGATCAGAATCAGAAGTTCG-3') and SEQ ID NO: 2 (5'-AGGAGAGTTGAGAATTGGGAATC-3').

The first method of the invention also comprises the step of comparing the presence and/or amount of col11a1 gene mRNA or of the amount of the corresponding cDNA detected in said sample from said individual, with the amount of col11a1 gene mRNA or with the amount of the corresponding cDNA detected in a control sample. In a particular embodiment, the control sample is a sample from individuals who do not have a clinical history of invasive carcinoma, in which case the results obtained could have a diagnostic or predictive value of the malignancy, invasiveness, stage and/or severity of said carcinoma in the Individual. In another particular embodiment, said control sample is a sample from the same individual but who is subjected to treatment, in which case the results obtained could have value for monitoring the effect of the therapy administered to said individual who has said carcinoma. Additionally, a positive control, for example a cell line that expresses the col11a1 gene, and/or a negative control, for example a cell line that does not express the col11a1 gene, can be used if desired.

The first method of the invention additionally comprises the step of correlating the result obtained by comparing the presence and/or amount of col11a1 gene mRNA or of the amount of the corresponding cDNA detected in said sample from said individual, with the amount of col11a1 gene mRNA or with the amount of the corresponding cDNA detected in a control sample, with the presence of an invasive carcinoma in an individual, the determination or prognosis of the malignancy, invasiveness, stage and/or severity of said invasive carcinoma in said individual, or the monitoring of the effect of the therapy administered to said individual who has said invasive carcinoma.

According to the first method of the invention, the detection or an increase in the amount of said col11a1 gene mRNA or of the amount of the corresponding cDNA detected in said sample from said individual with respect to the amount of col11a1 gene mRNA or to the amount of the corresponding cDNA in said control sample is indicative of invasive carcinoma. Said information can also be used for determining or evaluating or predicting the malignancy, invasiveness, stage and/or severity of said invasive carcinoma in said individual; in this sense, the person skilled in the art, in view of the experience that he/she has acquired, will be able to correlate the amount of col11a1 gene mRNA or the amount of the corresponding cDNA determined in the sample from the individual under study with the malignancy, invasiveness, stage and/or severity of said invasive carcinoma in said individual. Likewise, when the control sample is a sample from the individual himself/herself diagnosed with invasive carcinoma, analyzed before or during the administration of a therapy for treating said invasive carcinoma, the information relating to the detection or to the variation in the amount of said col11a1 gene mRNA or of the corresponding cDNA in the sample from said individual at a given time after the administration of said therapy, can serve for monitoring or evaluating the effect or efficacy of the therapy administered to said individual who has said invasive carcinoma and, if said therapy is not effective, evaluating the possibility of changing it.

This particular embodiment of the first method of the Invention can be used for detecting an invasive carcinoma on the condition that said invasive carcinoma is not bladder carcinoma and that said carcinoma the invasiveness of which is to be known is not breast, colon, lung or ovarian cancer.

In another aspect, the invention relates to an in vitro method for differentially diagnosing an invasive transitional cell bladder carcinoma versus a superficial transitional cell bladder carcinoma in an individual, hereinafter "second method of the invention", comprising:

a) the detection and/or quantification of proCOL11A1 protein in a sample from said individual, and
  b) the comparison of the presence and/or amount of said proCOL11A1 protein detected in said sample from said individual with the amount of proCOL11A1 protein detected in a control sample,
    wherein the detection or an increase in the amount of proCOL11A1 protein in said sample from said individual with respect to the level of proCOL11A protein in said control sample is indicative of invasive transitional cell bladder carcinoma;
  or alternatively
  a) the detection and/or quantification of col11a1 gene mRNA or of the corresponding cDNA in a sample from said individual, and
  b) the comparison of the amount of col11a1 gene mRNA or of the amount of the corresponding cDNA detected in said sample from said individual, with the amount of col11a1 gene mRNA or with the amount of the corresponding cDNA detected in a control sample,
    wherein an increase in the amount of col11a1 gene mRNA or in the amount of the corresponding cDNA in said sample from said individual with respect to the amount of col11a1 gene mRNA or to the amount of the corresponding cDNA in said control sample is indicative of invasive transitional cell bladder carcinoma.

The characteristics of the sample from the individual, obtaining and preparing said sample for obtaining a protein extract used for detecting and/or quantifying proCOL11A1 protein, or for obtaining a nucleic acid extract (e.g., total RNA, etc.) used for detecting and/or quantifying col11a1 gene mRNA or the corresponding cDNA have already been mentioned in relation to the first method of the invention and are herein incorporated by reference.

In a particular embodiment, the sample from the individual under study is a neoplastic bladder tissue sample obtained by conventional methods, for example by means of biopsy.

Likewise, the methods for detecting and/or quantifying proCOL11A1 protein, and for detecting and/or quantifying col11a1 gene mRNA or the corresponding cDNA have already been mentioned in relation to the first method of the invention and are herein incorporated by reference.

In a particular embodiment of the second method of the invention, proCOL11A1 protein is detected and/or quantified by means of an immunoassay based on using an antibody that recognizes proCOL11A1 protein; in a specific embodiment, said antibody is the monoclonal antibody identified as 1E8.33 in this description, the characteristics of which are described below.

In another particular embodiment of the second method of the invention, col11a1 gene mRNA or the corresponding cDNA is detected and/or quantified by means of enzyme amplification and/or hybridization techniques. In a more particular embodiment, col11a1 gene mRNA or the corresponding cDNA is detected and/or quantified by means of a PCR technique, for example, real time RT-PCR, by means of using suitable oligonucleotide primers that specifically amplify a region of the col11a1 gene; in a specific embodiment said oligonucleotide primers are the oligonucleotide primers the nucleotide sequences of which are shown in SEQ ID NO: 1 and SEQ ID NO: 2. In a particular embodiment of the second method of the invention, the sample from the individual under study is a neoplastic bladder tissue sample, and the col11a1 gene expression level is analyzed in said sample from total RNA (Example 3).

In a particular embodiment, the control sample is a sample from one or from a pool of healthy individuals or individuals who are reliably diagnosed as individuals suffering superficial transitional cell bladder carcinoma. Likewise, a positive control, for example a cell line that expresses the col11a1 gene, and/or a negative control, for example a cell line that does not express the col11a1 gene, can be used if desired.

According to the second method of the invention, after comparing the results obtained in the sample from the individual under study with the results of the control sample (or reference value), the detection or an increase in the level of col11a1 protein in the sample from said individual with respect to the level of proCOL11A protein in the control sample is indicative of invasive transitional cell bladder carcinoma, or alternatively an increase in the amount of col11a1 gene mRNA or in the amount of the corresponding cDNA in said sample from said individual with respect to the amount of col11a1 gene mRNA or to the amount of the corresponding cDNA in said control sample is indicative of invasive transitional cell bladder carcinoma.

In another aspect, the invention relates to an in vitro method for differentially diagnosing renal carcinoma versus oncocytoma in an individual, hereinafter "third method of the invention", comprising:

a) the detection and/or quantification of proCOL11A1 protein in a sample from said individual, and b) the comparison of the presence and/or amount of said proCOL11A1 protein detected in said sample from said individual with the amount of proCOL11A1 protein detected in a control sample, wherein the detection or an increase in the amount of proCOL11A1 protein in said sample from said individual with respect to the level of proCOL11A protein in said control sample is indicative of renal carcinoma;

or alternatively a) the detection and/or quantification of col11a1 gene mRNA or of the corresponding cDNA in a sample from said individual, and b) the comparison of the amount of col11a1 gene mRNA or of the amount of the corresponding cDNA detected in said sample from said individual, with the amount of col11a1 gene mRNA or with the amount of the corresponding cDNA detected in a control sample, wherein an increase in the amount of col11a1 gene mRNA or in the amount of the corresponding cDNA in said sample from said individual with respect to the amount of col11a1 gene mRNA or to the amount of the corresponding cDNA in said control sample is indicative of renal carcinoma.

The characteristics of the sample from the individual, obtaining and preparing said sample for obtaining a protein extract used for detecting and/or quantifying proCOL11A1 protein, or for obtaining a nucleic acid extract (e.g., total RNA, etc.) used for detecting and/or quantifying col11a1 gene mRNA or the corresponding cDNA have already been mentioned in relation to the first method of the invention and are herein incorporated by reference.

In a particular embodiment, the sample from the individual under study is a neoplastic kidney tissue sample obtained by conventional methods, for example by means of biopsy.

Likewise, the methods for detecting and/or quantifying proCOL11A1 protein, and for detecting and/or quantifying col11a1 gene mRNA or the corresponding cDNA have already been mentioned in relation to the first method of the invention and are herein incorporated by reference.

In a particular embodiment of the third method of the invention, proCOL11A1 protein is detected and/or quantified by means of an immunoassay based on using an antibody that recognizes proCOL11A1 protein; in a specific embodiment, said antibody is the monoclonal antibody identified as 1E8.33 in this description, the characteristics of which are described below.

In another particular embodiment of the third method of the invention, col11a1 gene mRNA or the corresponding cDNA is detected and/or quantified by means of enzyme amplification and/or hybridization techniques. In a more particular embodiment, col11a1 gene mRNA or the corresponding cDNA is detected and/or quantified by means of a PCR technique, for example, real time RT-PCR, by means of using suitable oligonucleotide primers that specifically amplify a region of the col11a1 gene; in a specific embodiment said oligonucleotide primers are the oligonucleotide primers the nucleotide sequences of which are shown in SEQ ID NO: 1 and SEQ ID NO: 2.

In a particular embodiment of the third method of the invention, the sample from the Individual under study is a neoplastic kidney tissue sample, and the col11a1 gene expression level is analyzed in said sample from total RNA (Example 1).

In a particular embodiment, the control sample is a sample from one or from a pool of healthy individuals or Individuals who are reliably diagnosed as individuals suffering oncocytoma. Likewise, a positive control, for example a cell line that expresses the col11a1 gene, and/or a negative control, for example a cell line that does not express the col11a1 gene, can be used if desired.

According to the third method of the invention, after comparing the results obtained in the sample from the individual under study with the results of the control sample (or reference value), the detection or an increase in the level of proCOL11A1 protein in the sample from said individual with respect to the level of proCOL11A protein in the control sample is indicative of renal carcinoma, or alternatively an increase in the amount of col11a1 gene mRNA or in the amount of the corresponding cDNA in said sample from said individual with respect to the amount of col11a1 gene mRNA or to the amount of the corresponding cDNA in said control sample is indicative of renal carcinoma.

In another aspect, the invention relates to an in vitro method for differentially diagnosing lung adenocarcinoma with a bronchioloalveolar pattern versus bronchoalveolar adenocarcinoma in an individual, "fourth method of the invention", comprising:
   a) the detection and/or quantification of proCOL11A1 protein in a sample from said individual, and
   b) the comparison of the presence and/or amount of said proCOL11A1 protein detected in said sample from said individual with the amount of proCOL11A1 protein detected in a control sample,
      wherein the detection or an increase in the level of proCOL11A1 protein in said sample from said individual with respect to the level of proCOL11A protein in said control sample is indicative of lung adenocarcinoma with a bronchioloalveolar pattern;
or alternatively
   a) the detection and/or quantification of col11a1 gene mRNA or of the corresponding cDNA in a sample from said individual, and
   b) the comparison of the amount of col11a1 gene mRNA or of the amount of the corresponding cDNA detected in said sample from said individual, with the amount of col1a1 gene mRNA or with the amount of the corresponding cDNA detected in a control sample,
      wherein an increase in the amount of col11a1 gene mRNA or in the amount of the corresponding cDNA in said sample from said individual with respect to the amount of col11a1 gene mRNA or to the amount of the corresponding cDNA in said control sample is indicative of lung adenocarcinoma with a bronchioloalveolar pattern.

The characteristics of the sample from the individual, obtaining and preparing said sample for obtaining a protein extract used for detecting and/or quantifying proCOL11A1 protein, or for obtaining a nucleic acid extract (e.g., total RNA, etc.) used for detecting and/or quantifying col11a1 gene mRNA or the corresponding cDNA have already been mentioned in relation to the first method of the invention and are herein incorporated by reference.

In a particular embodiment, the sample from the Individual under study is a neoplastic lung tissue sample obtained by conventional methods, for example by means of biopsy.

Likewise, the methods for detecting and/or quantifying proCOL11A1 protein, and for detecting and/or quantifying col11a1 gene mRNA or the corresponding cDNA have already been mentioned in relation to the first method of the invention and are herein incorporated by reference.

In a particular embodiment of the fourth method of the invention, proCOL11A1 protein is detected and/or quantified by means of an Immunoassay based on using an antibody that recognizes proCOL11A1 protein; In a specific embodiment, said antibody is the monoclonal antibody identified as 1E8.33 In this description, the characteristics of which are described below.

In another particular embodiment of the fourth method of the invention, col11a1 gene mRNA or the corresponding cDNA is detected and/or quantified by means of enzyme amplification and/or hybridization techniques. In a more particular embodiment, col11a1 gene mRNA or the corresponding cDNA is detected and/or quantified by means of a PCR technique, for example, real time RT-PCR, by means of using suitable oligonucleotide primers that specifically amplify a region of the col11a1 gene; in a specific embodiment said oligonucleotide primers are the oligonucleotide primers the nucleotide sequences of which are shown in SEQ ID NO: 1 and SEQ ID NO: 2.

In a particular embodiment of the fourth method of the invention, the sample from the individual under study is a neoplastic lung tissue sample and proCOL11A1 protein expression is analyzed by means of immunohistochemistry using the monoclonal antibody identified as 1E8.33 in this description (Example 8.4).

In a particular embodiment, the control sample is a sample from one or from a pool of healthy individuals or individuals who are reliably diagnosed as individuals suffering bronchoalveolar adenocarcinoma. Likewise, a positive control, for example a cell line that expresses the col11a1 gene, and/or a negative control, for example a cell line that does not express the col11a1 gene, can be used if desired.

According to the fourth method of the invention, after comparing the results obtained in the sample from the individual under study with the results of the control sample (or reference value), the detection or an Increase in the level of proCOL11A1 protein in the sample from said individual with respect to the level of proCOL11A protein in the control sample is indicative of lung adenocarcinoma with a bronchioloalveolar pattern, or alternatively an increase in the amount of col11a1 gene mRNA or in the amount of the corresponding cDNA in said sample from said individual with respect to the amount of col11a1 gene mRNA or to the amount of the corresponding cDNA in said control sample is indicative of lung adenocarcinoma with a bronchioloalveolar pattern.

In another aspect, the invention relates to an in vitro method for differentially diagnosing colon adenocarcinoma versus benign fibrosis, hereinafter "fifth method of the invention", comprising:
   a) the detection and/or quantification of proCOL11A1 protein in a sample from said individual, and
   b) the comparison of the presence and/or amount of said proCOL11A1 protein detected in said sample from said individual with the amount of proCOL11A1 protein detected in a control sample,
      wherein the detection or an increase in the amount of proCOL11A1 protein in said sample from said individual with respect to the level of proCOL11A protein in said control sample is indicative of colon adenocarcinoma;
   or alternatively
   a) the detection and/or quantification of col11a1 gene mRNA or of the corresponding cDNA in a sample from said individual, and
   b) the comparison of the amount of col11a1 gene mRNA or of the amount of the corresponding cDNA detected in said sample from said individual, with the amount of col11a1 gene mRNA or with the amount of the corresponding cDNA detected in a control sample, wherein an increase in the amount of col11a1 gene mRNA or in the amount of the corresponding cDNA in said sample from said individual with respect to the amount of col11a1 gene mRNA or to the amount of the corresponding cDNA in said control sample is indicative of colon adenocarcinoma.

The characteristics of the sample from the individual, obtaining and preparing said sample for obtaining a protein extract used for detecting and/or quantifying proCOL11A1 protein, or for obtaining a nucleic acid extract (e.g., total RNA, etc.) used for detecting and/or quantifying col11a1 gene mRNA or the corresponding cDNA have already been mentioned in relation to the first method of the invention and are herein incorporated by reference.

In a particular embodiment, the sample from the individual under study is a neoplastic colon tissue sample obtained by conventional methods, for example by means of biopsy.

Likewise, the methods for detecting and/or quantifying proCOL11A1 protein, and for detecting and/or quantifying col11a1 gene mRNA or the corresponding cDNA have already been mentioned in relation to the first method of the invention and are herein incorporated by reference.

In a particular embodiment of the fifth method of the invention, proCOL11A1 protein is detected and/or quantified by means of an immunoassay based on using an antibody that recognizes proCOL11A1 protein; in a specific embodiment, said antibody is the monoclonal antibody identified as 1E8.33 in this description, the characteristics of which are described below.

In another particular embodiment of the fifth method of the invention, col11a1 gene mRNA or the corresponding cDNA is detected and/or quantified by means of enzyme amplification and/or hybridization techniques. In a more particular embodiment, col11a1 gene mRNA or the corresponding cDNA is detected and/or quantified by means of a PCR technique, for example, real time RT-PCR, by means of using suitable oligonucleotide primers that specifically amplify a region of the col11a1 gene; in a specific embodiment said oligonucleotide primers are the oligonucleotide primers the nucleotide sequences of which are shown in SEQ ID NO: 1 and SEQ ID NO: 2.

In a particular embodiment of the fifth method of the invention, the sample from the individual under study is a neoplastic colon tissue sample and proCOL11A1 protein expression is analyzed by means of immunohistochemistry using the monoclonal antibody identified as 1E8.33 in this description (Example 8.5).

In a particular embodiment, the control sample is a sample from one or from a pool of healthy individuals or individuals who are reliably diagnosed as individuals suffering benign fibrosis. Likewise, a positive control, for example a cell line that expresses the col11a1 gene, and/or a negative control, for example a cell line that does not express the col11a1 gene, can be used if desired.

According to the fifth method of the invention, after comparing the results obtained in the sample from the individual under study with the results of the control sample (or reference value), the detection or an increase in the level of proCOL11A1 protein in the sample from said individual with respect to the level of proCOL11A protein in the control sample is indicative of colon adenocarcinoma, or alternatively an increase in the amount of col11a1 gene mRNA or in the amount of the corresponding cDNA in said sample from said individual with respect to the amount of col11a1 gene mRNA or to the amount of the corresponding cDNA in said control sample is indicative of colon adenocarcinoma.

In another aspect, the invention relates to an in vitro method for differentially diagnosing infiltrating squamous cell head and neck carcinoma versus a benign head and neck pathology in an individual, hereinafter "sixth method of the invention", comprising:

a) the detection and/or quantification of proCOL11A1 protein in a sample from said individual, and b) the comparison of the presence and/or amount of said proCOL11A1 protein detected in said sample from said individual with the amount of proCOL11A1 protein detected in a control sample, wherein the detection or an increase in the amount of proCOL11A1 protein in said sample from said individual with respect to the level of proCOL11A protein in said control sample is indicative of Infiltrating squamous cell head and neck carcinoma;

or alternatively a) the detection and/or quantification of col11a1 gene mRNA or of the corresponding cDNA in a sample from said individual, and b) the comparison of the amount of col11a1 gene mRNA or of the amount of the corresponding cDNA detected in said sample from said individual, with the amount of col11a1 gene mRNA or with the amount of the corresponding cDNA detected in a control sample, wherein an increase in the amount of col11a1 gene mRNA or in the amount of the corresponding cDNA in said sample from said individual with respect to the amount of col11a1 gene mRNA or to the amount of the corresponding cDNA in said control sample is indicative of Infiltrating squamous cell head and neck carcinoma.

The characteristics of the sample from the individual, obtaining and preparing said sample for obtaining a protein extract used for detecting and/or quantifying proCOL11A1 protein, or for obtaining a nucleic acid extract (e.g., total RNA, etc.) used for detecting and/or quantifying col11a1 gene mRNA or the corresponding cDNA have already been mentioned in relation to the first method of the invention and are herein incorporated by reference.

In a particular embodiment, the sample from the individual under study is a neoplastic head and/or neck tissue sample obtained by conventional methods, for example by means of biopsy.

Likewise, the methods for detecting and/or quantifying proCOL11A1 protein, and for detecting and/or quantifying col11a1 gene mRNA or the corresponding cDNA have already been mentioned in relation to the first method of the invention and are herein incorporated by reference.

In a particular embodiment of the sixth method of the invention, proCOL11A1 protein is detected and/or quantified by means of an immunoassay based on using an antibody that recognizes proCOL11A1 protein; in a specific embodiment, said antibody is the monoclonal antibody identified as 1E8.33 in this description, the characteristics of which are described below.

In another particular embodiment of the sixth method of the invention, col11a1 gene mRNA or the corresponding cDNA is detected and/or quantified by means of enzyme amplification and/or hybridization techniques. In a more particular embodiment, col11a1 gene mRNA or the corresponding cDNA is detected and/or quantified by means of a PCR technique, for example, real time RT-PCR, by means of using suitable oligonucleotide primers that specifically amplify a region of the col11a1 gene; in a specific embodiment said oligonucleotide primers are the oligonucleotide primers the nucleotide sequences of which are shown in SEQ ID NO: I and SEQ ID NO: 2.

In a particular embodiment of the sixth method of the invention, the sample from the individual under study is a neoplastic head and/or neck tissue sample and proCOL11A1 protein expression is analyzed by means of immunohistochemistry using the monoclonal antibody identified as 1E8.33 in this description (Example 8.6).

In a particular embodiment, the control sample is a sample from one or from a pool of healthy individuals or individuals who are reliably diagnosed as individuals suffering a benign head and neck pathology such as Inflammation, ulcer, hyperplasia, leukoplakia, erosive lichen or fibrosis. Likewise, a positive control, for example a cell line that expresses the col11a1 gene, and/or a negative control, for example a cell line that does not express the col11a1 gene, can be used if desired.

According to the sixth method of the invention, after comparing the results obtained in the sample from the individual under study with the results of the control sample (or reference value), the detection or an increase in the level of proCOL11A1 protein in the sample from said individual with respect to the level of proCOL11A protein in the control sample is indicative of infiltrating squamous cell head and neck carcinoma, or alternatively an increase in the amount of col11a1 gene mRNA or in the amount of the corresponding cDNA in said sample from said individual with respect to the amount of col11a1 gene mRNA or to the amount of the corresponding cDNA in said control sample is indicative of infiltrating squamous cell head and neck carcinoma.

In another aspect, the invention relates to an in vitro method for differentially diagnosing a pancreatic ductal adenocarcinoma versus ampullary tumor in an Individual, hereinafter "seventh method of the invention", comprising:
  a) the detection and/or quantification of proCOL11A1 protein in a sample from said individual, and
  b) the comparison of the presence and/or amount of said proCOL11A1 protein detected in said sample from said individual with the amount of proCOL11A1 protein detected in a control sample,
     wherein the detection or an increase in the amount of proCOL11A1 protein in said sample from said individual with respect to the level of proCOL11A protein in said control sample is indicative of pancreatic ductal adenocarcinoma;
     or alternatively
  a) the detection and/or quantification of col11a1 gene mRNA or of the corresponding cDNA in a sample from said individual, and
  b) the comparison of the amount of col11a1 gene mRNA or of the amount of the corresponding cDNA detected in said sample from said individual, with the amount of col11a1 gene mRNA or with the amount of the corresponding cDNA detected in a control sample,
     wherein an increase in the amount of col11a1 gene mRNA or in the amount of the corresponding cDNA in said sample from said individual with respect to the amount of col11a1 gene mRNA or to the amount of the corresponding cDNA in said control sample is indicative of pancreatic ductal adenocarcinoma.

The characteristics of the sample from the individual, obtaining and preparing said sample for obtaining a protein extract used for detecting and/or quantifying proCOL11A1 protein, or for obtaining a nucleic acid extract (e.g., total RNA, etc.) used for detecting and/or quantifying col11a1 gene mRNA or the corresponding cDNA have already been mentioned in relation to the first method of the invention and are herein incorporated by reference.

In a particular embodiment, the sample from the individual under study is a neoplastic pancreatic tissue sample obtained by conventional methods, for example by means of biopsy.

Likewise, the methods for detecting and/or quantifying proCOL11A1 protein, and for detecting and/or quantifying col11a1 gene mRNA or the corresponding cDNA have already been mentioned in relation to the first method of the invention and are herein incorporated by reference.

In a particular embodiment of the seventh method of the invention, proCOL11A1 protein is detected and/or quantified by means of an immunoassay based on using an antibody that recognizes proCOL11A1 protein; in a specific embodiment, said antibody is the monoclonal antibody identified as 1E8.33 in this description, the characteristics of which are described below.

In another particular embodiment of the seventh method of the invention, col11a1 gene mRNA or the corresponding cDNA is detected and/or quantified by means of enzyme amplification and/or hybridization techniques. In a more particular embodiment, col11a1 gene mRNA or the corresponding cDNA is detected and/or quantified by means of a PCR technique, for example, real time RT-PCR, by means of using suitable oligonucleotide primers that specifically amplify a region of the col11a1 gene; in a specific embodiment said oligonucleotide primers are the oligonucleotide primers the nucleotide sequences of which are shown in SEQ ID NO: 1 and SEQ ID NO: 2.

In a particular embodiment of the seventh method of the invention, the sample from the individual under study is a neoplastic pancreatic tissue sample and the col11a1 gene expression level is analyzed in said sample from total RNA (Example 2), for example by means of real time RT-PCR (Example 4).

In another particular embodiment of the seventh method of the invention, the sample from the individual under study is a neoplastic pancreatic tissue sample and proCOL11A1 expression protein is analyzed by means of immunohistochemistry using the monoclonal antibody identified as 1E8.33 in this description (Examples 6 and 7).

In a particular embodiment, the control sample is a sample from one or from a pool of healthy individuals or individuals who are reliably diagnosed as individuals suffering chronic pancreatitis or ampullary tumor. Likewise, a positive control, for example a cell line that expresses the col11a1 gene, and/or a negative control, for example a cell line that does not express the col11a1 gene, can be used if desired.

According to the seventh method of the invention, after comparing the results obtained in the sample from the individual under study with the results of the control sample (or reference value), the detection or an increase in the level of col11a1 protein in the sample from said individual with respect to the level of proCOL11A protein in the control sample is indicative of pancreatic ductal adenocarcinoma, or alternatively an increase in the amount of col11a1 gene mRNA or in the amount of the corresponding cDNA in said sample from said individual with respect to the amount of col11a1 gene mRNA or to the amount of the corresponding cDNA in said control sample is indicative of pancreatic ductal adenocarcinoma.

Screening Methods

In another aspect, the invention relates to an in vitro method for identifying and evaluating the efficacy of a compound for therapy of an invasive carcinoma, comprising:
a) contacting a tumor cell culture with the candidate compound under the conditions and for the time suitable for allowing them to interact,
b) detecting and quantifying col11a1 gene or proCOL11A1 protein expression levels, and
c) comparing said expression levels with said col11a1 gene or said proCOL11A1 protein expression levels in a tumor cell control culture not treated with said candidate compound.

The tumor cells can be from any invasive carcinoma; nevertheless, in a particular embodiment, said invasive carcinoma is selected from renal carcinoma, invasive transitional bladder carcinoma, pancreatic ductal adenocarcinoma, Infiltrating breast adenocarcinoma, colon adenocarcinoma, lung adenocarcinoma with a bronchoalveolar pattern, Infiltrating squamous cell head and neck carcinoma and peritoneal carcinomatosis.

The col11a1 gene or proCOL11A1 protein expression levels are quantified similarly to that indicated in relation to the first method of the invention, incorporated herein by reference.

When a compound reduces the col11a1 gene or proCOL11A1 protein expression levels, or reverses the effects of the high expression of said gene, preferably by reducing cell proliferation levels, that compound becomes a candidate for therapy of Invasive carcinoma.

In a particular embodiment, said invasive carcinoma is selected from renal carcinoma, invasive transitional bladder carcinoma, pancreatic ductal adenocarcinoma, Infiltrating breast adenocarcinoma, colon adenocarcinoma, lung adenocarcinoma with a bronchoalveolar pattern, infiltrating squamous cell head and neck carcinoma and peritoneal carcinomatosis.

ProCOL11 A1 Inhibitors and Applications Thereof

In another aspect, the invention relates to a proCOL11A1 inhibitor. In the context of the present invention, "proCOL11A1 inhibitor" is understood as a compound inhibiting or reducing proCOL11A1 protein expression and/or activity, or inhibiting the carcinogenic effects of proCOL11A1 protein expression induction, and includes any compound that is capable of preventing or blocking col11a1 gene transcription and/or translation (i.e., preventing or blocking said gene expression), or that is capable of preventing the protein encoded by said proCOL11A1 gene from performing its function (activity); i.e., said term "proCOL11A1 inhibitor" Includes compounds acting either at the RNA level (e.g., antisense oligonucleotides ("antisense"), shRNA, siRNA, etc.), or at the protein level (e.g., antibodies, peptides, small organic compounds or small molecules, etc.).

By way of non-limiting illustration, proCOL11A1 inhibitors include gol11a1 gene expression inhibitory agents suitable for use in the present invention, and include, for example, antisense oligonucleotides specific for the col11a1 gene, specific microRNAs, catalytic RNAs or specific ribozymes, specific interfering RNAs (siRNAs), RNAs with decoy activity, i.e., with the capacity to bind specifically to a (generally protein) factor important for gene expression, such that expression of the gene of interest, in this case col11a1, is inhibited, etc. Other illustrative, non-limiting examples of proCOL11A1 inhibitors include compounds or substances capable of preventing proCOL11A1 protein from performing its function or activity, for example, proCOL11A1 inhibitor peptides, antibodies directed specifically against proCOL11A1 epitopes, as well as non-peptide chemical compounds that reduce or inhibit proCOL11A1 protein function.

ProCOL11A1 inhibitors can be identified and evaluated according to the teachings of the present invention; particularly the previously described method of screening, can be used. Nevertheless, methods of another type suitable for identifying and evaluating proCOL11A1 inhibitors can be used.

Compounds causing the reduction of levels of col11a1 mRNA can be identified using standard assays for determining mRNA expression levels, such as those mentioned in relation to the first method of the invention. Compounds causing the reduction of the levels of proCOL11A1 protein can be identified using standard assays for the determination of protein expression levels such as those mentioned in relation to the first method of the invention.

Illustrative, non-limiting examples of proCOL11A1 inhibitors include:
a) specific antibodies against one or more epitopes present in the proCOL11A1 protein, preferably human or humanized monoclonal antibodies, or functional fragments thereof, single-chain antibodies, anti-idiotype antibodies, etc.; in a particular embodiment, said antibody is 1E8.33 monoclonal antibody, a variant thereof, the characteristics of which are mentioned below;
b) cytotoxic agents, such as toxins, molecules with radioactive atoms, or chemotherapeutic agents, which include in a non-limiting manner small organic and inorganic molecules, peptides, phosphopeptides, antisense molecules, ribozymes, siRNAs, triple-helix molecules, etc., inhibiting proCOL11A1 protein expression and/or activity; and
c) proCOL11A1 protein antagonist compounds inhibiting one or more of said proCOL11A1 protein functions.

In another aspect, the invention relates to a proCOL11A1 inhibitor for use in the treatment of an invasive carcinoma, or, in other words, to the use of a proCOL11A1 Inhibitor in preparing a medicinal product for treatment of an invasive carcinoma. In a particular embodiment, said invasive carcinoma is selected from renal carcinoma, invasive transitional bladder carcinoma, pancreatic ductal adenocarcinoma, infiltrating breast adenocarcinoma, colon adenocarcinoma, lung adenocarcinoma with a bronchoalveolar pattern, infiltrating squamous cell head and neck carcinoma and peritoneal carcinomatosis.

In a particular embodiment, said proCOL11A1 inhibitor is an antibody binding to proCOL11A1; advantageously, said antibody will bind specifically to an epitope located in the proCOL11A1 protein N-terminal VAR domain because said domain has the greatest sequence variation between different collagens which allows generating antibodies binding specifically to proCOL11A1 and allow specifically detecting said proCOL11A1 protein and discriminating it from other collagens the expression of which does not vary during the tumor process.

Antibody of the Invention and Applications Thereof

As mentioned above, in a particular embodiment, the invention provides an antibody binding specifically to proCOL11A1, hereinafter "antibody of the invention", comprising within the heavy chain variable region ($V_H$) analyzed by the IMGT/V-QUEST method (see below) at least one complementarity determining region or "CDR" selected from:

a CDR comprising the amino acid sequence shown in SEQ ID NO: 3 (GYSFTGYY) [CDR-H1] or a variant thereof;

a CDR comprising the amino acid sequence shown in SEQ ID NO: 4 (INCYNGAT) [CDR-H2] or a variant thereof; and a CDR comprising the amino acid sequence shown in SEQ ID NO: 5 (AIWDYEFHVMDY) [CDR-H3] or a variant thereof.

In a particular embodiment, said CDR comprising the amino acid sequence shown in SEQ ID NO: 3, present in the $V_H$ region of the antibody of the invention, is a CDR1, said CDR comprising the amino acid sequence shown in SEQ ID NO: 4, present in the $V_H$ region of the antibody of the invention, is a CDR2, and said CDR comprising the amino acid sequence shown in SEQ ID NO: 5, present in the $V_H$ region of the antibody of the invention, is a CDR3.

In a particular embodiment, the antibody of the invention comprises, within the $V_H$ region, at least one CDR comprising the amino acid sequence shown in SEQ ID NO: 3 [CDR-H1] or a variant thereof, or a CDR comprising the amino acid sequence shown in SEQ ID NO: 4 [CDR-H2] or a variant thereof, or a CDR comprising the amino acid sequence shown in SEQ ID NO: 5 [CDR-H3] or a variant thereof, preferably at least one CDR comprising the amino acid sequence shown in SEQ ID NO: 5 [CDR-H3] or a variant thereof.

In another particular embodiment, the antibody of the invention comprises, within the $V_H$ region, two of said CDRs previously mentioned; in this case, one of said CDRs is preferably a CDR comprising the amino acid sequence shown in SEQ ID NO: 5 [CDR-H3] or a variant thereof, and the other CDR is selected from a CDR comprising the amino acid sequence shown in SEQ ID NO: 3 [CDR-H1] or a variant thereof, and a CDR comprising the amino acid sequence shown in SEQ ID NO: 4 [CDR-H2] or a variant thereof.

In another particular embodiment, the antibody of the invention comprises, within the $V_H$ region, the three previously mentioned CDRs, i.e., a CDR comprising the amino acid sequence shown in SEQ ID NO: 3 [CDR-H1] or a variant thereof, a CDR comprising the amino acid sequence shown in SEQ ID NO: 4 [CDR-H2] or a variant thereof, and a CDR comprising the amino acid sequence shown in SEQ ID NO: 5 [CDR-H3] or a variant thereof.

In another particular embodiment, the antibody of the invention comprises within the light chain variable region ($V_L$) analyzed by the IMGT/V-QUEST method (see below) at least one CDR selected from the group consisting of:

a CDR comprising the amino acid sequence shown in SEQ ID NO: 6 (SSVNY) [CDR-L1] or a variant thereof;

a CDR comprising the YTS amino acid sequence [CDR-L2] or a variant thereof; and a CDR comprising the amino acid sequence shown in SEQ ID NO: 7 (QQFTSSPWT) [CDR-L3] or a variant thereof.

In a particular embodiment, said CDR comprising the amino acid sequence shown in SEQ ID NO: 6 [CDR-L1] present in the $V_L$ region of the antibody of the invention is a CDR1, said CDR comprising the YTS amino acid sequence [CDR-L2] present in the $V_L$ region of the antibody of the invention is a CDR2, and said CDR comprising the amino acid sequence shown in SEQ ID NO: 7 [CDR-L3] present in the $V_L$ region of the antibody of the invention is a CDR3.

In a particular embodiment, the antibody of the invention comprises within the $V_L$ region at least one CDR comprising the amino acid sequence shown in SEQ ID NO: 6 [CDR-L1] or a variant thereof, or a CDR comprising the YTS amino acid sequence [CDR-L2] or a variant thereof, or a CDR comprising the amino acid sequence shown in SEQ ID NO: 7 [CDR-L3] or a variant thereof.

In another particular embodiment, the antibody of the invention comprises within the $V_L$ region two of said CDRs previously mentioned, for example, a CDR comprising the amino acid sequence shown in SEQ ID NO: 6 [CDR-L1] or a variant thereof, and a CDR comprising the YTS amino acid sequence [CDR-L2] or a variant thereof, or a CDR comprising the amino acid sequence shown in SEQ ID NO: 7 [CDR-L3] or a variant thereof. Alternatively, according to this particular embodiment, the antibody of the invention comprises within the $V_L$ region a CDR comprising the YTS amino acid sequence [CDR-L2] or a variant thereof, and a CDR comprising the amino acid sequence shown in SEQ ID NO: 7 [CDR-L3] or a variant thereof.

In another particular embodiment, the antibody of the invention comprises within the $V_L$ region the three previously mentioned CDRs, i.e., a CDR comprising the amino acid sequence shown in SEQ ID NO: 6 [CDR-L1] or a variant thereof, a CDR comprising the YTS amino acid sequence [CDR-L2] or a variant thereof, and a CDR comprising the amino acid sequence shown in SEQ ID NO: 7 [CDR-L3] or a variant thereof.

The antibody of the invention can contain any combination of $V_H$ and $V_L$ regions, the characteristics of which have been mentioned previously; nevertheless, in a particular embodiment, the antibody of the invention comprises:

a) within the $V_H$ region a CDR comprising the amino acid sequence shown in SEQ ID NO: 3 [CDR-H1] or a variant thereof, a CDR comprising the amino acid sequence shown in SEQ ID NO: 4 [CDR-H2] or a variant thereof, and a CDR comprising the amino acid sequence shown in SEQ ID NO: 5 [CDR-H3] or a variant thereof, and b) within the $V_L$ region a CDR comprising the amino acid sequence shown in SEQ ID NO: 6 [CDR-L1] or a variant thereof, a CDR comprising the YTS amino acid sequence [CDR-L2] or a variant thereof, and a CDR comprising the amino acid sequence shown in SEQ ID NO: 7 [CDR-L3] or a variant thereof.

The CDR sequences can be determined according to conventional criteria, for example by means of the criteria of IMGT/V-QUEST: http://www.imt.org./IMGT_vquestshare/textes/(Brochet X, Lefranc M P and Giudicelli V: IMGT/V-QUEST: the highly customized and integrated system for IG and TR standardized V-J and V-D-J sequence analysis. Nucleic Acids Res July 1; 36 (Web Server issue):W503-508, 2008), as in the present case, or by following the numbering provided by Kabat et al., Sequences of Proteins of Immunological Interest, 5th ed., Public Health Service, National Institutes of Health, Bethesda, Md. (1991).

In a particular embodiment, the heavy chain of the antibody of the invention comprises the amino acid sequence shown in SEQ ID NO: 8 [EVQLQESGPELVKTGSSVKIS-CKASGYSFTGYYMHWVKQSQGKSLEWIGYINCYN-GAT SYNRNFKGKATFTVDTSSSTAYMQFNSLTSGD-SAVYYCAIWDYEFHVMDYWGQRTSLT VSS] or a variant thereof.

In another particular embodiment, the light chain of the antibody of the invention comprises the amino acid sequence shown in SEQ ID NO: 9 [ENVLTQSPAIM-SASLGEKVTMSCRASSSVNYMYWYQQKSDASPKL- WIYYTSNLAPGVP ARFSGSGSGNSYSLTISSMEGAG-ETYYCQQFTSSPWTFGGGTKLEIK] or a variant thereof.

In a particular embodiment, the antibody of the invention comprises:
a heavy chain comprising the amino acid sequence shown in SEQ ID NO: 8 [VH_1E8.33] or a variant thereof, and
a light chain comprising the amino acid sequence shown in SEQ ID NO: 9 [Vkappa_1E8.33] or a variant thereof.

In another even more particular embodiment, the antibody of the invention is the monoclonal antibody identified as 1E8.33, which is obtained as described in Example 5.

The antibody of the invention binds specifically to an epitope located in the proCOL11A1 protein N-terminal VAR domain.

As it has been previously defined, the term "antibody" includes whole monoclonal antibodies or polyclonal antibodies or fragments thereof, for example, Fv, Fab, Fab', F(ab')$_2$, single chain Fv (scFv) fragments, human antibodies, humanized antibodies, antibodies of a non-human origin and polypeptides derived from immunoglobulins produced by means of genetic engineering techniques, for example, Fv fragments stabilized by means of disulfide bridges (dsFv), molecules with single chain variable region domains (Abs), minibodies, etc.

Generally, the antibody of the invention is a monoclonal antibody or a fragment of said antibody which retains the capacity to bind to proCOL11A1. Said antibodies are preferably human or humanized antibodies. Humanized antibodies can be prepared, for example, from murine monoclonal antibodies and human monoclonal antibodies can be prepared, for example, using transgenic mice or by means of the phage display technique. The antibodies of the invention can generally be prepared by means of a range of processes known by persons having ordinary skill in the art. By way of Illustration, the following publications can be cited: Monoclonal Antibodies, Hybridomas: A New Dimension in Biological Analyses, Kennet et al. (ads.), Plenum Press, New York (1980); Antibodies: A Laboratory Manual, Harlow and Land (eds.), Cold Spring Harbor Laboratory Press, Cold Spring Harbor, N.Y., (1988); Monoclonal Antibodies: Principles and Practice, Goding, 3<rd> Edition, Academic Press (1996). Additionally, the monoclonal antibodies secreted by hybridomas can be purified by conventional methods. Example 5 describes obtaining monoclonal and polyclonal antibodies against pro COL11A1.

The fragments with the capacity to bind to proCOL11A1 can also be obtained by conventional methods known by persons having ordinary skill in the art. Said methods can involve isolating DNA that encodes the polypeptide chain (or a fragment thereof) of a monoclonal antibody of interest and manipulating DNA by means of recombinant DNA technology. DNA can be used to generate another DNA of interest, or an altered DNA, (for example by means of mutagenesis) for adding, removing or substituting one or more amino acids, for example, the DNA that encodes the polypeptide chains of an antibody (e.g., the heavy or light chains, the variable region or the whole antibody) can be isolated from murine B cells immunized with proCOL11A1. The DNA can be isolated and amplified by conventional methods, for example by means of PCR.

The single-chain antibodies can be obtained by conventional methods by binding the variable region of the heavy and light chains (Fv region) by means of an amino acid bridge. The scFvs can be prepared by fusing the DNA encoding a linker peptide between the DNAs encoding the polypeptides of the variable regions ($V_L$ and $V_H$). The production of scFvs is described in a number of documents, for example, in U.S. Pat. No. 4,946,778, Bird (Science 242: 423, 1988), Huston et al. (Proc. Natl. Acad Sci USA 85: 5879, 1988) and Ward et al. (Nature 334: 544, 1989).

The person skilled in the art will understand that the amino acid sequences of the antibodies of the invention can include one or more amino acid substitutions such that, even though the primary sequence of the polypeptide is altered, the capacity of the antibody to bind to proCOL11A17 is maintained. Said substitution can be a conservative substitution and is generally applied to indicate that the substitution of one amino acid with another amino acid with similar properties (for example, the substitution of glutamic acid (loaded amino acid) with aspartic acid would be a conservative amino acid substitution).

The present invention also contemplates variants of the sequences of the heavy and light chains identified in this description, which fall within the scope of the present invention. As it is used herein, the term "variant" refers to substantially similar sequences. The variants generally have the same biological activity from the qualitative viewpoint as the native sequence. A variant of a polypeptide sequence can be a polypeptide sequence derivative identified in this description comprising the addition, deletion or substitution of one or more amino acids. The variants can differ from the described sequences within framework regions or within the CDRs of any of the chains heavy or light. By way of illustration, the invention includes antibodies, for example, monoclonal antibodies, or fragments thereof with the capacity to bind to proCOL11A1, comprising amino acid sequences having at least approximately 70% sequence identity with the amino acid sequences shown in SEQ ID NOs: 3 to 9, and with the YTS sequence, preferably at least 75%, 80%, 85%, 90%, 91%, 92%, 93%, 94%, 95%, 96%, 97%, 98% or 99% sequence identity with the amino acid sequences shown in SEQ ID NOs: 3 to 9, and with the YTS sequence.

The antibody of the invention can be used in the diagnosis, prognosis and/or differential diagnosis of an invasive carcinoma. The antibody of the invention can further be used in the treatment of an invasive carcinoma.

Therefore, in another aspect, the invention relates to the use of an antibody of the invention for the diagnosis, prognosis and/or differential diagnosis of an invasive carcinoma in vitro. In a particular embodiment, said invasive carcinoma is selected from renal carcinoma, invasive transitional bladder carcinoma, pancreatic ductal adenocarcinoma, infiltrating breast adenocarcinoma, colon adenocarcinoma, lung adenocarcinoma with a bronchoalveolar pattern, Infiltrating squamous cell head and neck carcinoma and peritoneal carcinomatosis.

In another aspect, the invention relates to an antibody of the invention for use in the treatment of an invasive carcinoma, or, in other words, to the use of an antibody of the invention in preparing a medicinal product for treatment of an invasive carcinoma. In a particular embodiment, said invasive carcinoma is selected from renal carcinoma, invasive transitional bladder carcinoma, pancreatic ductal adenocarcinoma, infiltrating breast adenocarcinoma, colon adenocarcinoma, lung adenocarcinoma with a bronchoalveolar pattern, infiltrating squamous cell head and neck carcinoma and peritoneal carcinomatosis.

Pharmaceutical Compositions

In another aspect, the invention relates to a pharmaceutical composition, hereinafter "pharmaceutical composition of the invention", comprising a therapeutically effective amount of at least one proCOL11A1 inhibitor, together with a pharmaceutically acceptable excipient or carrier.

The excipients, carriers and, where appropriate, auxiliary substances possibly present in the pharmaceutical composition provided by this invention have to be pharmaceutically and pharmacologically tolerable, such that they can be combined with other components of the formulation or preparation and not have adverse effects on the treated organism. The pharmaceutical compositions or formulations include those that are suitable for oral or parenteral administration (including subcutaneous, intradermal, intramuscular and intravenous administration), even though the best administration route depends on the patient's condition. The formulations can be in the form of single doses. The formulations are prepared according to methods known in the field of pharmacology. The amounts of active substances to be administered can vary depending on the particularities of therapy.

In a particular embodiment, the pharmaceutical composition of the invention further comprises one or more active ingredients inhibiting proCOL11A1 protein function.

The following examples illustrate the invention and must not be considered in a limiting sense thereof.

EXAMPLE 1

Differential Analysis of col11a1 Gene Expression in Kidney Tissue Samples Using Human Genome U95 DNA Arrays Microarrays 1.1 Materials and Methods Microarrays.

GeneChip Test 3 microarrays (Affymetrix, Santa Clara), which allow analyzing the quality of RNA, prior to expression analysis with the GeneChip Human Genome U95A microarray (Affymetrix, Santa Clara), which represents 12,000 complete sequences of annotated genes, were used; Collagen XI, alpha 1 (col11a1) gene is represented in the microarray by the set of Affymetrix 37892_at probes, which are sense oligonucleotides 25 nucleotides long, designed based on the Unigene Hs.82772 or GeneBank J04177 sequence.

Samples.

The analysis was carried out with total RNA from 1 neoplastic kidney tissue sample from 1 individual who has renal oncocytoma, with equimolar mixtures (pools) of total RNAs from a set of 8 neoplastic kidney tissue samples from 8 individuals who have renal carcinoma conventional, with total RNA from 1 neoplastic kidney tissue sample from 1 individual who has chromophobe renal carcinoma and, as a negative control, with equimolar mixtures of total RNAs from a set of non-neoplastic kidney tissue samples from individuals who have renal oncocytoma, conventional renal carcinoma and chromophobe renal carcinoma. All the samples were histologically classified in the Anatomic Pathology Department of Hospital Universitario Marqués de Valdecilla (Santander Spain), the same hospital where the samples had been taken, following the principles of the Declaration of Helsinki. The samples were frozen in liquid nitrogen immediately after extraction and were kept at −80° C. until the time of analysis.

TABLE 1

Clinical pathology data of the analyzed renal neoplasms

| Case | Age | Sex | Histological diagnosis | Stage | Progress |
|---|---|---|---|---|---|
| 1 | 58 | Male | Conventional RC | II | A&H (28 months) |
| 2 | 80 | Male | Conventional RC | II | A&H (16 months) |
| 3 | 78 | Male | Conventional RC | II | A&H (20 months) |
| 4 | 38 | Male | Conventional RC | II | A&H (24 months) |
| 5 | 68 | Male | Conventional RC | II | A&H (24 months) |
| 6 | 76 | Female | Conventional RC | II | A&H (22 months) |
| 7 | 51 | Male | Conventional RC | III | DFD (15 months) |
| 8 | 45 | Male | Conventional RC | III | DFD (11 months) |
| 9 | 57 | Male | Chromophobe RC | II | A&H (25 months) |
| 10 | 79 | Male | Renal oncocytoma | II | A&H (26 months) |

RC: Renal carcinoma
A&H (n months): Alive and Healthy, n months after diagnosis.
DFD (n months): Dead from disease, n months after diagnosis.

Analysis of Gene Expression Using GeneChip cRNA Synthesis

The total RNA of each of the biopsies was obtained by homogenizing the tissue in TRIzol® Reagent (Life Technologies), following supplier recommendations. The resulting total RNA was cleaned with Rneasy kit (QIAGEN) (Chomczynski P. et al., Anal. Biochem., 1987, 162: 156; Chomczynski P., Biotechniques, 1993, 15: 532). 10 µg of each total RNA preparation were used as starting material for synthesis of the first strand of cDNA with SuperScript™ II RNase reverse transcriptase enzyme (Life Technologies), using an oligo-dT oligonucleotide containing the sequence of the T7 phage RNA polymerase promoter as a primer. The second strand of cDNA was synthesized using E. coli DNA polymerase I (Invitrogen Life Technologies), E. coli DNA ligase (Invitrogen Life Technologies), E. coli Rnase H (Invitrogen Life Technologies), and T4 phage DNA polymerase (Invitrogen Life Technologies) enzymes. Biotin-labeled cRNA was synthesized using ENZO BioArray™ HighYield™ Transcript Labeling Kit (Enzo Diagnostics Inc). After in vitro transcription, the non-incorporated nucleotides were removed using Rneasy columns (QIAGEN).

Array Hybridization and Scanning

15 µg of each biotinylated cRNA were fragmented at 94° C. for 35 minutes in a buffer solution containing 40 mM Tris-acetate (pH 8.1), 100 mM potassium acetate (KOAc) and 30 mM magnesium acetate (MgOAc). The fragmented cRNA was mixed with hybridization buffer [100 mM 2-(N_morpholino)ethanesulfonic acid (MES), 1 M NaCl, 20 mM ethylenediaminetetraacetic acid (EDTA), 0.01% Tween® 20] and was heated at 99° C. for 5 minutes and subsequently at 45° C. for 5 minutes to then be loaded in the Affymetrix array. The first array in which hybridization was performed was Affymetrix Test 3. This array allows analyzing the quality of RNA prior to expression analysis in GeneChip Human Genome 95 A (HG-U95A) (Affymetrix, Santa Clara). For hybridization, the arrays were incubated in a rotary oven at 45° for 16 hours and with a constant rotation of 60 rpm. Each array was washed and stained in the Affymetrix Fluidics Station. A washing and staining program was used that included:

10×2 washing cycles with 6× SSPE-T (0.9 M NaCl, 60 mM $NaH_2PO_4$, 6 mM EDTA, 0.01% Tween® 20) at 25° C.;

4×15 cycles with 0.1 mM MES. 0.1M NaCl, 0.01% Tween® 20 at 50° C.;

staining biotinylated cRNA with a streptavidin-phycoerythrin conjugate (10 µg/ml) (Molecular Probes);

10×4 washing cycles with 6× SSPE-T at 25° C.;

staining with anti-streptavidin antibody (BA-0500, Vector Laboratories) for 10 minutes;

staining with a streptavidin-phycoerythrin conjugate (1 mg/ml) (Molecular Probes) for 10 minutes; and 15×4 washing cycles with SSPE-T at 30° C.

The arrays were scanned at 560 nm using a laser scanning confocal microscope (Agilent GeneArray Scanner). The intensity readings were analyzed with Microarray Suite 5.0 software. For array comparison, the arrays were scaled to a total intensity of 100.

1.2 Results

The differential analysis of col11a1 gene expression in the different renal neoplasms with respect to the control was performed using the array comparison data obtained using Affymetrix software. The parameters taken into account (in the order in which they are on the list) were:

i) Detection: Indicates if the transcript is Present (P), Absent (A) or Marginal (M);

ii) Change: Indicates if the expression of a determined transcript increases (I), Decreases (D), Does Not Change (NC), Marginally Increases (MI), or Marginally Decreases (MD); and iii) Signal Log Ratio (SLG): Indicates the level of change of expression between the baseline (control) and a test sample. This change is expressed as $\log_2$ of the ratio (fold change or number of times that the gene expression is high or repressed in the test-tumor sample versus the control-healthy sample). An SLR value of 1 (equivalent to a fold change of 2) is considered significant for transcripts the expression of which increases versus the control, and an SLR value of −1 is considered significant for transcripts the expression of which decreases versus the control.

Analysis of differential col11a1 gene expression in the different types of renal neoplasms analyzed versus the control demonstrated that col11a1 gene expression levels were slightly increased, 2 fold (SLR=1), in oncocytoma (benign tumor) biopsies, and greatly increased in malignant tumors with an increase proportional to the invasiveness of the type of tumor, over 8 fold (SLR>3) in conventional carcinoma biopsies and over 120 fold (SLR>7) in chromophobe carcinoma biopsies (Table 2).

TABLE 2

Results obtained with Genechip Human U95A array for col11a1. N. Acc. J04177

| Detection in control sample | Detection in Oncocytoma | SLR Oncocytoma vs. Control | Change in Oncocytoma vs. Control |
|---|---|---|---|
| A | P | 1 | I |

| Detection in control sample | Detection in Conventional Carcinoma | SLR in Conventional Carcinoma vs. Control | Change in Conventional Carcinoma vs. Control |
|---|---|---|---|
| A | P | 3.9 | I |

| Detection in control sample | Detection in Chromophobe Carcinoma | SLR in Chromophobe Carcinoma vs. Control | Change in Chromophobe Carcinoma vs. Control |
|---|---|---|---|
| A | P | 7.3 | I |

EXAMPLE 2

Differential Analysis of col11a1 Gene Expression in Pancreatic Tissue Samples Using Human Genome U133 DNA Arrays 2.1 Materials and Methods Microarrays.

GeneChip Test 3 microarrays (Affymetrix, Santa Clara) were used, which allow analyzing the quality of RNA, prior to expression analysis with GeneChip Human Genome U133A microarray (Affymetrix, Santa Clara), which represents 15,000 complete sequences of annotated genes and 7,000 expressed gene sequences without annotation (ESTs or expressed sequence tags); Collagen XI, alpha 1 gene (col11a1) is represented in the microarray by the set of Affymetrix 37892_at probes, which are sense oligonucleotides 25 nucleotides long, designed based on the Unigene Hs.82772 or GeneBank J04177 sequence.

Samples.

The samples studied were from biopsies, obtained by surgical resection, from (1) control subjects without pancreatic ductal adenocarcinoma (n=1), (11) apparently non-tumorous ('healthy') pancreatic tissue from individuals who had pancreatic ductal adenocarcinoma (n=1), (iii) control subjects without pancreatic ductal adenocarcinoma, but with chronic pancreatitis (n=2) and (iv) patients who were subsequently clinically typed and who had pancreatic ductal adenocarcinoma (n=12) in one of the following stages: Stage I, tumor limited to the pancreas; Stage III, tumor extended to regional lymph nodes; and Stage IVB, there is metastasis in distant tissues or organs. All the samples were histologically classified (grade and stage) in Hospital Central of Asturias, the same hospital where the samples had been taken, following the principles of the declaration of Helsinki. The samples were frozen in liquid nitrogen immediately after extraction and were kept at −80° C. until the time of analysis. Several cases of each type of tumor as well as of healthy samples were received:

Healthy tissue control: 2 samples
Tissue with pancreatitis control: 2 samples
Stage I tumor: 7 samples
Stage III tumor: 1 sample
Stage IV tumor: 2 samples
Ampullary tumor: 2 samples

TABLE 3

Description of the samples analyzed

| Code of the sample | Type | TNM Classification | Stage |
|---|---|---|---|
| PA36 | Healthy control | — | — |
| PA26 | Healthy control | — | — |
| PA29 | Pancreatitis control | — | — |
| PA46 | Pancreatitis control | — | — |
| PA02 | Ductal adenocarcinoma | T2N0M0 | I |
| PA03 | Ductal adenocarcinoma | T2N0M0 | I |
| PA17 | Ductal adenocarcinoma | T1bN0M0 | I |
| PA19 | Ductal adenocarcinoma | T1bN0M0 | I |
| PA25 | Ductal adenocarcinoma | T1N0M0 | I |
| PA27 | Ductal adenocarcinoma | T1N0M0 | I |
| PA33 | Ductal adenocarcinoma | T1bN0M0 | I |
| PA20 | Ampullary tumor | T1bN1M0 | III |
| PA24 | Ductal adenocarcinoma | T3N1M0 | III |
| PA31 | Ampullary tumor | T1bN1M0 | III |
| PA16 | Ductal adenocarcinoma | T2N1M1 | IV |
| PA23 | Ductal adenocarcinoma | T1bN1M1 | IV |

Analysis of Gene Expression Using GeneChip

The analysis was carried out with total RNA from individual subjects. The 16 samples analyzed were those described in Table 3.

cRNA Synthesis

The total RNA of each of the biopsies was obtained by homogenizing the tissue in TRIzol® Reagent (Life Technologies), following supplier recommendations. The resulting total RNA was cleaned with Rneasy kit (QIAGEN) (Chomczynski P. et al., Anal. Biochem., 1987, 162: 156; Chomczynski P., Biotechniques, 1993, 15: 532). 10 µg of each total RNA preparation were used as starting material for synthesis of the first strand of cDNA with SuperScript™ II RNase reverse transcriptase enzyme (Life Technologies), using an oligo-dT oligonucleotide containing the sequence of the T7 phage RNA polymerase promoter as a primer. The second strand of cDNA was synthesized using E. coli DNA polymerase I (Invitrogen Life Technologies), E. coli DNA ligase (Invitrogen Life Technologies), E. coli Rnase H (Invitrogen Life Technologies), and T4 phage DNA polymerase (Invitrogen Life Technologies) enzymes. Biotin-labeled cRNA was synthesized using ENZO BioArray™ HighYield™ Transcript Labeling Kit (Enzo Diagnostics Inc). After in vitro transcription, the non-incorporated nucleotides were removed using Rneasy columns (QIAGEN).

Array Hybridization and Scanning

15 µg of each biotinylated cRNA were fragmented at 94° C. for 35 minutes in a buffer solution containing 40 mM Tris-acetate (pH 8.1), 100 mM KOAc and 30 mM MgOAc. The fragmented cRNA was mixed with hybridization buffer (100 mM MES, NaCl1M, 20 mM EDTA, 0.01% Tween® 20) and was heated at 99° C. for 5 minutes and subsequently at 45° C. for 5 minutes to then be loaded in the Affymetrix array. The first array in which hybridization was performed was Affymetrix Test 3. This array allows analyzing the quality of RNA prior to expression analysis in the GeneChip Human Genome 133 A (HG-U133A) (Affymetrix, Santa Clara). For hybridization, the arrays were incubated in a rotary oven at 45° C. for 16 hours and with a constant rotation of 60 rpm. Each array was washed and stained in the Affymetrix Fluidics Station®. A washing and staining program was used that included:

- 10×2 washing cycles with 6× SSPE-T (0.9 M NaCl, 60 mM $NaH_2PO_4$, 6 mM EDTA, 0.01% Tween® 20) at 25° C.;
- 4×15 cycles with 0.1 mM MES, 0.1 M NaCl, 0.01% Tween® 20 at 50° C.;
- staining biotinylated cRNA with a streptavidin-phycoerythrin conjugate (10 µg/ml) (Molecular Probes);
- 10×4 washing cycles with 6× SSPE-T at 25° C.;
- staining with anti-streptavidin antibody (BA-0500, Vector Laboratories) for 10 minutes;
- staining with a streptavidin-phycoerythrin conjugate (1 mg/ml) (Molecular Probes) for 10 minutes; and
- 15×4 washing cycles with SSPE-T at 30° C.

The arrays were scanned at 560 nm using a laser scanning confocal microscope (Agilent GeneArray Scanner). The intensity readings were analyzed with Microarray Suite 5.0 software. For array comparison, the arrays were scaled to a total intensity of 100.

2.2 Results

The differential analysis of col11a1 gene expression in tumor stages with respect to the control was performed using the array comparison data obtained using Affymetrix software. The parameters taken into account (in the order in which they are on the list) were:

i) Detection: Indicates if the transcript is Present (P), Absent (A) or Marginal (M);

ii) Change: Indicates if the expression of a determined transcript Increases (I), Decreases (D), or Does Not Change (NC);

iii) Signal Log Ratio (SLG): Indicates the level of change of expression between the baseline (control) and a test sample. This change is expressed as $log_2$ of the ratio (fold change or number of times that the gene expression is high or repressed in the test-tumor sample versus the control-healthy sample). An SLR value of 1 (equivalent to a fold change of 2) is considered significant for transcripts the expression of which increases versus the control, and an SLR value of −1 is considered significant for transcripts the expression of which decreases versus the control.

Analysis of differential col11a1 gene expression in tumor stages with respect to the healthy control demonstrates that col11a1 gene expression levels were clearly increased in all pancreatic ductal adenocarcinomas analyzed (10), but col11a1 expression was not detected in the 2 ampullary tumors analyzed. The mean overexpression with respect to the healthy control of the early stage (Stage I) samples was over 30 fold (SLR>5) and over 60 fold (SLR>6) in advanced tumor (Stage IVB) biopsies (Table 4). These values are even higher when comparing col11a1 gene expression in tumors with respect to the sample from individuals who have chronic pancreatitis but not pancreatic ductal adenocarcinoma (PA46), the mean expression increase in early stage (Stage I) samples being over 100 fold (SLR=6.7), and over 120 fold (SLR>7) in advanced tumor (Stage IVB) biopsies (Table 5). Overexpression of col11a1 gene expression levels in tumor samples with respect to chronic pancreatitis samples demonstrated that this overexpression is specific of the tumor process and is not due to stromal proliferation inherent to the inflammation process characteristic of pancreatitis; this inflammation is also characteristic of tumor processes as a side effect. Col11a1 gene was detected as Absent by MAS 5.0 software in the 4 controls analyzed (Tables 4 and 5).

TABLE 4

Results obtained with Genechip Human U133A array for col11a1. N. Acc. J04177.
Result of comparisons to the healthy control (PA36)

| Sample* | Detection | SLR Sample* vs. PA36 | Change Sample* vs. PA36 |
|---|---|---|---|
| Controls | | | |
| PA36 (normal pancreas) | A | — | — |
| PA26 (normal pancreas) | A | 1.8 | NC |
| PA29 (pancreatitis) | A | 0.1 | NC |
| PA46 (pancreatitis) | A | −1.1 | NC |
| Stage I tumors | | | |
| PA02 | P | 4.6 | I |
| PA03 | P | 7.3 | I |
| PA17 | P | 4.2 | I |
| PA19 | P | 4.7 | I |
| PA33 | P | 4.7 | I |
| PA25 | P | 4 | I |
| PA27 | P | 7.3 | I |

TABLE 4-continued

Results obtained with Genechip Human U133A array for
col11a1. N. Acc. J04177.
Result of comparisons to the healthy control (PA36)

| Sample* | Detection | SLR Sample* vs. PA36 | Change Sample* vs. PA36 |
|---|---|---|---|
| Stage III tumors | | | |
| PA24 | P | 5.5 | I |
| Stage IV tumors | | | |
| PA16 | P | 6.7 | I |
| PA23 | P | 5.4 | I |
| Ampullary tumors | | | |
| PA31 | A | 0.8 | NC |
| PA20 | A | 0.3 | NC |

TABLE 5

Results obtained with Genechip Human U133A array for
col11a1. N. Acc. J04177.
Result of comparisons to the pancreatitis control (PA46)

| Sample* | Detection | SLR Sample* vs. PA46 | Change Sample* vs. PA46 |
|---|---|---|---|
| Controls | | | |
| PA46 (pancreatitis) | A | — | — |
| PA29 (pancreatitis) | A | 1.1 | NC |
| PA36 (normal pancreas) | A | 1.1 | NC |
| PA26 (normal pancreas) | A | 3.5 | NC |
| Stage I tumors | | | |
| PA02 | P | 5.8 | I |
| PA03 | P | 8.9 | I |
| PA17 | P | 5.4 | I |
| PA19 | P | 5.9 | I |
| PA33 | P | 6.2 | I |
| PA25 | P | 5.8 | I |
| PA27 | P | 8.9 | I |
| Stage III tumors | | | |
| PA24 | P | 7 | I |
| Stage IV tumors | | | |
| PA23 | P | 7.1 | I |
| PA16 | P | 8 | I |
| Stage III ampullary tumors | | | |
| PA31 | A | 2.8 | NC |
| PA20 | A | −0.3 | NC |

EXAMPLE 3

Differential Analysis of col11a1 Gene Expression in Bladder Tissue Samples Using Human Genome U95 DNA Arrays 3.1 Materials and Methods Microarrays.

GeneChip Test 3 microarrays (Affymetrix, Santa Clara), which allow analyzing the quality of RNA, prior to analysis with the GeneChip Human Genome U95A microarray (Affymetrix, Santa Clara), which represents 12,000 complete sequences of annotated genes, were used; col11a1 gene is represented in the microarray by the set of Affymetrix 37892_at probes, which are sense oligonucleotides 25 nucleotides long, designed based on the Unigene Hs.82772 or GeneBanK J04177 sequence.

Samples.

The samples studied were from biopsies, obtained by transurethral surgical resection, from (i) control subjects without transitional bladder carcinoma (n=7), and (ii) patients who were clinically typed after resection and who had transitional bladder carcinoma (n=22) in one of the following stages: low grade tumors respecting the lamina propria (Ta G1), high grade tumors infiltrating the lamina propria (T1 G3) and high grade tumors invading muscle tissue (T2 G3). All the samples were histologically classified (grade and stage) in the Anatomic Pathology Department of Hospital Universitario Marqués de Valdecilla (Santander, Spain), the same hospital where the samples had been taken, following the principles of the Declaration of Helsinki. The samples were frozen in liquid nitrogen immediately after extraction and were kept at −80° C. until the time of analysis. Several cases of each type of tumor as well as of healthy samples were received:

Healthy tissue control (mucosa without muscular layer): 5 samples

Healthy tissue control (mucosa with muscular layer): 2 samples

Low grade tumor respecting lamina propria (TaG1): 9 samples

High grade tumor infiltrating lamina propria (T1G3): 7 samples

High grade tumor invading muscle (T2G3): 6 samples

Analysis of Gene Expression Using GeneChip

The analysis was carried out with total RNA from individual subjects, and with equimolar mixtures (pools) of total RNAs from different healthy subjects or from subjects who have transitional bladder carcinoma in the same stage (Table 6).

TABLE 6

Description and number of samples analyzed

| | Epithelial control | Muscular control | Ta G1 | T1 G3 | T2 G3 |
|---|---|---|---|---|---|
| Samples | 3*(pC1)[a], 2(pC3) | 2(pC2) | 1, 4(pTa.1)[b], 4(pTa.2) | 1, 2(pT1.1)[c], 4(pT1.2) | 1, 2(pT2.1)[d], 3(pT2.2) |

*number of samples forming part of each pool.
[a]pC: pool of control samples. Example: 3(pC1) = pool 1 of 3 control samples.
[b]pTa: pool of samples of low grade tumors (G1) respecting the lamina propria (Ta). Example: 4(pTa.1) = pool 1 of 4 samples TaG1.
[c]pT1: pool of samples of high grade tumors (G3) infiltrating the lamina propria (T1). Example: 2(pT1.1) = pool 1 of 2 samples T1G3.
[d]pT2: pool of samples of high grade tumors (G3) invading muscle tissue (T2). Example: 2(pT2.1) = pool 1 of 2 samples T2G3.

cRNA Synthesis

The total RNA of each of the biopsies was obtained by homogenizing the tissue in TRIzol® Reagent (Life Technologies), following supplier recommendations. The resulting total RNA was cleaned with Rneasy kit (QIAGEN) (Chomczynski P. et al., Anal. Biochem., 1987, 162: 156; Chomczynski P., Biotechniques, 1993, 15: 532). 10 µg of each total RNA preparation were used as starting material for synthesis of the first strand of cDNA with SuperScript™ II RNase reverse transcriptase enzyme (Life Technologies), using an oligo-dT oligonucleotide containing the sequence of the T7 phage RNA polymerase promoter as a primer. The second strand of cDNA was synthesized using E. coli DNA polymerase I (Invitrogen Life Technologies), E. coli DNA ligase (Invitrogen Life Technologies), E. coli Rnase H (Invitrogen Life Technologies), and T4 phage DNA polymerase (Invitrogen Life Technologies) enzymes. Biotin-labeled cRNA was synthesized using ENZO BioArray™ HighYield™ Transcript Labeling Kit (Enzo Diagnostics Inc). After in vitro transcription, the non-incorporated nucleotides were removed using Rneasy columns (QIAGEN).

Array Hybridization and Scanning

15 μg of each biotinylated cRNA were fragmented at 94° C. for 35 minutes in a buffer solution containing 40 mM Tris-acetate (pH 8.1), 100 mM KOAc and 30 mM MgOAc. The fragmented cRNA was mixed with hybridization buffer (100 mM MES, NaCl1M, 20 mM EDTA, 0.01% Tween® 20) and was heated at 99° C. for 5 minutes and subsequently at 45° C. for 5 minutes to then be loaded in the Affymetrix array. The first array in which hybridization was performed was Affymetrix Test 3. This array allows analyzing the quality of RNA prior to expression analysis in the GeneChip Human Genome 95 A (HG-U95A) (Affymetrix, Santa Clara). For hybridization, the arrays were incubated in a rotary oven at 45° C. for 16 hours and with a constant rotation of 60 rpm. Each array was washed and stained in the Affymetrix Fluidics Station®. A washing and staining program was used that included:

- 10×2 washing cycles with 6× SSPE-T (0.9 M NaCl, 60 mM $NaH_2PO_4$, 6 mM EDTA, 0.01% Tween® 20) at 25° C.;
- 4×15 cycles with 0.1 mM MES, 0.1M NaCl, 0.01% Tween® 20 at 50° C.;
- staining biotinylated cRNA with a streptavidin-phycoerythrin conjugate (10 μg/ml) (Molecular Probes);
- 10×4 washing cycles with 6× SSPE-T at 25° C.;
- staining with anti-streptavidin antibody (BA-0500, Vector Laboratories) for 10 minutes;
- staining with a streptavidin-phycoerythrin conjugate (1 mg/ml) (Molecular Probes) for 10 minutes; and
- 15×4 washing cycles with SSPE-T at 30° C.

The arrays were scanned at 560 nm using a laser scanning confocal microscope (Agilent GeneArray Scanner). The intensity readings were analyzed with Microarray Suite 5.0 software. For array comparison, the arrays were scaled to a total intensity of 100.

3.2 Results

The differential analysis of col11a1 gene expression in tumor stages with respect to the control was performed using the array comparison data obtained using Affymetrix software. The parameters taken into account (in the order in which they are on the list) were:
  i) Detection: Indicates if the transcript is Present (P), Absent (A) or Marginal (M);
  ii) Change: Indicates if the expression of a determined transcript increases (I), Decreases (D), Does Not Change (NC), Marginally Increases (MI), or Marginally Decreases (MD); and
  iii) Signal Log Ratio (SLG): Indicates the level of change of expression between the baseline (control) and a test sample. This change is expressed as $\log_2$ of the ratio (fold change or number of times that the gene expression is high or repressed in the test-tumor sample versus the control-healthy sample). An SLR value of 1 (equivalent to a fold change of 2) is considered significant for transcripts the expression of which increases versus the control, and an SLR value of −1 is considered significant for transcripts the expression of which decreases versus the control.

Analysis of differential col11A1 gene expression in tumor stages with respect to the control demonstrates that col11A1 gene expression in superficial bladder tumors (TaG1 low grade transitional carcinoma or T1 G3 high grade transitional carcinoma invading the lamina propria) did not change with respect to that of the controls; even though the mean SLR of the three stages was 3.2, Affymetrix software used for determining the reliability of the data considered that col11A1 gene was not expressed in these tumors (A). In contrast, col11a1 gene expression levels were high, over 20 fold (SLR=4.5), in invasive tumor bladder biopsies (T2G3 high grade transitional bladder carcinoma Invading muscle) (Table 7).

TABLE 7

Results obtained with Genechip Human U95A array for col11a1. N. Acc. J04177

| Detection in control sample | Detection in stage TaG1 | Ta G1 SLR vs. Control | Change in stage TaG1 |
|---|---|---|---|
| A | A | 2.1 | NC |

| Detection in control sample | Detection in stage T1 G3 | T1G3 SLR vs. Control | Change in stage T1G3 |
|---|---|---|---|
| A | A | 3 | NC |

| Detection in control sample | Detection in stage T2 G3 | T2G3 SLR vs. Control | Change in stage T2G3 |
|---|---|---|---|
| A | P | 4.5 | I |

EXAMPLE 4

Differential Analysis of Col11a1 Gene Expression in Pancreatic Tissue Samples Using Quantitative Real Time RT-PCR 4.1 Materials and Methods Method.

The method used consists of reverse transcription of mRNA into cDNA and subsequent amplification in a LightCycler (Roche Diagnostics Inc., Mannheim, Germany), using SYBR Green for detecting the amplified product. Quantification is performed in real time and allows calculating the relative expression of the sequence in different samples in the linear amplification phase of the reaction.

Samples.

The samples studied were from biopsies, obtained by surgical resection, of apparently non-tumorous pancreatic tissue from (i) individuals who had pancreatic ductal adenocarcinoma (n=1), (ii) control subjects without pancreatic ductal adenocarcinoma with chronic pancreatitis (n=1), and (iii) patients who were subsequently clinically typed and who had pancreatic ductal adenocarcinoma (n=5) in one of the following stages: Stage I, tumor limited to the pancreas and Stage IV, there is metastasis in distant tissues or organs. All the samples were histologically classified (grade and stage) in Hospital Central of Asturias, the same hospital where the samples had been taken. The samples were frozen in liquid nitrogen immediately after extraction and were kept at −80° C. until the time of analysis.

Quantitative Real Time RT-PCR.

The analysis was carried out with total RNA from individual subjects. The 7 samples that were analyzed are described in Table 8.

TABLE 8

Description of the samples analyzed

| Sample code | Type | TNM Classification | Stage |
|---|---|---|---|
| PA36 | Healthy control | — | — |
| PA46 | Pancreatitis control | — | — |
| PA19 | Tumor | T1bN0M0 | I |
| PA27 | Tumor | T1N0M0 | I |
| PA33 | Tumor | T1bN0M0 | I |
| PA14 | Tumor | T3N1M1 | IV |
| PA16 | Tumor | T2N1M1 | IV | cDNA Synthesis

The total RNA of each of the biopsies was obtained by homogenizing the tissue in TRIzol® Reagent (Life Technologies), following supplier recommendations. The resulting total RNA was cleaned with Rneasy kit (QIAGEN) (Chomczynski P. et al., Anal. Biochem., 1987, 162: 156; Chomczynski P., Biotechniques, 1993, 15: 532). The RNA was spectrophotometrically quantified and 5 μg of total RNA were digested with DNaseI. 1 μg of RNA treated with DNAse was used as starting material for synthesis of the first strand of cDNA with SuperScript™ II RNase reverse transcriptase enzyme (Life Technologies), using an oligo-dT oligonucleotide containing the sequence of the T7 phage RNA polymerase promoter as a primer. Aliquots of cDNA diluted to working concentration were prepared.

Amplification

The synthesized cDNA was amplified using primers specific to human col11a1 gene [5'-TGGTGATCAGAATCA-GAAGTTCG-3' (SEQ ID NO: 1) and 5'-AGGAGAGTT-GAGAATTGGGA ATC-3' (SEQ ID NO: 2)], and primers specific to human L10 ribosomal protein (ribl10) gene [5'-TGCGATGGCTGCACACA-3' (SEQ ID NO: 11) and 5'-TCCCTTAGAGCAACCCATACAAC-3' (SEQ ID NO: 12)]. The real time PCR reactions were prepared using LightCycler-FastStart DNA master SYBR Green I kit (Roche Diagnostics Inc., Mannheim, Germany), following the manufacturer's Instructions. The amplification program consisted of 1 cycle at 95° C. for 10 minutes (hot start), followed by 45 cycles at 95° C. (denaturation) for 10 seconds, 60° C. (annealing) for 5 seconds, 72° C. (amplification and acquisition of fluorescence) for 10 seconds. The denaturation curve analysis program consisted of a cycle of one pulse at 95° C., 65° C. for 15 seconds, and a pulse at 95° C. during the amplification and acquisition step.

Quantification

First, the specificity of the PCR products was determined by analyzing the denaturation curves. Then the ratio of the abundance of mRNA transcribed from col11a1 and the abundance of ribl10 transcripts was calculated as a relative measurement of gene expression, and data of the ration was normalized in each of the tumor samples based on the values of the control sample. A standard curve made with serial dilutions of cDNA was constructed to calculate the efficiency of the PCR reactions (col11a1 and ribl10) for each gene sequence. Arbitrary values of 10, 5, 2.5, 1.25 and 0.625 were given to the concentrations of cDNA template for reactions in the standard curve. The efficiency was calculated using the following equation:

$$E = 10^{-1/s}$$

where
  E is the efficiency of amplification, and
  s is the slope of the standard straight line.

The ratio of the gene expression values was determined using the following equation, which relates experimental data of the amplification and corrects the error caused by the difference in efficiency of the PCR reactions:

$$\text{Ratio} = \frac{E_{target}^{-(Cp\ control\ target - Cp\ sample\ target)}}{E_{reference}^{-(Cp\ reference\ control - Cp\ reference\ sample)}}$$

where
  E is the efficiency of amplification,
  Cp is the crossing point,
  target is col11a1,
  reference is ribl10,
  control is the control sample (healthy or pancreatitis), and
  sample is the tumor sample.

4.2 Results

Quantification of the Change of col11a1 Gene Expression

Two replicas of each sample (healthy and tumor) were amplified with the primers specific for col11a1 (SEQ ID NO: 1 and SEQ ID NO: 2) and ribl10 (SEQ ID NO: 10 and SEQ ID NO: 11). Using the crossing points generated in these amplifications, the changes of col11a1 gene expression in the tumor samples with respect to the healthy control and pancreatitis control were calculated by applying the equation described above (Table 9).

TABLE 9

Col11a1 overexpression values in the 5 tumor samples with respect to the healthy control (PA36) and with respect to the pancreatitis control (PA46)

| Samples | PA14 | PA16 | PA19 | PA27 | PA33 |
|---|---|---|---|---|---|
| Increase in expression with respect to the healthy control (PA36) | 356.9 | 36.5 | 245.2 | 205.1 | 322.0 |
| Increase in expression with respect to Pancreatitis (PA46) | 381.6 | 39.0 | 262.1 | 219.3 | 344.2 |

The results confirmed the data obtained by measuring the gene expression difference with DNA-chips (Example 2), i.e., col11a1 gene expression was greatly increased in the tumor samples with respect to the healthy samples and with respect to the pancreatitis samples.

EXAMPLE 5

Production of Antibodies and Polyclonal Monoclonal Specific for proCOL11A1 Protein 5.1 Materials and Methods 5.1.1 Cloning of Differential Genes in a Heterologous Expression Vector. LCR (Ligase Chain Reaction), Digestion and Ligation Strategy Given that col11a1 gene is very large and given the considerable homology and complexity within the collagen family, a synthetic DNA fragment corresponding to the most specific region of procollagen type 11 A1 subunit (proCOL11A1) was generated. For that reason a conventional PCR-coupled ligase chain reaction (LCR), a computer-aided method for in vitro gene synthesis, was carried out (Au et al., Biochem Biophys Res Commun. 1998 Jul. 9; 248(1):200-3, Rouillard et al., Nucleic Acids Res. 2004 Jul. 1; 32 (Web Server issue): W176-80).

Sequence Comparison

First the amino acid sequences of all the types of collagens were compared, performing multiple alignment with the INRA Multialin v5.4.1 program (Corpet, et al., Nucleic Acids Res. 1998 Jan. 1; 26(1):323-6). In a second step the regions of lower homology between proCOL11A1 and the types of collagen with the highest degree of similarity were sought using the Lalign v2.0 program (Huang et al., Adv. Appl. Math. (1991) 12:337-357). A hydrophobicity plot of the specific proCOL11A1 sequence was then generated by means of the Expasy Server ProtScale program (http://www.expasy.ch/tools/protscale.html) and a hydrophilic region with a high probability of being exposed was selected (Gasteiger et al., The proteomics protocols Handbook, H. Press, 2005; 571-607). An area (amino acids 350-400, Indicated in black in FIG. 3) covering the most specific region of pro-COL11A1 (amino acids 363-393) was identified among the most hydrophilic areas of the protein, so it was selected as the immunogen. The nucleotide sequence encoding the selected region was identified, and the oligonucleotides for LCR were designed on it.

Designing the Oligonucleotides

The Gene2Oligo program (Rouillard et al., 2004, cited above) was used for designing the oligonucleotides. This program allows automatically designing oligonucleotides the sequence of which partially overlaps, having length and denaturation temperature characteristics which allow multiple annealing in homogenous conditions by means of LCR (Table 10). The design program output is the following:

TABLE 10

Oligonucleotides for in vitro synthesis of a of proCOL11A1 fragment by LCR designed with Gene2Oligo. The number of each oligonucleotide shows the position of the start nucleotide.
F: Forward and R: Reverse

| Oligo code | Sequence (5'-3') | SEQ ID NO: |
|---|---|---|
| R0 | TTGGGTGCTGAAGA | 12 |
| F0 | TCTTCAGCACCCAAGGCTGCTCAAGC | 13 |
| R14 | TCTGAGGTTCCTGAGCTTGAGCAGCC | 14 |
| F26 | TCAGGAACCTCAGATAGATGAGGCAAACA | 15 |
| R40 | GAAAATCATCAACGATGTTTGCCTCATCTA | 16 |
| F55 | TCGTTGATGATTTTCAAGAATACAACTATGGA | 17 |
| R70 | GGTAACTTTCCATTGTTCCATAGTTGTATTCTT | 18 |
| F87 | ACAATGGAAAGTTACCAGACAGAAGCTCC | 19 |
| R103 | CAGAAACATGCCTAGGAGCTTCTGTCT | 20 |
| F116 | TAGGCATGTTTCTGGGACAAATGAGCC | 21 |
| R130 | TCTTCAACTGGATTTGGCTCATTTGTCC | 22 |
| F143 | AAATCCAGTTGAAGAAATATTTACTGAAGAATAT | 23 |
| R158 | CCTCTCCCGTTAGATATTCTTCAGTAAATATT | 24 |
| F177 | CTAACGGGAGAGGATTATGATTCCCAGAG | 25 |
| R190 | ATCCTCAGAATTTTTCCTCTGGGAATCATAAT | 26 |
| F206 | GAAAAATTCTGAGGATACACTATATGAAAACAA | 27 |

TABLE 10-continued

Oligonucleotides for in vitro synthesis of a of proCOL11A1 fragment by LCR designed with Gene2Oligo. The number of each oligonucleotide shows the position of the start nucleotide.
F: Forward and R: Reverse

| Oligo code | Sequence (5'-3') | SEQ ID NO: |
|---|---|---|
| R222 | TGCCGTCTATTTCTTTGTTTTCATATAGTGT | 28 |
| F239 | AGAAATAGACGGCAGGGATTCTGATCTTC | 29 |
| R253 | AATCTCCATCTACCAGAAGATCAGAATCCC | 30 |
| F268 | TGGTAGATGGAGATTTAGGCGAATATGATTT | 31 |
| R283 | CATATTCTTTATATTCATAAAAATCATATTCGCCTA | 32 |
| F299 | TTATGAATATAAAGAATATGAAGATAAACCAACAAG | 33 |
| R319 | CTTCATTAGGGGGCTTGTTGGTTTATCTT | 34 |
| F335 | CCCCCCTAATGAAGAATTTGGTCCAGGT | 35 |
| R349 | GTTTCTGCTGGTACACCTGGACCAAATT | 36 |
| F363 | GTACCAGCAGAAACTGATATTACAGAAACAA | 37 |
| R377 | ATGGCCATTTATGCTTGTTTCTGTAATATCA | 38 |
| F394 | GCATAAATGGCCATGGTGCATATgcg | 39 |
| R408 | gtcaagcctccatcgcATATGCACC | 40 |
| R420 | Atggaggcttgac | 41 |

Ligation and LCR-PCR Amplification

The 30 oligonucleotides described in Table 10 were diluted to a concentration of 5 µM. 25 pmol of each oligo were phosphorylated in a total of 5 reactions (6 oligonucleotides per reaction). The reactions were carried out in a total volume of 50 µl. Each reaction consisted of 1.3 µl of MilliQ-H$_2$O, 5 µl of 10× T4 Kinase Buffer, 7 µl of 5 µM oligonucleotides (6 per reaction), 0.7 µl of 75 mM ATP and 1 µl of 10U/µl T4 Kinase. The 5 reactions were incubated at 37PC for 30 minutes and the oligonucleotides phosphorylated were then purified in a Sephadex G-25 column (Amersham). Only 25 µl of reaction were loaded so as to not saturate the column, it was washed with two volumes and the remaining 25 µl were loaded. The two eluates were collected together. Ligase chain reaction (LCR) was performed with the 5 mixtures of phosphorylated and purified oligonucleotides at a final volume of 25 µl. Each vial contained 4 µl of oligonucleotide mixture (5 reactions), 2.5 µl of Ligase Buffer and 2.5 µl of Taq Ligase 4 U/µl (dilution 1:10). The ligation program was 2 minutes at 94° C. and 20 cycles at 94° C. for 30 seconds and at 51° C. for 4 minutes. The "second" PCR was carried out in a final volume of 50 µl. Each vial contained 31.5 µl of MilliQ-H$_2$O, 5 µl of 10× PCR Buffer, 5 µl of 25 mM MgCl$_2$, 2 µl of 25 µM forward primer, 2 µl of 25 µM reverse primer, 1 µl of 10 mM dNTP, 0.5 µl of 5 U/µl Taq polymerase and 3 µl of LCR. The primers used in the second PCR were modified for cloning and their sequence was:

Forward:
(SEQ ID NO: 42)
ATCGGAGAATTCTCTTCAGCACCCAAGGCT;

-continued

Reverse:
(SEQ ID NO: 43)
GCTTCGGACGTCAATTATACGTGGTACCGGTAAA

The amplification program consisted of 10 minutes at 95° C., 30 cycles at 95° C. for 30 seconds, at 55° C. for 30 seconds and at 72° C. for 1 minute, plus a final incubation at 72° C. for 5 minutes. The PCR product stained with ethidium bromide was verified by agarose gel electrophoresis.

The PCR fragment amplified and digested with suitable enzymes was ligated with pET41a vector (Novagen), in turn digested with the same enzymes. pET41a is an expression vector in prokaryotes that includes a GST tag for producing fusion proteins. Approximately 2 μg of the PCR product and 1 μg of vector were digested. The digestion reactions were carried out in 20 μl and each reaction contained 2 μl of 10× buffer specific for each enzyme (Promega, Madison, USA. New England Biolabs, Ipswich, USA), 0.2 μl of 10 mg/ml BSA, 1 μl of 10 U/μl restriction enzyme, DNA (1-2 μg) and up to 20 μl of MilliQ-H2O. The reactions were incubated for 1-2 hours at 37° C. and 10 minutes of inactivation at 65° C., when necessary. The digested products were purified by separation of an ultrapure (cloning grade) 0.75% agarose gel using QIAquick Gel Extraction Kit or QIAquick DNA Kit (Qiagen). The ligation reactions were carried out in 10 μl and incubated overnight at 16° C. in a thermal cycler. Each reaction contained 1 μl of 10× Ligase Buffer, 1 μl of T4 Ligase (New England), 50-100 ng of digested vector, digested insert (the insert/vector molar ratios were optimized in each case) and MilliQ-$H_2O$ up to 10 μl. Competent JM109 cells (Promega) were transformed by means of thermal shock with 1 μl of the ligation reaction. The cells were seeded in LB agar plates with antibiotic, kanamycin, and were incubated at 37° C. for 16 hours in an oven. Autoclaved sticks were applied to between 2-24 of the colonies obtained and these were grown under stirring in LB liquid medium with kanamycin (30 μg/ml) a 37° C. for 16 hours in an orbital incubador. In parallel, PCR screening was performed on the same colonies to identify those that contained recombinant plasmid. To that end, PCR mixtures that included 25 μl of MilliQ-$H_2O$, 5 μl of 10× PCR Buffer, 3 μl of 25 mM $MgCl_2$, 5 μl of 25 μM forward primer [Forward: ATCGGAGAATTCTCTTCAGCACCCAAGGCT (SEQ ID NO: 42)], 5 μl of 25 μM reverse primer [Reverse: GCTTCGGACGTCAATTATACGTGGTACCGGTAAA (SEQ ID NO 43)], 1 μl of 10 mM dNTP and 1 μl of 5 U/μl Taq polymerase were prepared. A colony was dissolved in a tube with 100 μl of MilliQ-$H_2O$, was incubated for 10 minutes at 100° C. and after centrifugation of 5 minutes at maximum speed, 5 μl of the supernatant were taken and were added to the PCR mixture. Those colonies that gave positive results in the PCR test were purified by Miniprep (Promega), verified by sequencing and finally purified on a large scale by means of Midi- or Maxiprep (Qiagen).

5.1.2 Recombinant Protein Expression and Purification

Optimization of Expression Conditions

To estimate optimal fusion protein expression conditions, pilot induction experiments were conducted. Competent BL21-DE3 cells were transformed with all the plasmid constructs and were left to grow at 37° C. overnight in 10 ml of LB with Kanamycin. The next day 10 ml of LB-Kanamycin were inoculated with 500 μl of each of the previous cultures and were left to grow at 37° C. for 2 hours under stirring. The cultures were divided into two parts, one induced with 1 mM isopropyl-β-D-1-thiogalactopyranoside (IPTG) and the other not being induced. After adding IPTG, 500 μl aliquots of each of the cultures were taken at 0, 1, 2, 3, 4 and 5 hours. The collected culture samples were centrifuged, the cell pellets were resuspended in 1× SDS-PAGE buffer and were analyzed in 12% acrylamide gel. Competent BL21-A cells containing an extra basal expression repression system, in the absence of an inducer, were used in certain cases, this being very useful in cases in which the expressed recombinant protein is toxic for the bacterium or inhibits its growth. In this case, the cultures were induced by supplementing the medium with 1 mM IPTG and 0.2% L-arabinose. If a protein band having the expected size appeared only in the induced cultures, the identity thereof was verified by Western blotting using antibodies against the GST tag or specific antibodies against the expressed protein.

Production of Recombinant Proteins

Once the optimal expression conditions were determined, the protocol described in the preceding section was repeated scaling the culture volumes. 250 ml-1000 ml cultures were induced for each of the recombinant proteins. Once the optimal time (2-4 hours) elapsed, the bacteria were collected by centrifugation and the culture medium was removed. The dry bacterial pellets were stored at −80° C. until protein extraction.

Soluble and Insoluble protein extracts were obtained from the pellets by means of the BugBuster Protein Extraction Reagent (Novagen). 5 ml of BugBuster Reagent, 5 KU of rLysozyme (Novagen) and 10 μl of Benzonase (Novagen) were used for every 700 mg of pellet (100 ml of culture). After incubation for 20 minutes at room temperature it was centrifuged at 16,000 g and the supernatant with the soluble fraction was collected. The insoluble proteins (inclusion bodies) were solubilized by means of treatment with rLysozyme and sonication followed by a denaturing buffer (50 mM N-cyclehexyl-3-aminopropanesulfonic acid (CAPS), 0.3% N-lauroylsarcosine, 1 mM dithlothreitol (DTT), to solubilize the protein. The solubilized protein was dialyzed in two steps; first against 20 mM Tris with 0.1 mM DTT to promote refolding by means of the formation of disulfide bridges and finally against 20 mM Tris (Protein Refolding Kit—Novagen). The recombinant proteins of the soluble fraction and the solubilized and refolded inclusion bodies were purified by affinity chromatography.

Protein Purification by Affinity Chromatography

GST-binding fusion proteins were purified by affinity chromatography using GST-Bind Resin Chromatography Kit (Novagen). The protein extracts were loaded after equilibrating GST resin with 10 volumes of binding buffer. The recombinant proteins fused to GST were retained in the column by specific binding to reduced glutathione which is Immobilized in the agarose matrix. Most of the proteins passed through the column and were collected as eluate (flow-through). After washing the column with 5 volumes of washing buffer to detach nonspecifically-bound proteins, the fusion protein was collected adding 1.5 volumes of an elution buffer containing reduced glutathione. Finally, the protein was dialyzed against a phosphate buffer to remove glutathione. The entire process was monitored by analyzing by SDS-PAGE the protein present in each of the different chromatographic fractions in 12% polyacrylamide gel stained with Coomassie blue.

5.1.3 Production of Antibodies 5.1.3.1 Production of Polyclonal Antibodies

Pre-immune serum of New Zealand rabbits was obtained before starting immunizations for use as a control in later experiments. These rabbits were immunized with 5 successive doses of antigen (purified recombinant protein) in incomplete Freund's adjuvant by intramuscular route. Each dose contained about 500 µg of protein and they were administered at an interval of 15 days between doses. Two weeks after the fifth dose, the rabbits were bled to death obtaining about 80 ml of serum per animal. The IgGs were purified by affinity chromatography in columns pre-packed with Protein A Sepharose (HITrap Protein A—Amersham Biosciences). The IgGs were bound to the column in neutral pH conditions and after several washes with phosphate buffer (20 mM $Na_2HPO_4$, pH=7) they were eluted using 0.1 M citrate buffer at pH=3.6. To prevent degradation of the IgGs due to the acidity of the buffer, the pH was equilibrated using a TRIS-HCl solution. To remove the antibodies reactive against the GST tag from the purified serum, purified recombinant GST protein was immobilized by means of the method described above in an amino-link resin (Pierce). This GST resin was used to increase specificity by means of depleting all the sera produced by inoculation of GST-binding fusion proteins. To that end the HiTrap-purified serum was incubated with the GST resin for 30 minutes under stirring, was centrifuged and the supernatant was recovered, depleting anti-GST IgGs. This process was carried out three times using a new resin aliquot every time.

In addition to the in-house production of antibodies, rabbit polyclonal antibodies generated against peptides were ordered (Sigma-Genosys, Cambridge, UK), commercial antibodies from different companies were used and antibodies were requested from other research groups.

5.1.3.2 Production of Monoclonal Antibodies

To generate these monoclonal antibodies, BALB/c mice were hyperimmunized with the previously produced recombinant proteins. B cell hybridomas were then generated using myeloma Sp2/0 cells as a fusion partner following conventional technology. The supernatants which contained the antibodies were then panned by means of ELISA against the purified recombinant pro-COL11A1-GST protein.

5.2 Results

LCR (Ligase Chain Reaction), Digestion and Ligation Strategy

Collagen Sequence Comparison

Figures 1, 2:
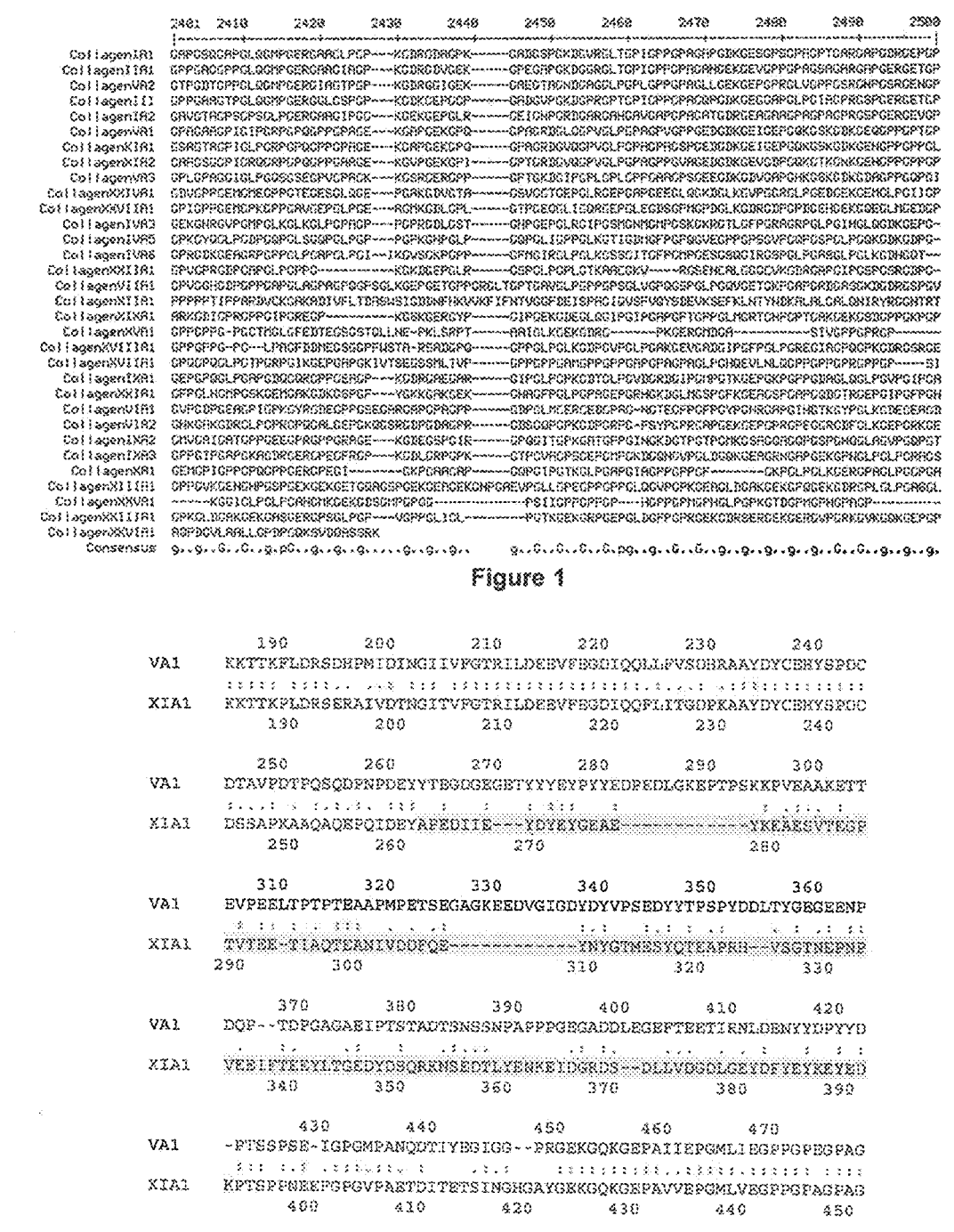

The sequence comparison of all the collagen types (types I to XXVII) showed considerable homology between collagen XI alpha 1 (COL11A1) and collagen V alpha 1 (COL5A1). The analysis also showed homology between COL11A1 and COL11A2. the region of greatest homology is shown as an example in FIG. 1.

The region of lowest homology between the isoforms of greatest similarity (75%), 11A1 and 5A1, was selected for the purpose of being able to generate antibodies against an immunogen of maximum specificity for proCOL11A1. To that end the sequence of these two isoforms was compared by means of the Lalin 2.0 program. The comparison algorithm identified a region of minimum homology between amino acids 363-393 (FIG. 2).

In parallel, a hydrophobicity plot of COL11A1 was generated with the ProtScale program and the Kyte & Doolittle algorithm, which showed several hydrophilic regions in the protein. The hydrophilic domains of a protein have a higher probability of corresponding to exposed areas, and therefore the antibodies generated against those domains will have a higher probability of recognizing the protein in its native conformation in cells and tissues. Curiously, a region between amino acids 350 and 400 covering the most specific region of COL11A1 (363-393) was identified between said hydrophilic regions (FIG. 3). Finally, the region comprised between amino acids 268 and 400 was selected for generating a hydrophilic and specific proCOL11A1 Immunogen. This peptide with 133 amino acids is located in the VAR sub-domain of the N-terminal region of intracellular proCOL11A1 protein, which is processed and removed in the extracellular COL11A1 protein, which is assembled in extracellular collagen fibers. The nucleotide sequence encoding this fragment was used for designing oligonucleotide s for LCR-PCR.

Ligation, LCR-PCR Amplification and Cloning

Figure 4:
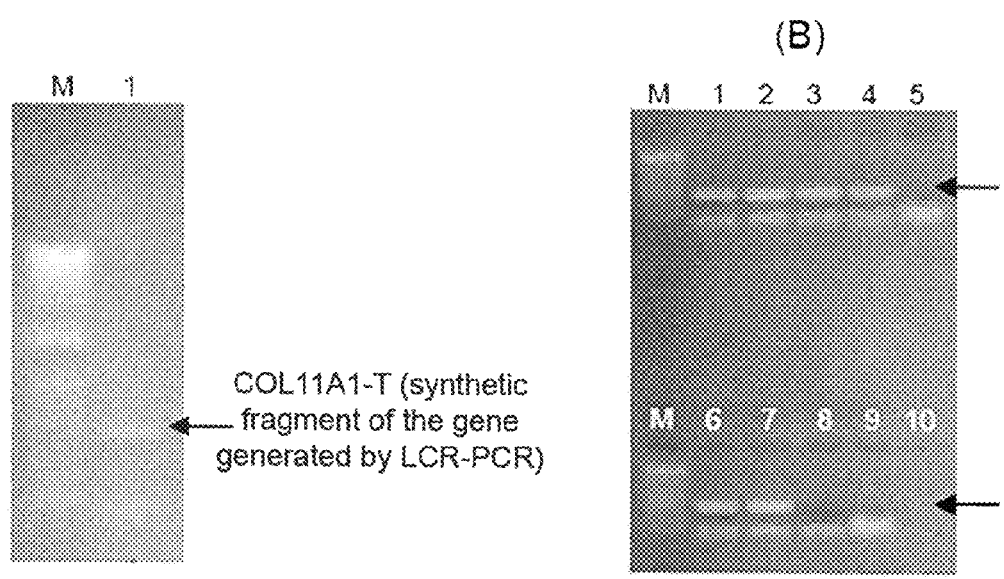
FIG. 4: A) Display of the CSF-PCR product; amplification of the expected proCOL11A1-T fragment 444 nucleotides long is observed. B) Result of screening of transformation colonies; colonies 1-7 turned out to contain the proCOL11A1-T fragment.

Overlapping oligonucleotides covering the encoding sequence of the specific hydrophilic domain (amino acids 268-400) of proCOL11A1, identified according to that described in the preceding section, were designed. This domain was called proCOL11A1-T (truncated) to distinguish it from the whole protein. The oligonucleotides were designed by means of the Gene2Oligo program and assembled by means of LCR followed by PCR, using for PCR a pair of external primers modified with unique cleavage sites for restriction enzymes [Forward primer, with restriction site for EcoRI, sequence: ATCGGAGAAT-TCTCTTCAGCACCCAAGGCT (SEQ ID NO: 42) and reverse primer, with restriction site for PstI, sequence: GCTTCGGACGTCAATTATACGTGGTACCGGTAAA (SEQ ID NO: 43)]. The synthetic fragment generated was viewed in 1% agarose gel stained with ethidium bromide (FIG. 4A), amplification of the expected proCOL11A1-T fragment 444 nucleotides long being observed. Once the insert was generated, the cloning methodology was similar to that described above: digestion of insert and vector with restriction enzymes, purification with affinity minicolumns, ligation and transformation of competent E. coli cells of the JM109 strain. The PCR screening performed on lysates of kanamycin-resistant colonies showed 6 positive and 2 negative clones of the 8 colonies analyzed (FIG. 4B, Result of screening the transformation colonies. Colonies 1-7 contained the pro-COL11A1-T fragment). The plasmids of the positive colonies were purified as described and were stored as stock cultures in glycerin.

Expression and Purification of Recombinant Proteins

Optimization of Expression Conditions

As described in Materials and Methods, bacteria cultures transformed in LB medium were generated, expression of the fusion proteins was induced with IPTG/arabinose, proteins were extracted from said cultures and were analyzed by means of SDS-PAGE followed by staining with Coomassie blue. The SDS-PAGE analysis of protein extracts from cultures transformed with the different expression plasmid constructs in most cases showed the appearance of a band with the expected size exclusive of the culture Induced with IPTG or IPTG/arabinose. It was thus verified that the plasmids generated by cloning into the pET41a vector of the gene col11a1-T were functional; i.e., they directed the expression of the corresponding proteins fused to GST. Expression of the GST protein in cultures transformed with the pET41a vector was also confirmed. In most cases a maximum expression level was obtained 4 hours after induction with 1 mM IPTG and 0.2% arabinose. These conditions were set to a larger scale for the expression experiments. The location of the recombinant proteins, as well as their expression levels were further determined. GST-COL11A1-T and GST proteins were expressed at a high level and they were located in the supernatant.

Figure 5:
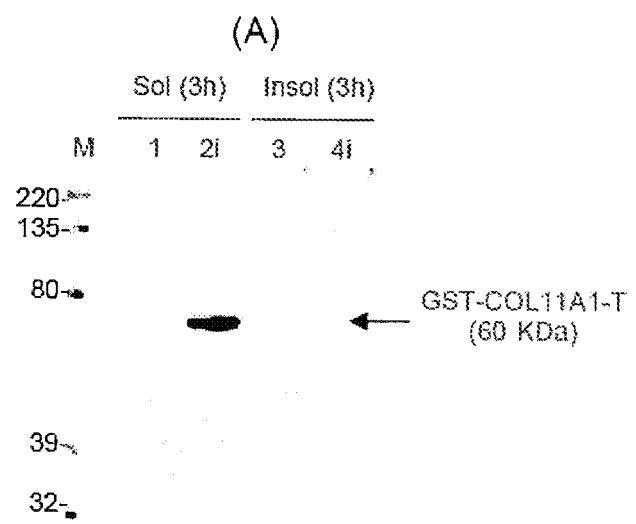
FIG. 5: Confirmation of the identity of the expressed fusion proteins by Western blotting with anti-GST-COL11A1.

To confirm the identity of the expressed proteins, the bacterial culture extracts were analyzed by Western blotting using a monoclonal antibody directed against the GST tag (anti-GST mouse mAb, Novagen). This analysis confirmed that the bands having the expected size observed in the SDS-PAGE gels corresponded to GST-binding fusion proteins (FIG. 5).

Production of Recombinant Proteins on a Larger Scale

GST-COL11A1-T fusion protein expression on a larger scale was approached for the purpose of purifying it and injecting it into rabbits to obtain polyclonal antibodies. Free GST protein was also expressed to use it in later depletion experiments. To that end the experiments were scaled to a smaller scale.

Protein Purification by Affinity Chromatography

GST-COL11A1-T was purified following the protocol described in Materials and Methods by means of affinity chromatography in glutathione columns (GST-Bind Kit, Novagen). Densitometric quantification of the protein bands (ImageJ) allowed establishing the protein recovery efficiency at 40-50% and fusion protein enrichment in the different column fractions, which was less than 15% in the initial extract and greater than 80% in the eluate.

Production of Polyclonal Antibodies

Two rabbits were immunized by means of intramuscular injection of purified GST-COL11A1-T fusion proteins in Freund's adjuvant. After the first immunizations bleedings were performed every 15 days to monitor the increase in the titer and the specificity of the anti-serum. To that end recognition of the antigen was tested by Western blotting. An increase in the titer of the sera and affinity for GST-COL11A1-T recombinant proteins, especially in the last two bleedings (6 and 7), was confirmed. The Immunization also generated a very intense reactivity against the GST protein, which is not surprising given the size of GST with respect to that of COL11A1-T. To reduce possible cross reactions of anti-GST antibodies on other proteins in later phases of the project, the sera were depleted by means of affinity chromatography. To that end, GST protein was immobilized in a glutathione matrix and the serum was incubated twice with said GST matrix. Specificity of the anti-COL11A1-T sera was thus improved.

Production of Monoclonal Antibodies

Figure 6:
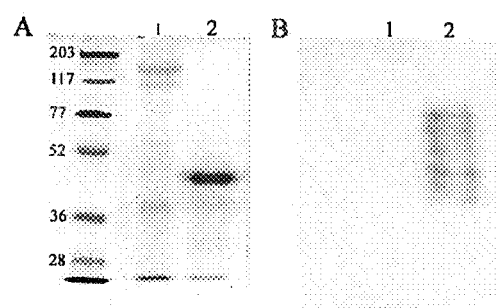
FIG. 6: Verification of the absence of cross reactivity of the 1E8.33 monoclonal antibody (mAb) with collagen V. Lane 1: recombinant proCOL5A1. Lane 2: pro-COL11A1-T. A) Coomassie blue stained gel as loading control of both proteins. B) Western blot (WB) with 1E8.33 mAb; correct detection of proCOL11A1 and no detection of COL5A1 are observed.
Figure 7:
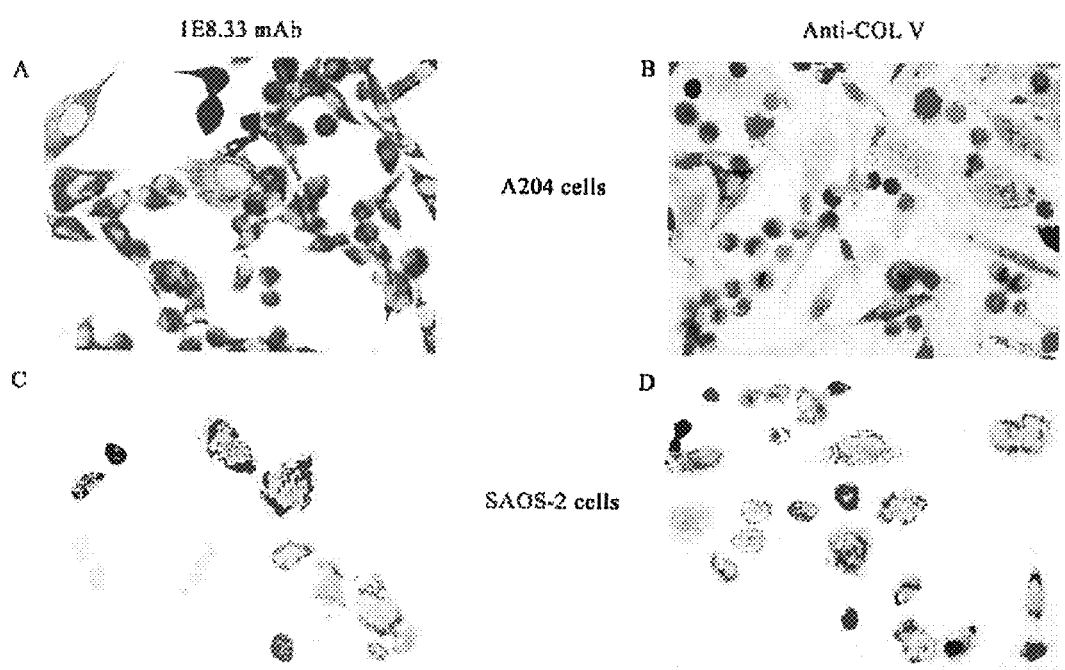
FIG. 7: Immunocytochemical assays for checking 1E8.33 mAb specificity for proCOL11A1 and the absence of cross reactivity with proCOL5A1. A and B) A204 rhabdomyosarcoma cells, which mostly express proCOL11A1. C and D) SAOS-2 osteosarcoma cells, which mostly expressly proCOL5A1. A and C) detection by means of 1E8.33 mAb. B and D) detection by means of rabbit polyclonal anti-proCOL5A1. Intense staining of proCOL11A1 is observed in A204 cells, but not in SAOS cells −2. The antibody to proCOL5A1 showed the reverse pattern.

To generate these monoclonal antibodies, BALB/c mice were hyperimmunized with the previously produced recombinant proteins. B cell hybridomas were then generated using myeloma Sp2/0 cells as a fusion partner following conventional technology. The supernatants which contained the antibodies were then panned by means of ELISA against the purified recombinant pro-COL11A1-GST protein. Finally, the murine antibodies were sub-isotyped by means of the Monoclonal Antibody Isotyping Kit (Roche Diagnostics GmbH). A monoclonal antibody (IgG1, kappa), corresponding to 1E8.33 clone, which had a high affinity for the proCOL11A1-T protein, was selected. The specificity of the antibody for proCOL11A1 and the absence of cross reactivity with collagen type V (which has the highest homology with respect to type XI, was carried out by means of Western blot (FIG. 6). The detection of proCOL11A1 In A204 rhabdomyosarcoma cell lines, which mostly express proCOL11A1 according to mRNA analysis, and in SAOS-2 osteosarcoma cells, which mostly express COL5A1, was further confirmed by immunocytochemistry, intense intracellular staining in A204 cells, and mild intracellular staining in SAOS-2 cells being observed, and showing a staining pattern opposite that of proCOL5A1, which was checked by using a polyclonal rabbit antibody against said protein (FIG. 7).

The $V_L$ and $V_H$ domains of 1E8.33 antibody were sequenced using previously described processes (Fernández-Sánchez et al. Immunol Letters 2009, 123:125-131), and checked by means of Chromas Lite 2.01 tools (Technelysium Pty Ltd.) and Bioedit sequence Alignment Editor 7.0.9 (Tom Hall, Ibis Biosciences, Carlsbad, USA), and analyzed by IMTG/V-QUEST (http://imtg.cines.fr) and GeneBank IgBLAST (http://www.ncbi.nih.gov). The nucleotide and amino acid characteristics of the $V_L$ and $V_H$ regions are summarized in Table 11, and the characteristics of the CDR are summarized in Table 12.

TABLE 11

Characterization of the gene segments and amino acid substitutions of the $V_L$ and $V_H$ regions of 1E8.33 monoclonal antibody according to IMGT/V-QUEST

| 1E8.33 mAb | Genes of the germ line | | | Changes in the amino acids | | | | | |
|---|---|---|---|---|---|---|---|---|---|
| | $V_H$ | $D_H$ | $J_H$ | FR1 | CDR1 | FR2 | CDR2 | FR3 | CDR3 |
| $V_H$ | IGHV1S34*01 | IGHD5 | IGHJ4*01 | 1<br>A17 > S | 0 | 1<br>H46 > Q | 1<br>S57 > N | 3<br>Q69 > R<br>K70 > N<br>E97 > G | 0 |
| $V_L$ | IGKV4-50*01 | N.A. | IGKJ1*01 | 0 | 0 | 0 | 0 | 1<br>A100 > D | 0 |

N.A.: Does not apply
*The asterisk is part of the manner of assigning alleles as established by the program

TABLE 12

Characteristics of the CDR of the 1E8.33 monoclonal antibody
*: number of residues in CDR1-CDR2-CDR3

| 1E8.33 mAb | Amino acid residues in CDR1-CDR2-CDR3 | | |
|---|---|---|---|
| | CDR1 | CDR2 | CDR3 |
| $V_H$<br>8-8-12* | GYSFTGYY | INCYNGAT | AIWDYEFHVMDY |
| $V_L$<br>5-3-9 | SSVNY | YTS | QQFTSSPWT |

*: number of residues in CDR1-CDR2-CDR3

It was found that 1E8.33 monoclonal antibody (mAb) is a new antibody that had not previously been described.

Figure 8:
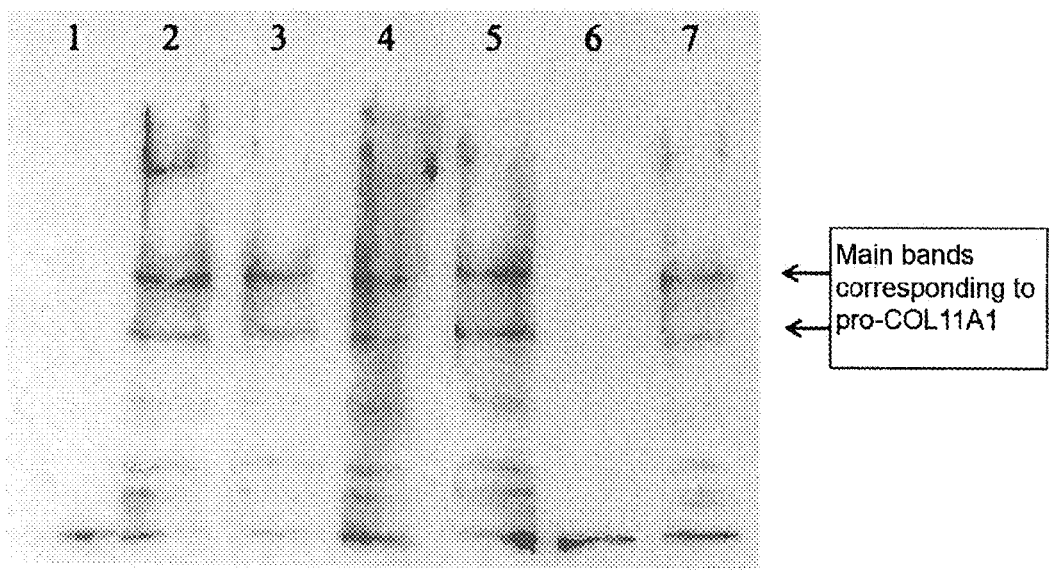
FIG. 8: 1E8.33 mAb blocking test for locating the epitope, performed by means of Western blot of A204 cells. The detection was performed with a mixture of the antibody and different peptides. Lane 1: negative control without antibody. Lane 2: FQEYNYG. Lane 3: YNYGTMES. Lane 4: FQEYNYGTMES. Lane 5: YNYGTMESYQTE. Lane 6: YNYGTMESYQTEAPR. Lane 7: positive control with the unblocked 1E8.33 mAb. Complete blocking was observed only in lane 6.

The proCOL11A1 epitope detected by the 1E8.33 antibody was mapped, assaying it against several peptides having 15 amino acids (overlapping in 12 amino acids), covering residues 255-409 of proCOL11A1. Antibody blocking assays with several peptides corroborated this assertion because only the mentioned peptide prevented detection of proCOL11A1 in A204 cells by the monoclonal antibody (FIG. 8).

EXAMPLE 6

Differential proCOL11A1 Protein Expression in Pancreatic Tissue Samples Using Polyclonal and Monoclonal Antibodies Specific to proCOL11A1 by Means of Immunohistochemistry 6.1 Materials and Methods Immunohistochemistry A microtome was used to cut sections of tissue biopsies fixed in formol and included in paraffin. The 3-4 µm sections were dried overnight at 54-56° C. in an oven. Pre-treatment with citrate buffer at pH=6.4 was applied in a pressure cooker for 4 minutes. After titration to adjust the suitable dilution, the preparations were incubated with the polyclonal antibodies specific to proCOL11A1 at a 1:1200 dilution in S2022 diluent (Dako, Carpinteria, Calif.) and with 1E8.33 monoclonal antibody at a 1:500 dilution. EnVision K4003 (Dako) detection system was used and it was developed with diaminobenzidine (Dako).

Fifty-three cases of pancreatic ductal adenocarcinoma, 2 cases of ampullary tumor and 24 cases of chronic pancreatitis were analyzed with the polyclonal antibody specific to proCOL11A1 obtained in Example 5.

Likewise, 52 cases of pancreatic ductal adenocarcinoma and 19 cases of chronic pancreatitis were analyzed with the specific monoclonal antibody to proCOL11A1 (1E8.33 clone) described in Example 5.

Immunostaining was performed with a double-blind assay by 2 different pathologists. The scores were:

0 (no visible staining without a lens);

1 (visible staining with 20× lens);

2 (visible staining with 10× lens); and 3 (visible staining with 4× lens).

The immunostained trays also were quantified by means of image analysis using the QWin program (Leica). This study was performed on images of the most stained areas. The images were taken with a 20 magnification (20×) lens of an Olympus BX61 microscope and were stored in an Olympus Dp70 camera. 7 different parameters were considered: number of positive cells; surface of the positive cells; surface of the stained cells; reference area; number of positive cells/reference area; surface of the stained cells/reference area; number of positive cells/mm$^2$; and saturation index in a range of 0 to 255.

Statistical Data Analysis

Assuming unequal variances, Welch's test was used for determining the significance of the differences in the image data between pancreatic ductal adenocarcinoma (PDAC) and chronic pancreatitis. The ANOVA test was also applied. The correlation between various image parameters was evaluated with Spearman's rank correlation test. The sensitivity and specificity of proCOL11A1 was represented as an analysis of the receiver operating characteristics (ROC). A ROC area under the curve (AUC) of 1 indicates perfect discrimination (PDAC vs. chronic pancreatitis), whereas an area of 0.5 indicates that discrimination is not better than random choosing. The position of the cut-off point in the curve will determine the number of true positives, true negatives, false positives and false negatives. All the analyses were implemented using the "Statistical Package for the Social Sciences (SPSS 13)" and MedCalc v9.4.1.0.

6.2 Results

Analysis of proCOL11A1 Protein Expression by Immunohistochemistry in Biological Samples from Individuals with PDAC, Chronic Pancreatitis and Controls ProCOL11A1 protein expression was studied in histological sections taken from pancreatic biopsies from individuals with PDAC, individuals with ampullary tumor and from biopsies from individuals with chronic pancreatitis, without cancer. The purpose of these experiments was to determine the cell type responsible for expression of this protein as well as to evaluate the expression pattern in the three pancreatic pathologies.

Figure 9:
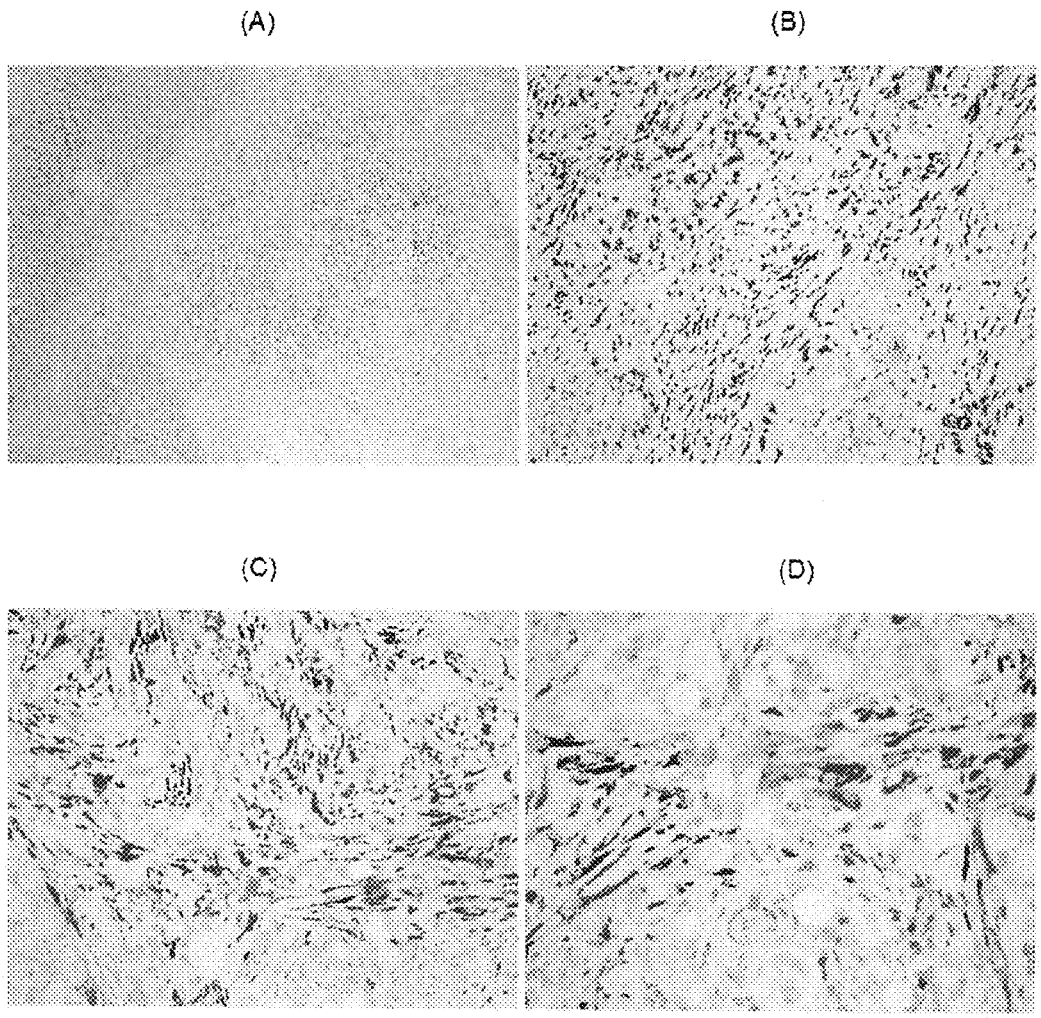
FIG. 9: Immunohistochemical detection of proCOL11A1 protein in histological sections of pancreatic biopsies from individuals with pancreatic ductal adenocarcinoma (PDAC). (A) View of Infiltrating pancreatic ductal adenocarcinoma, 25×. (B, C and D) Detail of the tumor and stroma. Cytoplasmic staining of desmoplastic stroma fibroblasts is observed. 200×, 200× and 400×.
Figure 10:
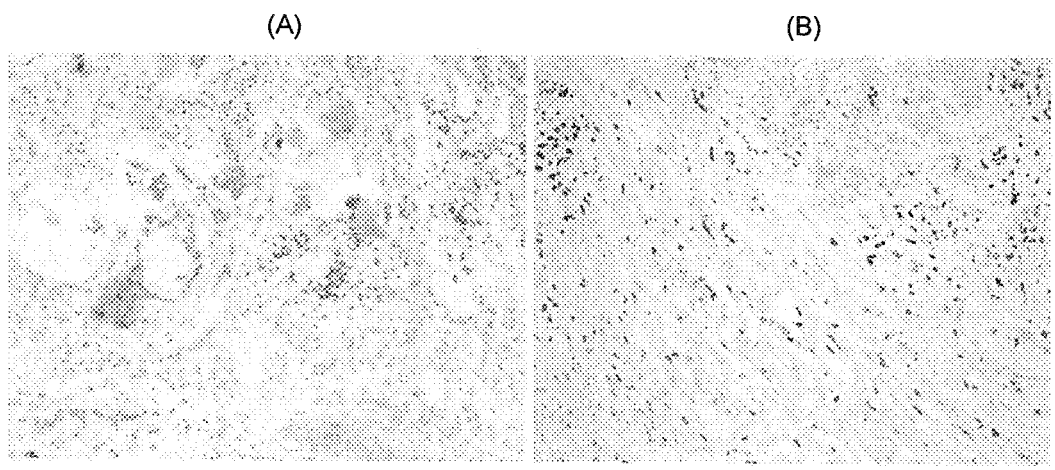
FIG. 10: Immunohistochemical detection of proCOL11A1 protein in histological sections of pancreatic biopsies from individuals with ampullary tumor (A) and from individuals with chronic pancreatitis (B).

On one hand, the polyclonal antibody generated against COL11A1-T (FIGS. 9 and 10) was used. The immunohistochemical detection of proCOL11A1 in the 53 patients with moderately differentiated PDAC analyzed was positive in the vast majority of fibroblasts of the desmoplastic stroma surrounding the tumor, a strong intracytoplasmic staining grade being observed (+++). In the 24 pancreatitis samples, most (>95%) of the fibroblasts were negative for proCOL11A1, even though very localized staining (++) was observed in very few fibroblasts of the most damaged areas. In the two ampullary tumor samples staining with anti-COL11A1-T gave negative results, although the areas of stroma were less abundant than in PDAC samples. 83% specificity and 96% sensitivity levels demonstrate that the anti-proCOL11A1 polyclonal antibody has been proven useful as a marker for determining the prognosis, diagnosis and differential diagnosis of pancreatic ductal adenocarcinoma vs. pancreatitis.

Figure 11:
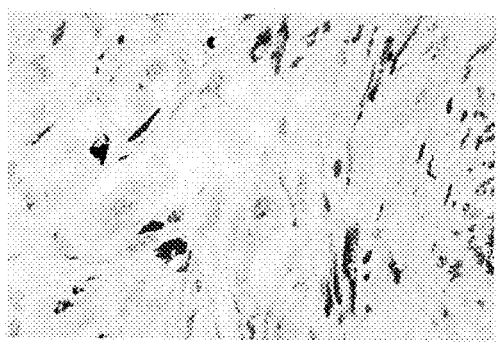
FIG. 11: Immunohistochemical detection of proCOL11A1 in fibroblasts associated with pancreatic ductal adenocarcinoma. Staining with the mAb to proCOL11A1 (1E8.33 clone) (×400).

On the other hand, the analysis of proCOL11A1 protein expression was performed by immunohistochemistry in biological samples from Individuals with PDAC and chronic pancreatitis, using 1E8.33 monoclonal antibody. The high sensitivity and specificity of proCOL11A1 staining was maintained when using 1E8.33 monoclonal antibody (FIG. 11).

EXAMPLE 7

Evaluation of proCOL11A1 as a Marker for the Diagnosis and Prognosis of Pancreatic Ductal Adenocarcinoma and as a Marker for the Differential Diagnosis of Pancreatic Ductal Adenocarcinoma Vs. Chronic Pancreatitis Immunohistochemical analysis of tumor samples from individuals with pancreatic ductal adenocarcinoma (PDAC) in which there was peritumoral stroma proliferation was carried out using 1E8.33 monoclonal antibody (Example 5), and the immunostaining was compared with respect to control samples from individuals with chronic pancreatitis.

In a study carried out with 71 subjects: 52 cases of pancreatic cancer (PDAC) and 19 cases of chronic pancreatitis, the proCOL11A1s immunodetection by means of specific monoclonal antibody (1E8.33) allowed discriminating between PDAC and chronic pancreatitis with high precision: 74% specificity, 94% sensitivity. This is clinically very important because there is a significant percentage of cases in which the differential diagnosis of pancreatic cancer (PDAC) and chronic pancreatitis presents difficulties. Even the anatomopathological analysis of the pancreatic biopsy may not be conclusive in cases in which the pancreatic parenchyma is highly degraded or the amount of biopsied material is scarce.

EXAMPLE 8

Evaluation of proCOL11A1 as Marker for the Diagnosis Differential Diagnosis and Prognosis of Different Types of Carcinomas A battery of immunohistochemical analyses was additionally carried out in human tissues using 1E8.33 monoclonal antibody (Example 5) for the purpose of evaluating the potential of proCOL11A1 as a marker for the diagnosis, differential diagnosis and prognosis in different types of cancer. To that end, tumor samples in which there was peritumoral stroma proliferation were taken, and the immunostaining was compared with respect to healthy control samples and/or benign fibrotic samples of the same organ. The results obtained until now clearly show the potential diagnosis and prognosis of this proCOL11A1 marker.

8.1 Infiltrating Breast Carcinoma. Differential Diagnosis of Infiltrating Ductal Breast Adenocarcinoma Vs. Sclerosing Adenosis In a study carried out with 103 subjects: 51 cases of infiltrating breast carcinoma, and 52 cases of benign fibrotic lesions of the breast (sclerosing adenosis), proCOL11A1 immunodetection by means of 1E8.33 specific monoclonal antibody allowed discriminating between infiltrating ductal breast adenocarcinoma and benign fibrosis with high precision: AUC=0.97, 92% specificity, 96% sensitivity.

Figure 12:
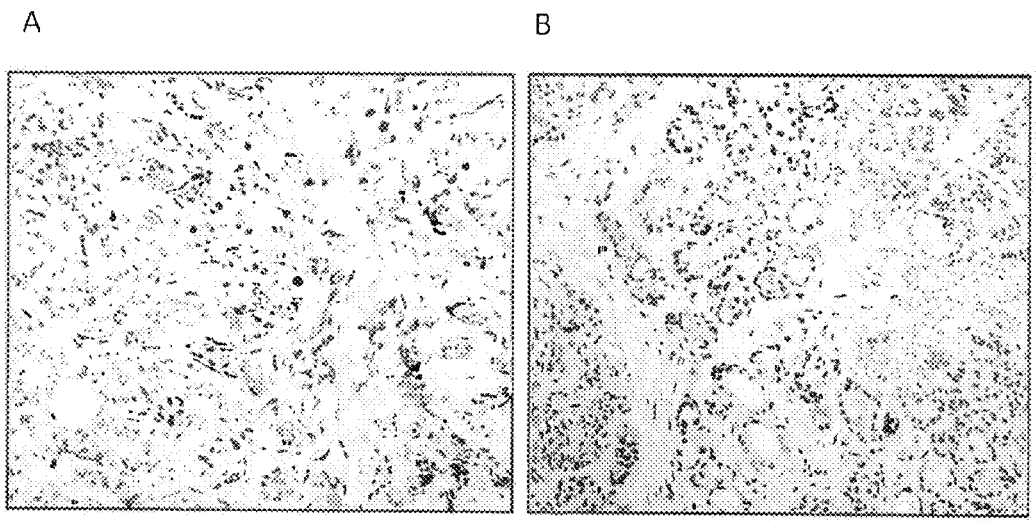
FIG. 12: Immunostaining of proCOL11A1 with 1E8.33 mAb of breast tissue with an Infiltrating tumor (A) and of breast tissue with sclerosing adenosis and without the presence of a tumor (B). Clear staining is observed in the tissue tumor, and none is observed in the benign tissue.
Figure 13:
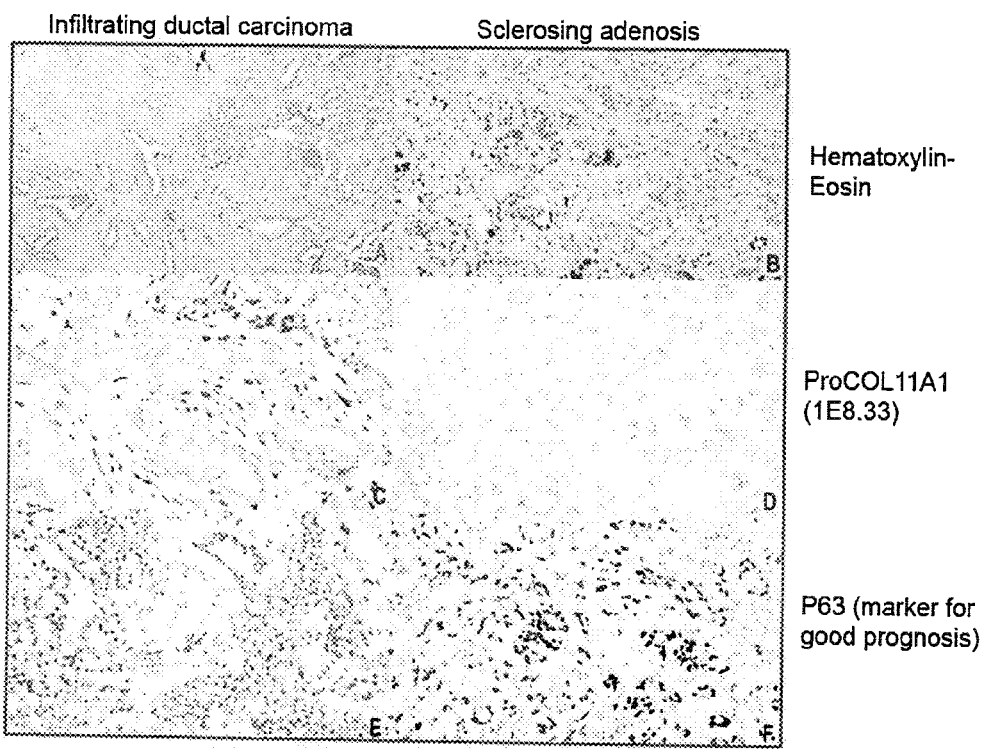
FIG. 13: Staining of breast tissue with an infiltrating ductal carcinoma (A, C, E) and of breast tissue with sclerosing adenosis and without any tumor (B, D, F) with hematoxylin-eosin (A, B), with anti-proCOL11A1 1E8.33 antibody (C, D) and with anti-p63 antibody, which is a poor prognosis marker currently used in characterizing breast tumors (E, F). A reverse pattern is observed between proCOL11A1 staining and p63 staining, demonstrating that proCOL11A1 is an Indicator of tumor aggressiveness.

Conclusions:

The anti-proCOL11A11E8.33 monoclonal antibody has proven to be useful as a marker for determining the prognosis, diagnosis and differential diagnosis of infiltrating ductal breast adenocarcinoma vs. sclerosing adenosis of the breast (FIGS. 12 and 13).

8.2 Infiltrating Breast Carcinoma. Differential Diagnosis of Infiltrating Breast Carcinoma Vs. Lesions Benign In a study carried out with 161 subjects: 102 cases of infiltrating breast carcinoma, and 59 cases of benign fibrotic lesions of the breast, proCOL11A1 immunodetection by means of 1E8.33 specific monoclonal antibody allowed discriminating between infiltrating breast cancer and benign fibrosis with high precision: AUC=0.88, 81% specificity, 92% sensitivity.

Conclusions:

The anti-proCOL11A1 monoclonal antibody has proven to be useful as a marker for determining the prognosis, diagnosis and differential diagnosis of infiltrating ductal breast adenocarcinoma vs. lesions benign.

8.3 Infiltrating Breast Carcinoma. Differential Diagnosis of Infiltrating Ductal Breast Adenocarcinoma Vs. Carcinoma In Situ In a study carried out with 36 subjects with breast carcinoma: 29 of them having an infiltrating tumor, and the remaining seven having carcinoma in situ, proCOL11A1 immunodetection by means of 1E8.33 specific monoclonal antibody allowed discriminating between infiltrating ductal breast adenocarcinoma and carcinoma in situ with high precision: 79.31% specificity, 71.43% sensitivity.

Conclusions:

The anti-proCOL11A1 1E8.33 monoclonal antibody has proven to be useful as a marker for determining the prognosis, diagnosis and differential diagnosis of infiltrating ductal breast adenocarcinoma vs. carcinoma in situ.

8.4 Bronchoalveolar Adenocarcinoma. Prognosis, Diagnosis and Differential Diagnosis of Lung Adenocarcinoma with a Bronchioloalveolar Pattern Vs. Bronchoalveolar Adenocarcinoma For the purpose of investigating the usefulness of 1E8.33 monoclonal antibody, specific for proCOL11A1, in the detection of stromal invasion in bronchioloalveolar adenocarcinomas, immunostaining was carried out with said 1E8.33 monoclonal antibody in a series of 9 cases of bronchoalveolar adenocarcinoma and 6 cases of lung adenocarcinoma with a bronchioloalveolar pattern.

The results clearly showed the absence of staining in 7 of the 9 cases of bronchoalveolar adenocarcinoma whereas the 6 cases of adenocarcinoma with a bronchioloalveolar pattern were stained (p=0.0034).

Conclusions:

The anti-proCOL11A11E8.33 monoclonal antibody has proven to be useful as a marker for determining the stromal invasion in borderline cases of bronchoalveolar adenocarcinoma and is therefore useful for the prognosis, diagnosis and differential diagnosis of bronchioloalveolar adenocarcinoma vs. lung adenocarcinoma with a bronchioloalveolar pattern.

Figure 14:
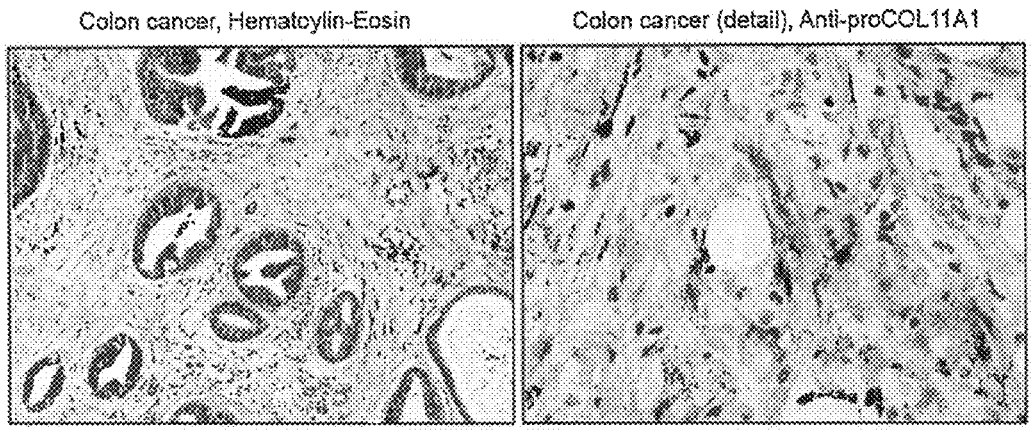
FIG. 14: Staining of fibroblasts from histological sections of colon biopsies from individuals with colon carcinoma. Staining with eosin-hematoxylin and 1E8.33 mAb to proCOL11A1.

8.5 Colon Adenocarcinoma. Prognosis, Diagnosis and Differential Diagnosis of Adenocarcinoma Colon Vs. Benign Fibrosis In a study carried out with 64 subjects: 29 cases of colon adenocarcinoma, 6 cases control of benign fibrosis (2), infarction (2) and diverticulitis (2), and 29 internal controls extracted from a non-tumor areas of the corresponding colon with cancer, proCOL11A1 Immunodetection by means of the 1E8.33 monoclonal antibody showed the presence of said marker (proCOL11A1) in the stroma in 100% of the colon cancer cases, and only in 5% of the controls, as well as the absence in 100% of the fibroblasts of non-tumor areas of the corresponding colon with cancer (FIG. 14)

Staining of fibroblasts from histological sections of colon biopsies from individuals with colon carcinoma. Staining with eosin-hematoxylin and proCOL11A1 monoclonal antibody (1E8.33 clone).

Conclusions:

The anti-proCOL11A1 1E8.33 monoclonal antibody has proven to be useful as a marker for the prognosis, diagnosis and differential diagnosis of adenocarcinomas vs. other benign colon pathologies.

8.6 Head and Neck Carcinoma. Diagnosis, Differential Diagnosis and Prognosis of Infiltrating Squamous Ear, Nose and Throat Area Carcinomas In a series of 50 cases of malignant head and neck tumors (8 women and 42 men between 45 and 85 years of age), 9 cases of mouth cancer, 11 cases of pharynx cancer, 11 cases of larynx cancer, 17 cases of tongue cancer, 1 case of nose cancer, and 1 case of maxillary sinus cancer, proCOL11A1 immunodetection with the 1E8.33 monoclonal antibody allowed confirming the presence of proCOL11A1 in 90% of the samples analyzed. Complete absence of specific staining was observed in only 1 mouth cancer sample, 1 tongue cancer sample and 3 larynx cancer samples. The absence of staining in normal tissue was confirmed by analyzing the normal tissue adjacent to the tumor samples studied (benign squamous epithelium).

Figure 15:
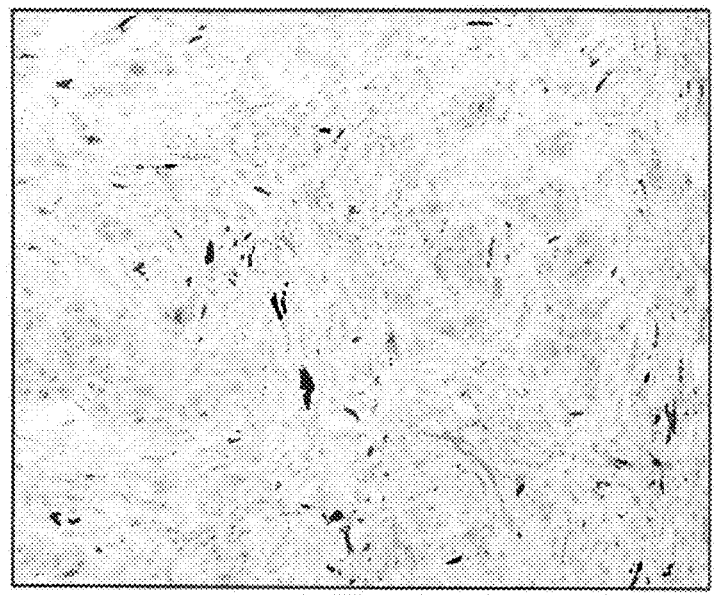
FIG. 15: Immunohistochemical detection of proCOL11A1 in fibroblasts from histological sections of biopsies of the larynx from individuals with laryngeal carcinoma. Staining with anti-proCOL11A1 mAb (1E8.33 clone) (×400).

Conclusions:

The anti-proCOL11A1 monoclonal antibody has proven to be useful as a marker for determining the prognosis, diagnosis and differential diagnosis of infiltrating squamous ear, nose and throat area carcinomas vs. other benign pathologies (FIG. 15).

8.7 Peritoneal Carcinoma. Diagnosis and Prognosis of Peritoneal Carcinomatosis

In a series of paraffin-embedded histological samples of peritoneal implants of adenocarcinomas from the following primary tumors: 6 cases of colon cancer and 5 cases of female genital (endometrial and ovarian) cancer, proCOL11A1 immunodetection with the 1E8.33 monoclonal antibody allowed confirming the presence of proCOL11A1, which is focally and intensely expressed in fibroblasts of the desmoplastic stroma tumor of peritoneal implants of adenocarcinomas of a colonic, endometrial and ovarian origin; the staining was more intense in the differentiated focal points.

Figure 16:
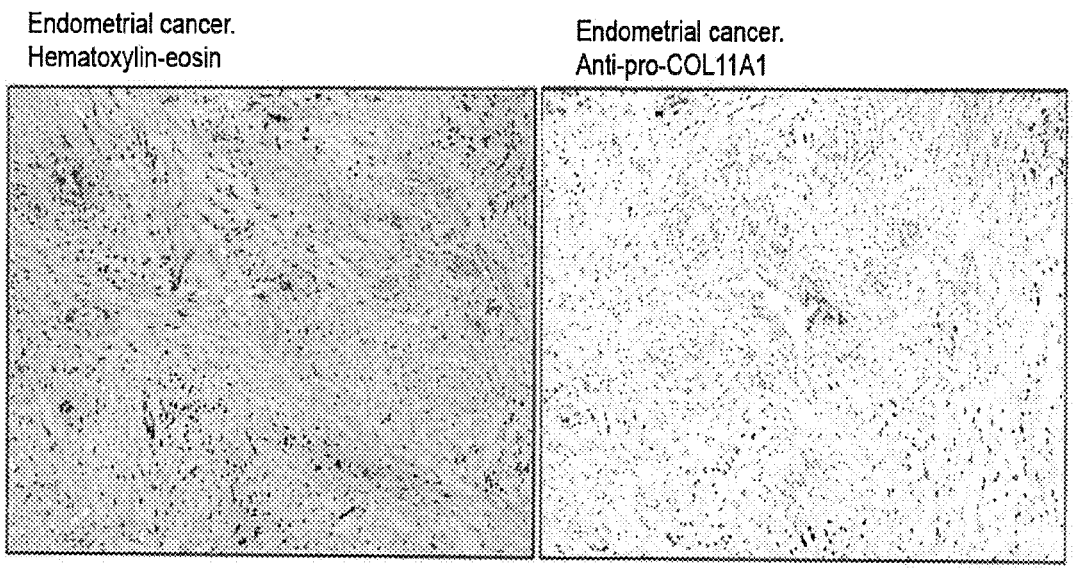
FIG. 16: Staining of fibroblasts from histological sections of biopsies of the desmoplastic stroma tumor of peritoneal implants from individuals with adenocarcinomas of an endometrial origin. Staining with eosin-hematoxylin and with anti-proCOL11A1 mAb (1E8.33 clone).

Conclusions:

This preliminary study demonstrates that the peritumoral fibroblasts of peritoneal implants express proCol11A1 (FIG. 16). The anti-proCOL11A1 monoclonal antibody has proven to be useful as a marker for the prognosis, diagnosis and differential diagnosis of peritoneal carcinomatosis.

The invention claimed is:

1. An in vitro method for detecting an invasive carcinoma selected from the group consisting of invasive colon carcinoma, invasive bladder carcinoma, infiltrating ductal breast adenocarcinoma, and invasive pancreas ductal adenocarcinoma, the method comprising:
   a) detecting in a sample obtained from a patient the proCOL11A1 protein;
   b) comparing at least one of the following:
   the detected amount of proCOL11A1 protein in said sample from said patient with the amount of proCOL11A1 protein detected in a control sample; and
   c) correlating the result obtained in step b) with the presence in the patient of an invasive carcinoma selected from the group consisting of invasive colon carcinoma, invasive bladder carcinoma, infiltrating ductal breast adenocarcinoma, and invasive pancreas ductal adenocarcinoma,
   wherein the detection step a) is performed with a monoclonal antibody or a fragment of said antibody binding specifically to proCOL11A1 protein, comprising within the heavy chain variable region ($V_H$) the following complementarity determining regions (CDRs):
      a CDR comprising the amino acid sequence shown in SEQ ID NO: 3 (GYSFTGYY) [CDR-H1];
      a CDR comprising the amino acid sequence shown in SEQ ID NO: 4 (INCYNGAT) [CDR-H2]; and
      a CDR comprising the amino acid sequence shown in SEQ ID NO: 5 (AIWDYEFHVMDY) [CDR-H3]; and
   comprising within the light chain variable region (VL) the following complementarity determining regions (CDRs):
      a CDR comprising the amino acid sequence shown in SEQ ID NO: 6 (SSVNY) [CDR-L1];
      a CDR comprising the amino acid sequence YTS [CDR-L2]; and
      a CDR comprising the amino acid sequence shown in SEQ ID NO: 7 (QQFTSSPWT) [CDR-L3]; and
   wherein said correlation is an increase in the detected amount of proCOL11A1 protein in said sample from said patient with respect to the amount of proCOL11A1 protein detected in a control sample.

2. The method of claim 1, wherein the sample in step a) is a tissue sample selected from the group consisting of colon, bladder, breast and pancreas.

3. The method of claim 2, wherein the tissue sample is obtained by biopsy, cystoscopy or surgical resection.

4. The method of claim 1, wherein the sample in step a) is selected from a group consisting of bile, gastric flow exudate, feces, urine, plasma, saliva, blood, semen and serum.

5. The method of claim 1, wherein the sample in step a) is obtained from a patient selected from the group consisting of a patient in whom a carcinoma has not been previously diagnosed; a patient in whom a carcinoma has been previously diagnosed; and a patient undergoing treatment, or who has been previously treated, for a carcinoma.

6. The method of claim 1, wherein the detection of proCOL11A1 protein in step a) comprises obtaining a protein extract from the sample, contacting the protein extract from the sample with a proCOL11A1 protein-specific antibody under conditions allowing the formation of an antibody-proCOL11A1 protein complex.

7. The method of claim 6, wherein said proCOL11A1 protein-specific antibody is an antibody that recognizes an epitope located in the proCOL11A1 protein N-terminal VAR domain.

8. The method of claim 6, further comprising the detection and quantification of the antibody-proCOL11A1 protein complex formed.

9. An in vitro method for differentially diagnosing an invasive carcinoma selected from the group consisting of colon adenocarcinoma versus benign lesions; infiltrating ductal breast adenocarcinoma versus breast carcinoma in situ; invasive bladder carcinoma versus superficial bladder carcinoma; and pancreatic ductal adenocarcinoma versus ampullary tumor, the method comprising:
   a) detecting in a sample obtained from a patient proCOL11A1 protein;
   b) comparing at least one of the following:
   the detected amount of said proCOL11A1 protein in said sample from said patient with the amount of proCOL11A1 protein detected in a control sample; or c) correlating the result obtained in step b) with the presence in the patient of an invasive carcinoma selected from the group consisting of invasive colon adenocarcinoma, infiltrating ductal breast adenocarcinoma, invasive bladder carcinoma, and pancreatic ductal adenocarcinoma, wherein the detection step a) is performed with a monoclonal antibody or a fragment of said antibody binding specifically to proCOL11A1 protein, comprising within the heavy chain variable region ($V_H$) the following complementarity determining regions (CDRs):

a CDR comprising the amino acid sequence shown in SEQ ID NO: 3 (GYSFTGYY) [CDR-H1];

a CDR comprising the amino acid sequence shown in SEQ ID NO: 4 (INCYNGAT) [CDR-H2]; and a CDR comprising the amino acid sequence shown in SEQ ID NO: 5 (AIWDYEFHVMDY) [CDR-H3]; and comprising within the light chain variable region (VL) the following complementarity determining regions (CDRs):

a CDR comprising the amino acid sequence shown in SEQ ID NO: 6 (SSVNY) [CDR-L1];

a CDR comprising the amino acid sequence YTS [CDR-L2]; and a CDR comprising the amino acid sequence shown in SEQ ID NO: 7 (QQFTSSPWT) [CDR-L3]; and wherein said correlation is an increase in the detected amount of proCOL11A1 protein in said sample from said patient with respect to the amount of proCOL11A1 protein detected in a control sample.

* * * * *